US007951838B2

(12) United States Patent
La et al.

(10) Patent No.: US 7,951,838 B2
(45) Date of Patent: May 31, 2011

(54) SUBSTITUTED SPIROCYCLIC CHROMANAMINE COMPOUNDS AS BETA-SECRETASE MODULATORS AND METHODS OF USE

(75) Inventors: Daniel La, Brookline, MA (US); Patricia Lopez, West Hills, CA (US); Vinod F. Patel, Acton, MA (US); Wenge Zhong, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 12/860,595

(22) Filed: Aug. 20, 2010

(65) Prior Publication Data

US 2010/0317668 A1 Dec. 16, 2010

Related U.S. Application Data

(62) Division of application No. 12/291,753, filed on Nov. 12, 2008, now Pat. No. 7,803,809.

(60) Provisional application No. 61/003,164, filed on Nov. 14, 2007.

(51) Int. Cl.
*A61K 31/35* (2006.01)

(52) U.S. Cl. ........ 514/456; 544/238; 544/333; 544/350; 544/405; 546/282.7; 548/159; 548/217; 549/404

(58) Field of Classification Search ................. 514/456; 544/238, 333, 350, 405; 546/282.7; 548/159, 548/217; 549/404
See application file for complete search history.

(56) References Cited

U.S. PATENT DOCUMENTS

| | | | |
|---|---|---|---|
| 5,441,870 | A | 8/1995 | Seubert |
| 5,712,130 | A | 1/1998 | Hajko |
| 5,942,400 | A | 8/1999 | Anderson |
| 2009/0275602 | A1 | 11/2009 | Zhong |

FOREIGN PATENT DOCUMENTS

| | | |
|---|---|---|
| JP | 08099982 A2 | 4/1996 |
| WO | 00/17369 | 3/2000 |
| WO | 01/70672 | 9/2001 |
| WO | 02/02505 | 1/2002 |
| WO | 03/002122 | 1/2003 |
| WO | 03/002518 | 1/2003 |
| WO | 03/006013 | 1/2003 |
| WO | 03/006021 | 1/2003 |
| WO | 03/006423 | 1/2003 |
| WO | 03/029169 | 4/2003 |
| WO | 03/030886 | 4/2003 |
| WO | 03/037325 | 5/2003 |
| WO | 03/040096 | 5/2003 |
| WO | 03/045913 | 6/2003 |
| WO | 03/050073 | 6/2003 |
| WO | 03/057721 | 7/2003 |
| WO | 03/062209 | 7/2003 |
| WO | 03/106405 | 12/2003 |
| WO | 04/000821 | 12/2003 |
| WO | 2004/024081 | 3/2004 |
| WO | 2004/043916 | 5/2004 |
| WO | 2004/050619 | 6/2004 |
| WO | 2004/062625 | 7/2004 |
| WO | 2004/080376 | 9/2004 |
| WO | 2004/080459 | 9/2004 |
| WO | 2004/094384 | 11/2004 |
| WO | 2004/094413 | 11/2004 |
| WO | 2004/099376 | 11/2004 |
| WO | 2005/004802 | 1/2005 |
| WO | 2005/004803 | 1/2005 |
| WO | 2005/005374 | 1/2005 |
| WO | 2007/061930 | 5/2007 |
| WO | 2007/062007 | 5/2007 |

OTHER PUBLICATIONS

Joachim et al., Alz. Dis. Assoc. Dis., 6:7-34 (1992).
Selkoe, Neuron, 6:487 (1991).
Seubert et al., Nature, 359:325-327 (1992).
Citron, Trends in Pharmacological Sciences, 25(2):92-97 (2004).
Sinha et al., Nature, 402:537-554 (1999) (p. 510).
Sabbagh, M. et al., Alz. Dis. Rev. 3:1-19 (1997).
Luo et al., Nature Neuroscience, 4:231-232 (2001).
Yazbeck et al, Org. Process Res. Dev. 2006, 10, p. 655.
Ghosh Aurn K et al ; "Recent Developments of Structure Based Beta-Secretase Inhibitors for Alzheimer's Disease" Current Topics in Medicinal Chemistry, Bentham Science Publishers, Hilversum, NL, vol. 5, No. 16, Jan. 1, 2005, pp. 1609-1622.

*Primary Examiner* — James O Wilson
*Assistant Examiner* — Douglas M Willis
(74) *Attorney, Agent, or Firm* — G. Prabhakar Reddy

(57) ABSTRACT

The present invention comprises a new class of compounds useful for the modulation of Beta-secretase enzyme activity and for the treatment of Beta-secretase mediated diseases, including Alzheimer's disease (AD) and related conditions. In one embodiment, the compounds have a general Formula I

I

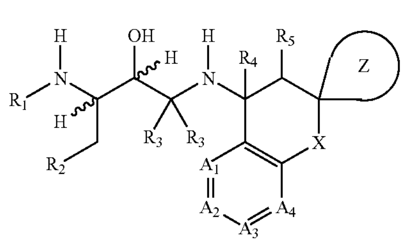

wherein $R^1$, $R^2$, $R^3$, $R^4$, $R^5$, $A^1$, $A^2$, $A^3$, $A^4$, X and Z are defined herein. The invention also includes use of these compounds in pharmaceutical compositions for treatment, prophylactic or therapeutic, of disorders and conditions related to the activity of beta-secretase protein. Such disorders include, for example, Alzheimer's Disease (AD), cognitive deficits and impairment, schizophrenia and other similar central nervous system conditions. The invention also comprises further embodiments of Formula II, intermediates and processes useful for the preparation of compounds of Formulas I and II.

10 Claims, No Drawings

SUBSTITUTED SPIROCYCLIC CHROMANAMINE COMPOUNDS AS BETA-SECRETASE MODULATORS AND METHODS OF USE

RELATED APPLICATIONS

This application is a divisional patent application of, and claims the benefit of, U.S. patent application Ser. No. 12/291,753 filed Nov. 12, 2008, now U.S. Pat. No. 7,803,809, which in turn claims the benefit of U.S. Provisional Application No. 61/003,164, filed 14 Nov. 2007, both specifications of which are hereby incorporated here in by reference in their entireties.

FIELD OF THE INVENTION

The invention relates generally to pharmaceutically active compounds, pharmaceutical compositions and methods of use thereof, to treat Beta-Secretase mediated disorders, including Alzheimer's disease, plaque formation and deposition on the brain and related conditions.

BACKGROUND OF THE INVENTION

Alzheimer's disease (AD) affects greater than 12 million aging people worldwide. AD accounts for the majority of dementia clinically diagnosed after the age of 60. AD is generally characterized by the progressive decline of memory, reasoning, judgment and orientation. As the disease progresses, motor, sensory, and vocal abilities are affected until there is global impairment of multiple cognitive functions. The loss of cognitive function occurs gradually, typically leading to a diminished cognition of one's self, family and friends. Patients with severe cognitive impairment and/or diagnosed as end-stage AD are generally bedridden, incontinent, and dependent on custodial care. After initial diagnosis, the average survival period for the AD patient is only about nine to ten years. Due to the incapacitating, generally humiliating and ultimately fatal effects of AD, there is a need to effectively treat AD upon diagnosis.

AD is characterized by two major physiological changes in the brain. The first change, beta amyloid plaque formation, supports the "amyloid cascade hypothesis" which alleges that AD is caused by the formation of characteristic beta amyloid deposits (commonly referred to as beta amyloid "plaques" or "plaque deposits") in the brain and in cerebral blood vessels (beta amyloid angiopathy). The second change in AD is the formation of intraneuronal tangles, consisting of an aggregate form of the protein tau. Amyloid plaques are thought to be specific for AD, while intraneuronal tangles are also found in other dementia-inducing disorders. Joachim et al., *Alz. Dis. Assoc. Dis.,* 6:7-34 (1992).

It's been hypothesized that beta amyloid protein (also commonly referred to and referred to herein as amyloid-beta peptide or A-beta peptide) formation is a causative precursor or factor in plaque formation and consequently, the development and/or progression of AD. Deposition of A-beta peptide in areas of the brain responsible for areas of cognition, is believed to be a major factor in the development and/or progression of AD. Several lines of evidence indicate that progressive cerebral deposition of beta-amyloid peptide (A-beta) plays a seminal role in the pathogenesis of AD and can precede cognitive symptoms by years or even decades. Selkoe, *Neuron,* 6:487 (1991). Release of A-beta from neuronal cells grown in culture and the presence of A-beta in cerebrospinal fluid (CSF) of both normal individuals and AD patients has been demonstrated. Seubert et al., *Nature,* 359:325-327 (1992). In addition, autopsies of AD patients have revealed large numbers of lesions comprising these 2 factors in areas of the human brain believed to be important for memory and cognition. Smaller numbers of these lesions in a more restricted anatomical distribution are found in the brains of most aged humans who do not have clinical symptoms of AD. Amyloid containing plaques and vascular amyloid angiopathy were also found in the brains of individuals with Down's Syndrome, Hereditary Cerebral Hemorrhage with Amyloidosis of the Dutch-type (HCHWA-D), and other neurodegenerative disorders.

Beta amyloid plaques are primarily composed of amyloid beta peptide (A-beta peptide). A-beta peptide is derived from the proteolytic cleavage of a large transmembrane amyloid precursor protein (APP), and is a peptide ranging in about 39-42 amino acids. A-beta 42 (42 amino acids long) is thought to be the major component of these plaque deposits. Citron, *Trends in Pharmacological Sciences,* 25(2):92-97 (2004). Several aspartyl proteases are thought to be involved in the processing or cleavage of APP, resulting in the formation of A-beta peptide. Beta secretase (BACE, also commonly referred to as memapsin) is thought to first cleave APP to generate two fragments of the A-beta peptide: (1) a first N-terminus fragment and (2) a second C-99 fragment, which is subsequently cleaved by gamma secretase to generate the C-terminus fragment of the A-beta peptide. APP has also found to be cleaved by alpha-secretase to produce alpha-sAPP, a secreted form of APP that does not result in beta-amyloid plaque formation. This alternate pathway precludes the formation of A-beta peptide. A description of the proteolytic processing fragments of APP is found, for example, in U.S. Pat. Nos. 5,441,870, 5,712,130 and 5,942,400.

BACE is an aspartyl protease enzyme comprising 501 amino acids and responsible for processing APP at the beta-secretase specific cleavage site. BACE is present in two forms, BACE 1 and BACE 2, designated as such depending upon the specific cleavage site of APP. Beta secretase is described in Sinha et al., *Nature,* 402:537-554 (1999) (p 510) and PCT application WO 2000/17369. It has been proposed that A-beta peptide accumulates as a result of APP processing by BACE. Moreover, in vivo processing of APP at the beta secretase cleavage site is thought to be a rate-limiting step in A-beta production. Sabbagh, M. et al., *Alz. Dis. Rev.* 3:1-19 (1997). Thus, inhibition of the BACE enzyme activity is thought to be desirable for the treatment of AD.

Studies have shown that the inhibition of BACE may be linked to the treatment of AD. BACE1 knockout mice have failed to produce A-beta, and present a normal phenotype. When crossed with transgenic mice that over express APP, the progeny show reduced amounts of A-beta in brain extracts as compares with control animals (Luo et al., *Nature Neuroscience,* 4:231-232 (2001)). This evidence further supports the concept that inhibition of beta secretase activity and a corresponding reduction of A-beta in the brain should provide a therapeutic method for treating AD and other beta amyloid or plaque related disorders.

Researchers have taken several approaches to treat AD and plaque-related disorders. One approach has been to reduce the formation of plaque on the brain. Particularly, a common approach has been to inhibit the activity of beta secretase. For example, each of the following PCT publications: WO 03/045913, WO 04/043916, WO 03/002122, WO 03/006021, WO 03/002518, WO 04/024081, WO 03/040096, WO 04/050619, WO 04/080376, WO 04/099376, WO 05/004802, WO 04/080459, WO 04/062625, WO 04/042910, WO 05/004803, WO 05/005374, WO 03/106405, WO 03/062209, WO 03/030886, WO 02/002505, WO 01/070671, WO 03/057721, WO 03/006013, WO 03/037325, WO 04/094384, WO 04/094413, WO 03/006423, WO 03/050073, WO 03/029169 and WO 04/000821, describe inhibitors of beta secretase, useful for treating AD and other beta-secretase mediated disorders.

BRIEF SUMMARY OF THE INVENTION

The present invention provides a new class of compounds useful for the modulation of beta secretase activity. To that end, the compounds of the invention are useful for the regulation or reduction of the formation of A-beta peptide and consequently, the reduction of beta amyloid plaque formation on the brain. Accordingly, the compounds are useful for the treatment of Alzheimer's disease and other beta secretase mediated disorders.

The compounds provided by the invention, including stereoisomers, tautomers, solvates, pharmaceutically acceptable salts, derivatives or prodrugs thereof, are generally defined by Formula I

I

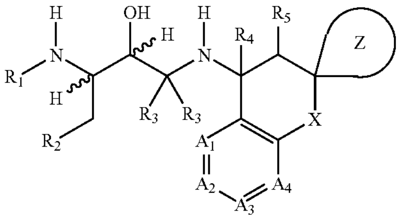

wherein $R^1$, $R^2$, $R^3$, $R^4$, $R^5$, $A^1$, $A^2$, $A^3$, $A^4$, X and Z are as described below. The invention also provides procedures for making compounds of Formula I, as well as intermediates useful in such procedures.

The invention further provides for the use of these compounds for therapeutic, prophylactic, acute and/or chronic treatment of beta secretase mediated diseases, such as those described herein. For example, the compounds are useful for the prophylaxis and treatment of AD and other diseases or conditions involving amyloid plaque formation on the brain.

The invention also provides pharmaceutical compositions, which comprise one or more compounds of the invention, methods for the treatment of beta secretase mediated diseases, such as AD, using the compounds and compositions of the invention, and intermediates and processes useful for the preparation of the compounds of the invention. The invention also provides use of the pharmaceutical composition or medicament, containing one or more of the compounds of the invention, to attenuate, alleviate, or treat disorders through inhibition of beta secretase. For example, and in one embodiment, the invention provides a pharmaceutical composition comprising an effective dosage amount of a compound of Formula I in association with at least one pharmaceutically acceptable excipient.

The foregoing merely summarizes certain aspects of the invention and is not intended, nor should it be construed, as limiting the invention in any way. All patents and other publications recited herein are hereby incorporated by reference in their entirety.

DETAILED DESCRIPTION OF THE INVENTION

In one embodiment of the invention, the compounds, including stereoisomers, tautomers, solvates, pharmaceutically acceptable salts, derivatives or prodrugs thereof, are generally defined by

I

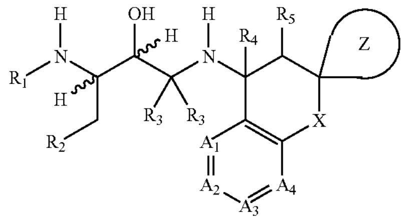

$R^1$ is a partially or fully unsaturated 4-8 membered monocyclic or 6-12 membered bicyclic ring, said ring formed of carbon atoms optionally including 1-3 heteroatoms if monocyclic or 1-6 heteroatoms if bicyclic, said heteroatoms selected from O, N, or S, and wherein said ring is optionally substituted independently with one or more substituents of oxo, $R^7$, $NR^7R^7$, $OR^7$, $SR^7$, $C(O)R^7$, $OC(O)R^7$, $COOR^7$, $C(O)NR^7R^7$, $NR^7C(O)R^7$, $NR^7C(O)NR^7R^7$, $NR^7(COOR^7)$, $OC(O)NR^7R^7$, $S(O)_2NR^7R^7$, $NR^7S(O)_2NR^7R^7$ or $NR^7S(O)_2R^7$;

$R^2$ is a partially or fully saturated or fully unsaturated 3-8 membered monocyclic or 6-12 membered bicyclic ring, said ring formed of carbon atoms optionally including 1-3 heteroatoms if monocyclic or 1-6 heteroatoms if bicyclic, said heteroatoms selected from O, N, or S, and wherein said ring is optionally substituted independently with one or more substituents of oxo, $R^7$, $NR^7R^7$, $OR^7$, $SR^7$, $C(O)R^7$, $OC(O)R^7$, $COOR^7$, $C(O)NR^7R^7$, $NR^7C(O)R^7$, $NR^7C(O)NR^7R^7$, $NR^7(COOR^7)$, $OC(O)NR^7R^7$, $S(O)_2NR^7R^7$, $NR^7S(O)_2NR^7R^7$ or $NR^7S(O)_2R^7$;

each $R^3$, independently, is H, haloalkyl, CN, $C_{1-6}$-alkyl, $C_{2-8}$-alkenyl, $C_{2-8}$-alkynyl, $C_{3-8}$-cycloalkyl or $C_{4-8}$-cycloalkenyl, each of the $C_{1-6}$-alkyl, $C_{2-8}$-alkenyl, $C_{2-8}$-alkynyl, $C_{3-8}$-cycloalkyl and $C_{4-8}$-cycloalkenyl optionally comprising 1-2 heteroatoms selected from N, O and S and optionally substituted with 1-5 substituents of $R^7$;

$R^4$ is H, halo or $C_{1-6}$-alkyl;

$R^5$ is H, halo, haloalkyl, oxo, $C_{1-6}$-alkyl, —O—$C_{1-6}$-alkyl, —S—$C_{1-6}$-alkyl, —NH—$C_{1-6}$alkyl, —N-di-$C_{1-6}$-alkyl, CN, OH or $NH_2$, wherein the $C_{1-6}$-alkyl and the $C_{1-6}$-alkyl portion of —O—$C_{1-6}$-alkyl, —S—$C_{1-6}$-alkyl, —NH—$C_{1-6}$-alkyl and —N-di-$C_{1-6}$-alkyl are optionally substituted independently with 1-5 substituents of $R^7$;

each of $A^1$, $A^2$, $A^3$ and $A^4$, independently, is N, CH or $CR^6$, provided that no more than two of $A^1$, $A^2$, $A^3$ and $A^4$ is N;

X is $CHR^6$, $CR^6R^6$, C(═O), O, $NR^6$, or $S(O)_o$ wherein o is 0, 1 or 2;

Z is a 3-6 membered spirocyclic ring formed of carbon atoms optionally including 1-3 heteroatoms selected from O, N and S and optionally substituted independently with 1-3 substituents of $R^7$;

each $R^6$, independently, is halo, haloalkyl, $C_{1-6}$-alkyl, —O—$C_{1-6}$-alkyl, —S—$C_{1-6}$-alkyl, —NH—$C_{1-6}$-alkyl, —N-di-$C_{1-6}$-alkyl, CN, OH, $NH_2$, $C_{2-6}$-alkenyl, $C_{2-6}$-alkynyl, $C_{3-8}$-cycloalkyl or $C_{4-8}$-cycloalkenyl, wherein the $C_{1-6}$-alkyl, $C_{2-6}$-alkenyl, $C_{2-6}$-alkynyl, $C_{3-8}$—cycloalkyl, $C_{4-8}$-cycloalkenyl and the $C_{1-6}$-alkyl portion of —O—$C_{1-6}$-alkyl, —S—$C_{1-6}$-alkyl, —NH—$C_{1-6}$-alkyl and —N-di-$C_{1-6}$-alkyl are optionally substituted with 1-5 substituents of $R^7$;

or $R^6$ is a fully unsaturated or partially or fully unsaturated 5- or 6-membered monocyclic or bicyclic ring formed of carbon atoms, said ring optionally including 1-5 heteroatoms selected from O, N, or S and optionally substituted with one or more substituents of $R^7$; and each $R^7$, independently, is H, halo, haloalkyl, CN, OH, $NO_2$, $NH_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a fully saturated or partially or fully unsaturated 3-8 membered monocyclic or a 6-12 membered bicyclic ring, said ring formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl.

The compound of claim 1 wherein $R^1$ is an optionally substituted ring selected from phenyl, naphthyl, pyridyl, pyrimidyl, pyridazinyl, pyrazinyl, triazinyl, quinolinyl, isoquinolinyl, quinazolinyl, isoquinazolinyl, phthalazinyl, thiophenyl, thienopyrimidinyl, thienopyridinyl, furyl, pyrrolyl, pyrazolyl, pyrazolopyridinyl, pyrazoliopyrimidinyl, imidazolyl, triazolyl, triazolopyrazinyl, triazolopyridinyl, tetrazolyl, thiazolyl, oxazolyl, isoxazolyl, isothiazolyl, thiadiazolyl, oxadiazolyl, indolyl, isoindolyl, benzofuranyl, benzothiophenyl, benzimidazolyl, benzoxazolyl, benzisoxazolyl, benzothiazolyl, benzoisothiazolyl, benzotriazolyl, tetrahydrofuranyl, pyrrolidinyl, oxazolinyl, isoxazolinyl, thiazolinyl, pyrazolinyl and benzodioxolyl.

In another embodiment of the invention, the compounds of Formula I include compounds wherein $A^1$ is N, in conjunction with any of the above or below embodiments.

In another embodiment of the invention, the compounds of Formula I include compounds wherein $A^1$ is CH, in conjunction with any of the above or below embodiments.

In another embodiment of the invention, the compounds of Formula I include compounds wherein $A^1$ is $CR^6$ in conjunction with any of the above or below embodiments.

In another embodiment of the invention, the compounds of Formula I include compounds wherein $A^2$ is N, in conjunction with any of the above or below embodiments.

In another embodiment of the invention, the compounds of Formula I include compounds wherein $A^2$ is CH, in conjunction with any of the above or below embodiments.

In another embodiment of the invention, the compounds of Formula I include compounds wherein $A^2$ is $CR^6$, in conjunction with any of the above or below embodiments.

In another embodiment of the invention, the compounds of Formula I include compounds wherein each of $A^1$ and $A^2$, independently, is CH in conjunction with any of the above or below embodiments.

In another embodiment of the invention, the compounds of Formula I include compounds wherein each of $A^1$, $A^2$, $A^3$ and $A^4$, independently, is CH in conjunction with any of the above or below embodiments.

In another embodiment of the invention, the compounds of Formula I include compounds wherein each of $A^1$ and $A^2$, independently, is $CR^6$ in conjunction with any of the above or below embodiments.

In another embodiment of the invention, the compounds of Formula I include compounds wherein one of $A^1$ and $A^2$, independently, is N and the other of one of $A^1$ and $A^2$, independently, is $CR^6$ in conjunction with any of the above or below embodiments.

In another embodiment of the invention, the compounds of Formula I include compounds wherein one of $A^1$ is CH and one of $A^2$, $A^3$ and $A^4$, independently, is N and the other three of $A^2$, $A^3$ and $A^4$, independently, is CH or $CR^6$ in conjunction with any of the above or below embodiments.

In another embodiment of the invention, the compounds of Formula I include compounds wherein one of $A^1$, $A^2$, $A^3$ and $A^4$, independently, is N and the other three of $A^1$, $A^2$, $A^3$ and $A^4$, independently, is CH or $CR^6$ in conjunction with any of the above or below embodiments.

In another embodiment of the invention, the compounds of Formula I include compounds wherein $R^1$ is a partially or fully unsaturated 4-8 membered monocyclic or 6-12 membered bicyclic ring, said ring formed of carbon atoms optionally including 1-3 heteroatoms if monocyclic or 1-6 heteroatoms if bicyclic, said heteroatoms selected from O, N, or S, and wherein said ring is optionally substituted independently with one or more substituents of oxo, $R^7$, $NR^7R^7$, $OR^7$, $SR^7$, $C(O)R^7$, $OC(O)R^7$, $COOR^7$, $C(O)NR^7R^7$, $NR^7C(O)R^7$, $NR^7C(O)NR^7R^7$, $NR^7(COOR^7)$, $OC(O)NR^7R^7$, $S(O)_2NR^7R^7$, $NR^7S(O)_2NR^7R^7$ or $NR^7S(O)_2R^7$, in conjunction with any of the above or below embodiments.

In another embodiment of the invention, the compounds of Formula I include compounds wherein $R^1$ is a ring selected from phenyl, naphthyl, pyridyl, pyrimidyl, pyridazinyl, pyrazinyl, triazinyl, quinolinyl, isoquinolinyl, quinazolinyl, isoquinazolinyl, phthalazinyl, thiophenyl, thienopyrimidinyl, thienopyridinyl, furyl, pyrrolyl, pyrazolyl, pyrazolopyridinyl, pyrazolopyrimidinyl, imidazolyl, triazolyl, triazolopyrazinyl, triazolopyridinyl, tetrazolyl, thiazolyl, oxazolyl, isoxazolyl, isothiazolyl, thiadiazolyl, oxadiazolyl, indolyl, isoindolyl, benzofuranyl, benzothiophenyl, benzimidazolyl, benzoxazolyl, benzisoxazolyl, benzothiazolyl, benzoisothiazolyl, benzotriazolyl, tetrahydrofuranyl, pyrrolidinyl, oxazolinyl, isoxazolinyl, thiazolinyl, pyrazolinyl and benzodioxolyl, said ring optionally substituted with 1-5 substituents of $R^7$, in conjunction with any of the above or below embodiments.

In another embodiment of the invention, the compounds of Formula I include compounds wherein $R^1$ is a ring selected from phenyl, pyridyl, pyrimidyl, pyridazinyl, pyrazinyl, thiophenyl, thienopyrimidinyl, thienopyridinyl, furyl, pyrazolyl, pyrazolopyridinyl, pyrazolopyrimidinyl, imidazolyl, triazolopyrazinyl, triazolopyridinyl, thiazolyl, oxazolyl, isoxazolyl, isothiazolyl, thiadiazolyl, oxadiazolyl, indolyl, isoindolyl, benzimidazolyl, benzoxazolyl, benzisoxazolyl, benzothiazolyl, benzoisothiazolyl and benzodioxolyl, said ring optionally substituted with 1-5 substituents of $R^7$, in conjunction with any of the above or below embodiments.

In another embodiment of the invention, the compounds of Formula I include compounds wherein $R^2$ is a partially or fully saturated or fully unsaturated 3-8 membered monocyclic or 6-12 membered bicyclic ring, said ring formed of carbon atoms optionally including 1-3 heteroatoms if monocyclic or 1-6 heteroatoms if bicyclic, said heteroatoms selected from O, N, or S, and wherein said ring is optionally substituted independently with one or more substituents of oxo, $R^7$, $NR^7R^7$, $OR^7$, $SR^7$, $C(O)R^7$, $OC(O)R^7$, $COOR^7$, $C(O)NR^7R^7$, $NR^7C(O)R^7$, $NR^7C(O)NR^7R^7$, $NR^7(COOR^7)$, $OC(O)NR^7R^7$, $S(O)_2NR^7R^7$, $NR^7S(O)_2NR^7R^7$ or $NR^7S(O)_2R^7$, in conjunction with any of the above or below embodiments.

In another embodiment of the invention, the compounds of Formula I include compounds wherein $R^2$ is phenyl, naphthyl, pyridyl, pyrimidyl, pyridazinyl, pyrazinyl, triazinyl, quinolinyl, isoquinolinyl, quinazolinyl, isoquinazolinyl, phthalazinyl, thiophenyl, furyl, pyrrolyl, pyrazolyl, imidazolyl, triazolyl, tetrazolyl, thiazolyl, oxazolyl, isoxazolyl, isothiazolyl, thiadiazolyl, oxadiazolyl, indolyl, isoindolyl, benzofuranyl, benzothiophenyl, benzimidazolyl, benzoxazolyl, benzisoxazolyl, benzothiazolyl, benzoisothiazolyl, benzotriazolyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, benzodioxolyl, cyclopropyl, cyclobutyl, cyclopentyl, cyclohexyl or cycloheptyl, each of is optionally substituted independently with one or more substituents of oxo, $R^7$, $NR^7R^7$, $OR^7$, $SR^7$, $C(O)R^7$, $OC(O)R^7$, $COOR^7$, $C(O)NR^7R^7$, $NR^7C(O)R^7$, $NR^7C(O)NR^7R^7$, $NR^7(COOR^7)$, $OC(O)NR^7R^7$, $S(O)_2NR^7R^7$, $NR^7S(O)_2NR^7R^7$ or $NR^7S(O)_2R^7$, in conjunction with any of the above or below embodiments.

In another embodiment of the invention, the compounds of Formula I include compounds wherein $R^2$ is an optionally substituted ring selected from phenyl, naphthyl, pyridyl, pyrimidyl, pyridazinyl, pyrazinyl, triazinyl, quinazolinyl, isoquinazolinyl, phthalazinyl, thiophenyl, furyl, pyrrolyl, pyrazolyl, imidazolyl, triazolyl, tetrazolyl, thiazolyl, oxazolyl, isoxazolyl, isothiazolyl, thiadiazolyl, oxadiazolyl, indolyl, isoindolyl, benzofuranyl, benzothiophenyl, benzimidazolyl, benzoxazolyl, benzisoxazolyl, benzothiazolyl, benzoisothiazolyl, benzotriazolyl, tetrahydrofuranyl, pyrrolidinyl, oxazolinyl, isoxazolinyl, thiazolinyl, pyrazolinyl, morpholinyl, piperidinyl, piperazinyl, pyranyl, benzodioxolyl, cyclopropyl, cyclobutyl, cyclopentyl, cyclohexyl and cycloheptyl, in conjunction with any of the above or below embodiments.

In another embodiment of the invention, the compounds of Formula I include compounds wherein $R^2$ is phenyl, pyridyl, pyrimidyl, pyridazinyl, pyrazinyl, triazinyl, thiophenyl, furyl, pyrrolyl, pyrazolyl, imidazolyl, triazolyl, tetrazolyl, thiazolyl, oxazolyl, isoxazolyl, isothiazolyl, thiadiazolyl, oxadiazolyl, indolyl, isoindolyl, benzofuranyl, benzimidazolyl, pyrrolidinyl or benzodioxolyl, each of is optionally substituted independently with one or more substituents of oxo, $R^7$, $NR^7R^7$, $OR^7$, $SR^7$, $C(O)R^7$, $OC(O)R^7$, $COOR^7$, $C(O)NR^7R^7$, $NR^7C(O)R^7$, $NR^7C(O)NR^7R^7$, $NR^7(COOR^7)$, $OC(O)NR^7R^7$, $S(O)_2NR^7R^7$, $NR^7S(O)_2NR^7R^7$ or $NR^7S(O)_2R^7$, in conjunction with any of the above or below embodiments.

In another embodiment of the invention, the compounds of Formula I include compounds wherein $R^2$ is phenyl or benzodioxolyl, each of is optionally substituted independently with one or more substituents of oxo, $R^7$, $NR^7R^7$, $OR^7$, $SR^7$, $C(O)R^7$, $OC(O)R^7$, $COOR^7$, $C(O)NR^7R^7$, $NR^7C(O)R^7$, $NR^7C(O)NR^7R^7$, $NR^7(COOR^7)$, $OC(O)NR^7R^7$, $S(O)_2NR^7R^7$, $NR^7S(O)_2NR^7R^7$ or $NR^7S(O)_2R^7$, in conjunction with any of the above or below embodiments.

In another embodiment of the invention, the compounds of Formula I include compounds wherein $R^2$ is phenyl optionally substituted with 1-5 substituents of halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{1-10}$-alkylamino-, $C_{1-10}$-dialkylamino-, $C_{1-10}$-alkoxyl or a ring selected from phenyl, pyridyl, pyrimidyl, pyridazinyl, pyrazinyl, triazinyl, thiophenyl, furyl, pyrrolyl, pyrazolyl, imidazolyl, triazolyl, tetrazolyl, thiazolyl, oxazolyl, isoxazolyl, isothiazolyl, thiadiazolyl, oxadiazolyl, pyrrolidinyl, oxazolinyl, isoxazolinyl, thiazolinyl, pyrazolinyl, morpholinyl, piperidinyl, piperazinyl and pyranyl, said ring optionally substituted with 1-5 substituents of $R^7$, in conjunction with any of the above or below embodiments.

In another embodiment of the invention, the compounds of Formula I include compounds wherein each $R^3$, independently, is H, haloalkyl, CN, $C_{1-6}$-alkyl, $C_{2-8}$-alkenyl, $C_{2-8}$-alkynyl, $C_{3-8}$-cycloalkyl or $C_{4-8}$-cycloalkenyl, each of the $C_{1-6}$-alkyl, $C_{2-8}$-alkenyl, $C_{2-8}$-alkynyl, $C_{3-8}$-cycloalkyl and $C_{4-8}$-cycloalkenyl optionally comprising 1-2 heteroatoms selected from N, O and S and optionally substituted with 1-5 substituents of $R^7$, in conjunction with any of the above or below embodiments.

In another embodiment of the invention, the compounds of Formula I include compounds wherein each $R^3$, independently, is H, haloalkyl, CN, $C_{1-10}$-alkyl, $C_{2-10}$-alkenyl or $C_{2-10}$-alkynyl, in conjunction with any of the above or below embodiments.

In another embodiment of the invention, the compounds of Formula I include compounds wherein each $R^3$, independently, is H, haloalkyl or $C_{1-10}$-alkyl, in conjunction with any of the above or below embodiments.

In another embodiment of the invention, the compounds of Formula I include compounds wherein each $R^3$, independently, is H, in conjunction with any of the above or below embodiments.

In another embodiment of the invention, the compounds of Formula I include compounds wherein each of $A^1$ and $A^2$, independently, is CH;

one of $A^3$ and $A^4$ is N and the other of $A^3$ and $A^4$ is CH or $CR^6$;

$R^1$ is a ring selected from phenyl, naphthyl, pyridyl, pyrimidyl, pyridazinyl, pyrazinyl, triazinyl, quinolinyl, isoquinolinyl, quinazolinyl, isoquinazolinyl, phthalazinyl, thiophenyl, thienopyrimidinyl, thienopyridinyl, furyl, pyrrolyl, pyrazolyl, pyrazolopyridinyl, pyrazoliopyrimidinyl, imidazolyl, triazolyl, triazolopyrazinyl, triazolopyridinyl, tetrazolyl, thiazolyl, oxazolyl, isoxazolyl, isothiazolyl, thiadiazolyl, oxadiazolyl, indolyl, isoindolyl, benzofuranyl, benzothiophenyl, benzimidazolyl, benzoxazolyl, benzisoxazolyl, benzothiazolyl, benzoisothiazolyl, benzotriazolyl, tetrahydrofuranyl, pyrrolidinyl, oxazolinyl, isoxazolinyl, thiazolinyl, pyrazolinyl and benzodioxolyl, said ring optionally substituted with 1-5 substituents of $R^7$;

$R^2$ is a ring selected from phenyl, pyridyl, pyrimidyl, pyridazinyl, pyrazinyl, triazinyl, thiophenyl, furyl, pyrrolyl, pyrazolyl, imidazolyl, triazolyl, tetrazolyl, thiazolyl, oxazolyl, isoxazolyl, isothiazolyl, thiadiazolyl, oxadiazolyl, pyrrolidinyl, oxazolinyl, isoxazolinyl, thiazolinyl, pyrazolinyl, morpholinyl, piperidinyl, piperazinyl and pyranyl, said ring optionally substituted with 1-5 substituents of $R^7$;

each $R^3$, independently, is H;

$R^4$ is H or $C_{1-4}$-alkyl;

$R^5$ is H, halo, haloalkyl, $C_{1-6}$-alkyl, —O—$C_{1-6}$-alkyl, —S—$C_{1-6}$-alkyl, —NH—$C_{1-6}$-alkyl, —N-di-$C_{1-6}$-alkyl, CN, OH or $NH_2$;

X is $CHR^6$, C(═O) or O;

Z is a cyclopropyl, cyclobutyl or cyclopentyl ring wherein 0, 1 or 2 carbon atoms of the ring are, independently, replaced with an oxygen atom and the ring optionally substituted independently with 1-5 substituents of $R^7$; and each $R^6$, independently, is halo, haloalkyl, $C_{1-6}$-alkyl, —O—$C_{1-6}$-alkyl, —S—$C_{1-6}$-alkyl, —NH—$C_{1-6}$-alkyl, N-di-$C_{1-6}$-alkyl, CN, OH, $NH_2$, $C_{2-6}$-alkenyl, $C_{2-6}$-alkynyl, $C_{3-8}$-cycloalkyl, $C_{4-8}$-cycloalkenyl or $R^6$ is a fully unsaturated or partially or fully unsaturated 5- or 6-membered monocyclic or bicyclic ring formed of carbon atoms, said ring optionally including 1-5 heteroatoms selected from O, N, or S wherein said $C_{1-6}$-alkyl, $C_{2-6}$-alkenyl, $C_{2-6}$-alkynyl, $C_{3-8}$-cycloalkyl, $C_{4-8}$-cycloalkenyl, the $C_{1-6}$-alkyl portion of —O—$C_{1-6}$-alkyl, —S—$C_{1-6}$-alkyl, —NH—$C_{1-6}$-alkyl and —N-di-$C_{1-6}$-alkyl and ring are optionally substituted with 1-5 substituents of $R^7$, in conjunction with any of the above or below embodiments.

In another embodiment of the invention, there are provided compounds, including stereoisomers, tautomers, solvates, pharmaceutically acceptable salts, derivatives or prodrugs thereof, generally defined by Formula II

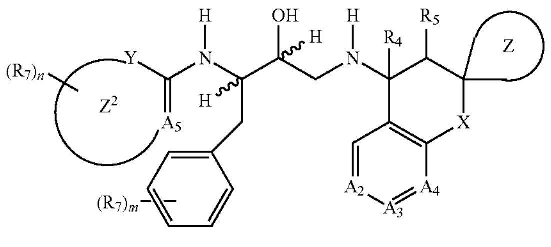

II wherein one of $A^2$, $A^3$ and $A^4$ is N and the other of $A^2$, $A^3$ and $A^4$ is CH or $CR^6$;

$A^5$ is CH or N;

$R^4$ is H, halo or $C_{1-6}$-alkyl;

$R^5$ is H, halo, haloalkyl, $C_{1-6}$-alkyl, —O—$C_{1-6}$-alkyl, —S—$C_{1-6}$-alkyl, —NH—$C_{1-6}$-alkyl, —N-di-$C_{1-6}$-alkyl, CN, OH or $NH_2$, wherein the $C_{1-6}$-alkyl and the $C_{1-6}$-alkyl portion of —O—$C_{1-6}$-alkyl, —NH—$C_{1-6}$-alkyl and —N-di-$C_{1-6}$-alkyl are optionally substituted independently with 1-5 substituents of $R^7$;

X is $CHR^6$, C(═O) or O;

Y is $CR^7R^7$, N, $NR^7$, S or O;

Z is a cyclopropyl, cyclobutyl or cyclopentyl ring wherein 0, 1 or 2 carbon atoms of the ring are, independently, replaced with an oxygen atom and the ring optionally substituted independently with 1-5 substituents of $R^7$;

$Z^2$ taken together with the carbon atom to which $A^5$ and Y are attached is a 4-, 5- or 6-membered monocylic ring or a 8-, 9- or 10-membered bicyclic ring, said ring formed of carbon atoms optionally including 1-3 heteroatoms if monocylic or 1-5 heteroatoms if bicyclic, said heteroatoms selected from N, O and S, and said ring optionally substituted with 1-5 substituents of $R^7$;

each $R^6$, independently, is halo, haloalkyl, $C_{1-6}$-alkyl, —O—$C_{1-6}$-alkyl, —S—$C_{1-6}$-alkyl, —NH—$C_{1-6}$-alkyl, —N-di-$C_{1-6}$-alkyl, CN, OH, $NH_2$, $C_{2-6}$-alkenyl, $C_{2-6}$-alkynyl, $C_{3-8}$-cycloalkyl, $C_{4-8}$-cycloalkenyl or $R^6$ is a fully unsaturated or partially or fully unsaturated 5- or 6-membered monocyclic or bicyclic ring formed of carbon atoms, said ring optionally including 1-5 heteroatoms selected from O, N, or S wherein said $C_{1-6}$-alkyl, $C_{2-6}$-alkenyl, $C_{2-6}$-alkynyl, $C_{3-8}$-cycloalkyl, $C_{4-8}$-cycloalkenyl, the $C_{1-6}$-alkyl portion of —O—$C_{1-6}$-alkyl, —S—$C_{1-6}$-alkyl, —NH—$C_{1-6}$-alkyl and —N-di-$C_{1-6}$-alkyl and ring are optionally substituted with 1-5 substituents of $R^7$;

each $R^7$, independently, is H, halo, haloalkyl, CN, OH, $NO_2$, $NH_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a fully saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;

m is 0, 1, 2, 3 or 4; and n is 0, 1, 2, 3, 4 or 5.

In another embodiment of the invention, the compounds of Formula II include compounds wherein ring $Z^2$ is a partially or fully unsaturated 4-8 membered monocyclic or 6-12 membered bicyclic ring, said ring formed of carbon atoms optionally including 1-3 heteroatoms if monocyclic or 1-6 heteroatoms if bicyclic, said heteroatoms selected from O, N, or S, and wherein said ring is optionally substituted independently with one or more substituents of oxo, $R^7$, $NR^7R^7$, $OR^7$, $SR^7$, $C(O)R^7$, $OC(O)R^7$, $COOR^7$, $C(O)NR^7R^7$, $NR^7C(O)R^7$, $NR^7C(O)NR^7R^7$, $NR^7(COOR^7)$, $OC(O)NR^7R^7$, $S(O)_2NR^7R^7$, $NR^7S(O)_2NR^7R^7$ or $NR^7S(O)_2R^7$, in conjunction with any of the above or below embodiments.

In another embodiment of the invention, the compounds of Formula II include compounds wherein $Z^2$ is a ring selected from phenyl, naphthyl, pyridyl, pyrimidyl, pyridazinyl, pyrazinyl, triazinyl, quinolinyl, isoquinolinyl, quinazolinyl, isoquinazolinyl, phthalazinyl, thiophenyl, thienopyrimidinyl, thienopyridinyl, furyl, pyrrolyl, pyrazolyl, pyrazolopyridinyl, pyrazolopyrimidinyl, imidazolyl, triazolyl, triazolopyrazinyl, triazolopyridinyl, tetrazolyl, thiazolyl, oxazolyl, isoxazolyl, isothiazolyl, thiadiazolyl, oxadiazolyl, indolyl, isoindolyl, benzofuranyl, benzothiophenyl, benzimidazolyl, benzoxazolyl, benzisoxazolyl, benzothiazolyl, benzoisothiazolyl, benzotriazolyl, tetrahydrofuranyl, pyrrolidinyl, oxazolinyl, isoxazolinyl, thiazolinyl, pyrazolinyl, cyclobutene and benzodioxolyl, said ring optionally substituted with 1-5 substituents of $R^7$, in conjunction with any of the above or below embodiments.

In another embodiment of the invention, the compounds of Formula II include compounds wherein ring $Z^2$ is a ring selected from phenyl, pyridyl, pyrimidyl, pyridazinyl, pyrazinyl, thiophenyl, thienopyrimidinyl, thienopyridinyl, furyl, pyrazolyl, pyrazolopyridinyl, pyrazolopyrimidinyl, imidazolyl, triazolopyrazinyl, triazolopyridinyl, thiazolyl, oxazolyl, isoxazolyl, isothiazolyl, thiadiazolyl, oxadiazolyl, indolyl, isoindolyl, benzimidazolyl, benzoxazolyl, benzisoxazolyl, benzothiazolyl, benzoisothiazolyl and benzodioxolyl, said ring optionally substituted with 1-5 substituents of $R^7$, in conjunction with any of the above or below embodiments.

In another embodiment of the invention, the compounds of Formula II include compounds wherein $A^5$ is CH or N, in conjunction with any of the above or below embodiments.

In another embodiment of the invention, the compounds of Formula II include compounds wherein $A^5$ is N, in conjunction with any of the above or below embodiments.

In another embodiment of the invention, the compounds of Formula II include compounds wherein $A^5$ is CH, in conjunction with any of the above or below embodiments.

In another embodiment of the invention, the compounds of Formula II include compounds wherein Y is $CR^7R^7$, $NR^7$, S or O, in conjunction with any of the above or below embodiments.

In another embodiment of the invention, the compounds of Formula II include compounds wherein Y is $CR^7R^7$, in conjunction with any of the above or below embodiments.

In another embodiment of the invention, the compounds of Formula II include compounds wherein Y is $CHR^7$ NH, S or O, in conjunction with any of the above or below embodiments.

In another embodiment of the invention, the compounds of Formula II include compounds wherein Y is $NR^7$, in conjunction with any of the above or below embodiments.

In another embodiment of the invention, the compounds of Formula II include compounds wherein Y is S or O, in conjunction with any of the above or below embodiments.

In another embodiment of the invention, the compounds of Formulas I or II include compounds wherein ring Z is

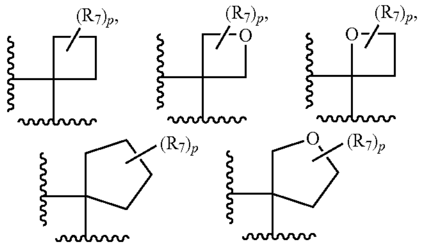

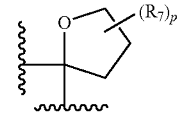

or

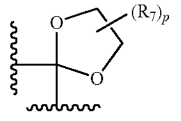

and wherein $R^7$ is H, halo, haloalkyl, CN, OH, $NO_2$, $NH_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a fully saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl, and p is 0, 1, 2, 3 or 4, in conjunction with any of the above or below embodiments.

In another embodiment of the invention, the compounds of Formulas I or II include compounds wherein $R^4$ is H, halo or $C_{1-6}$-alkyl, in conjunction with any of the above or below embodiments.

In another embodiment of the invention, the compounds of Formulas I or II include compounds wherein $R^4$ is H or $C_{1-6}$-alkyl, in conjunction with any of the above or below embodiments.

In another embodiment of the invention, the compounds of Formulas I or II include compounds wherein $R^4$ is H, in conjunction with any of the above or below embodiments.

In another embodiment of the invention, the compounds of Formulas I or II include compounds wherein $R^5$ is H, halo, haloalkyl, oxo, —S—$C_{1-6}$-alkyl, —NH—$C_{1-6}$alkyl, —N-di-$C_{1-6}$-alkyl, acetyl, CN, OH or $NH_2$, wherein the $C_{1-6}$-alkyl and the $C_{1-6}$-alkyl portion of —O—$C_{1-6}$-alkyl, —S—$C_{1-6}$-alkyl, —NH—$C_{1-6}$-alkyl and —N-di-$C_{1-6}$-alkyl are optionally substituted independently with 1-5 substituents of $R^7$, in conjunction with any of the above or below embodiments.

In another embodiment of the invention, the compounds of Formulas I or II include compounds wherein $R^5$ is H, halo, haloalkyl, $C_{1-6}$-alkyl, —O—$C_{1-6}$-alkyl, —S—$C_{1-6}$-alkyl, —NH—$C_{1-6}$-alkyl, —N-di-$C_{1-6}$-alkyl, acetyl, CN, OH or $NH_2$, in conjunction with any of the above or below embodiments.

In another embodiment of the invention, the compounds of Formulas I or II include compounds wherein $R^5$ is H, halo, haloalkyl, $C_{1-6}$-alkyl, —O—$C_{1-6}$-alkyl, —NH—$C_{1-6}$-alkyl, CN or OH, in conjunction with any of the above or below embodiments.

In another embodiment of the invention, the compounds of Formulas I or II include compounds wherein $R^5$ is H, in conjunction with any of the above or below embodiments.

In another embodiment of the invention, the compounds of Formulas I or II include compounds wherein $A^3$ is N, in conjunction with any of the above or below embodiments.

In another embodiment of the invention, the compounds of Formulas I or II include compounds wherein $A^3$ is CH, in conjunction with any of the above or below embodiments.

In another embodiment of the invention, the compounds of Formulas I or II include compounds wherein $A^3$ is $CR^6$ in conjunction with any of the above or below embodiments.

In another embodiment of the invention, the compounds of Formulas I or II include compounds wherein $A^4$ is N, in conjunction with any of the above or below embodiments.

In another embodiment of the invention, the compounds of Formulas I or II include compounds wherein $A^4$ is CH, in conjunction with any of the above or below embodiments.

In another embodiment of the invention, the compounds of Formulas I or II include compounds wherein $A^4$ is $CR^6$, in conjunction with any of the above or below embodiments.

In another embodiment of the invention, the compounds of Formulas I or II include compounds wherein each of $A^3$ and $A^4$, independently, is CH in conjunction with any of the above or below embodiments.

In another embodiment of the invention, the compounds of Formulas I or II include compounds wherein each of $A^3$ and $A^4$, independently, is $CR^6$ in conjunction with any of the above or below embodiments.

In another embodiment of the invention, the compounds of Formulas I or II include compounds wherein one of $A^3$ and $A^4$, independently, is N and the other one of $A^3$ and $A^4$, independently, is $CR^6$ in conjunction with any of the above or below embodiments.

In another embodiment of the invention, the compounds of Formulas I or II include compounds wherein one of $A^3$ and $A^4$, independently, is N and the other one of $A^3$ and $A^4$, independently, is CH in conjunction with any of the above or below embodiments.

In another embodiment of the invention, the compounds of Formulas I or II include compounds wherein X is $CHR^6$, $CR^6R^6$, C(=O), O, $NR^6$, or $S(O)_o$ wherein o is 0, 1 or 2, in conjunction with any of the above or below embodiments.

In another embodiment of the invention, the compounds of Formulas I or II include compounds wherein X is $CHR^6$, in conjunction with any of the above or below embodiments.

In another embodiment of the invention, the compounds of Formulas I or II include compounds wherein X is $CR^6R^6$, in conjunction with any of the above or below embodiments.

In another embodiment of the invention, the compounds of Formulas I or II include compounds wherein X is C(=O), in conjunction with any of the above or below embodiments.

In another embodiment of the invention, the compounds of Formulas I or II include compounds wherein X is O, in conjunction with any of the above or below embodiments.

In another embodiment of the invention, the compounds of Formulas I or II include compounds wherein X is $NR^6$, in conjunction with any of the above or below embodiments.

In another embodiment of the invention, the compounds of Formulas I or II include compounds wherein X is $S(O)_o$ wherein o is 0, 1 or 2, in conjunction with any of the above or below embodiments.

In another embodiment of the invention, the compounds of Formulas I or II include compounds wherein X is $CHR^6$, O or $NR^6$, in conjunction with any of the above or below embodiments.

In another embodiment of the invention, the compounds of Formulas I or II include compounds wherein X is $CHR^6$, C(═O) or O, in conjunction with any of the above or below embodiments.

In another embodiment of the invention, the compounds of Formulas I or II include compounds wherein ring Z is a 3-6 membered spirocyclic ring formed of carbon atoms optionally including 1-3 heteroatoms selected from O, N and S and optionally substituted independently with 1-3 substituents of $R^7$, in conjunction with any of the above or below embodiments.

In another embodiment of the invention, the compounds of Formulas I or II include compounds wherein ring Z is a cyclopropyl, cyclobutyl or cyclopentyl ring wherein 0, 1 or 2 carbon atoms of the ring are, independently, replaced with an oxygen atom and the ring optionally substituted independently with 1-5 substituents of $R^7$, in conjunction with any of the above or below embodiments.

In another embodiment, the invention provides each of the Exemplary compounds, and stereoisomers, tautomers, solvates, pharmaceutically acceptable salts, derivatives or prodrugs thereof, and synthetic intermediates at each step of the process of making compounds of Formulas I or II, which are generally described herein.

Definitions

The following definitions should assist in understanding the invention described herein.

The term "comprising" is meant to be open ended, i.e., all encompassing and non-limiting. Comprising is intended to include each and every indicated component while not excluding any other components or elements.

The term "$C_{\alpha-\beta}$alkyl", when used either alone or within other terms such as "haloalkyl" and "alkylamino", embraces linear or branched radicals having α to β number of carbon atoms (such as $C_1$-$C_{10}$). One or more carbon atoms of the "alkyl" radical may be substituted, such as with a cycloalkyl moeity. Examples of "alkyl" radicals include methyl, cyclopropylmethyl, cyclobutylmethyl, cyclopentylmethyl, ethyl, cyclopropylethyl, cyclobutylethyl, cyclopentylethyl, n-propyl, isopropyl, n-butyl, cyclopropylbutyl, isobutyl, sec-butyl, tert-butyl, pentyl, isoamyl, hexyl and the like. The term "alkylenyl" embraces bridging divalent alkyl radicals such as methylenyl and ethylenyl.

The term "alkenyl", when used alone or in combination, embraces linear or branched radicals having at least one carbon-carbon double bond in a moiety having between two and ten carbon atoms. Included within alkenyl radicals are "lower alkenyl" radicals having two to about six carbon atoms and, for example, those radicals, having two to about four carbon atoms. Examples of alkenyl radicals include, without limitation, ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations, as appreciated by those of ordinary skill in the art.

The term "alkynyl", when used alone or in combination, denotes linear or branched radicals having at least one carbon-carbon triple bond and having two to ten carbon atoms. Examples of alkynyl radicals include "lower alkynyl" radicals having two to about six carbon atoms and, for example, lower alkynyl radicals having two to about four carbon atoms. Examples of such radicals include, without limitation, ethynyl, propynyl (propargyl), butynyl, and the like.

The term "$C_{\alpha-\beta}$-alkyl", "$C_{\alpha-\beta}$-alkenyl" and "$C_{\alpha-\beta}$-alkynyl", when used with other terms such as "wherein 1, 2 or 3 carbon atoms of said $C_{\alpha-\beta}$-alkyl, $C_{\alpha-\beta}$-alkenyl or $C_{2\alpha-\beta}$-alkynyl is optionally replaced with a heteroatom selected from O, S, S(O), $S(O)_2$ and N" embraces linear or branched radicals wherein one or more of the carbon atoms may be replaced with a heteroatom. Examples of such "alkyl" radicals include —O-methyl, —O-ethyl, $—CH_2—O—CH_3$, $—CH_2CH_2—O—CH_3$, $—NH—CH_2$, $—CH_2CH_2—N(CH_3)—CH_3$, $—S—(CH_2)_3CH_2$, $—CH_2CH_2—S—CH_3$ and the like. Accordingly, such radicals also include radicals encompassed by $—OR^7$ where $R^7$ may be defined as a $C_{\alpha-\beta}$-alkyl. Examples of such "alkenyl" radicals include $\sim CH═CH—O—CH_3$, $—NH—CH_2CH═CH_2$, $—S—CH_2CH_2CH═CHCH_3$ and the like. Similar examples exist for such "alkynyl" radicals, as appreciated by those skilled in the art.

The term "$C_{\alpha-\beta}$alkoxyl" when used alone or in combination, embraces linear or branched oxygen-containing alkyl radicals each having α to β number of carbon atoms (such as $C_1$-$C_{10}$). The terms "alkoxy" and "alkoxyl", when used alone or in combination, embraces linear or branched oxygen-containing radicals each having alkyl and substituted alkyl portions of one or more carbon atoms. Examples of such radicals include methoxy, ethoxy, propoxy, butoxy and tert-butoxy. Alkoxy radicals may be further substituted with one or more halo atoms, such as fluoro, chloro or bromo, to provide "haloalkoxy" radicals or with other substitution. Examples of such radicals include fluoromethoxy, chloromethoxy, trifluoromethoxy, trifluoroethoxy, fluoroethoxy, fluoropropoxy and cyclopropylmethoxy.

The term "aryl", when used alone or in combination, means a carbocyclic aromatic moiety containing one, two or even three rings wherein such rings may be attached together in a fused manner. Every ring of an "aryl" multi-ring system need not be aromatic, and the ring(s) fused to the aromatic ring may be partially or fully unsaturated and include one or more heteroatoms selected from nitrogen, oxygen and sulfur. Thus, the term "aryl" embraces aromatic radicals such as phenyl, naphthyl, indenyl, tetrahydronaphthyl, dihydrobenzafuranyl, anthracenyl, indanyl, benzodioxazinyl, and the like. The "aryl" group may be substituted, such as with 1 to 5 substituents including lower alkyl, hydroxyl, halo, haloalkyl, nitro, cyano, alkoxy and lower alkylamino, and the like. Phenyl substituted with $—O—CH_2—O—$ or $—O—CH_2—CH_2—O—$ forms an aryl benzodioxolyl substituent.

The term "carbocyclic", also referred to herein as "cycloalkyl", when used alone or in combination, means a partially or fully saturated ring moiety of carbon atoms containing one ("monocyclic"), two ("bicyclic") or even three ("tricyclic") rings wherein such rings may be attached together in a fused manner and formed from carbon atoms. Examples of saturated carbocyclic radicals include saturated 3 to 6-membered monocyclic groups such as cyclopropane, cyclobutane, cyclopentane and cyclohexane.

The terms “ring” and “ring system” refer to a ring comprising the delineated number of atoms, the atoms being carbon or, where indicated, a heteroatom such as nitrogen, oxygen or sulfur. Where the number of atoms is not delineated, such as a “monocyclic ring system” or a “bicyclic ring system”, the numbers of atoms are 3-8 for a monocyclic and 6-12 for a bicyclic ring. The ring itself, as well as any substitutents thereon, may be attached at any atom that allows a stable compound to be formed. The term “nonaromatic” ring or ring system refers to the fact that at least one, but not necessarily all, rings in a bicyclic or tricyclic ring system is nonaromatic.

The term “cycloalkenyl”, when used alone or in combination, means a partially or fully saturated cycloalkyl containing one, two or even three rings in a structure having at least one carbon-carbon double bond in the structure. Examples of cycloalkenyl groups include $C_3$-$C_6$ rings, such as compounds including, without limitation, cyclopropene, cyclobutene, cyclopentene and cyclohexene. The term also includes carbocyclic groups having two or more carbon-carbon double bonds such as “cycloalkyldienyl” compounds. Examples of cycloalkyldienyl groups include, without limitation, cyclopentadiene and cycloheptadiene.

The term “halo”, when used alone or in combination, means halogens such as fluorine, chlorine, bromine or iodine atoms.

The term “haloalkyl”, when used alone or in combination, embraces radicals wherein any one or more of the alkyl carbon atoms is substituted with halo as defined above. For example, this term includes monohaloalkyl, dihaloalkyl and polyhaloalkyl radicals such as a perhaloalkyl. A monohaloalkyl radical, for example, may have either an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. “Perfluoroalkyl”, as used herein, refers to alkyl radicals having all hydrogen atoms replaced with fluoro atoms. Examples include trifluoromethyl and pentafluoroethyl.

The term “heteroaryl”, as used herein, either alone or in combination, means a fully unsaturated (aromatic) ring moiety formed from carbon atoms and having one or more heteroatoms selected from nitrogen, oxygen and sulfur. The ring moiety or ring system may contain one (“monocyclic”), two (“bicyclic”) or even three (“tricyclic”) rings wherein such rings are attached together in a fused manner. Every ring of a “heteroaryl” ring system need not be aromatic, and the ring(s) fused thereto (to the heteroaromatic ring) may be partially or fully saturated and optionally include one or more heteroatoms selected from nitrogen, oxygen and sulfur. The term “heteroaryl” does not include rings having ring members of —O—O—, —O—S— or —S—S—.

Examples of heteroaryl radicals, include unsaturated 5- to 6-membered heteromonocyclyl groups containing 1 to 4 nitrogen atoms, including for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl] and tetrazole; unsaturated 7- to 10-membered heterobicyclyl groups containing 1 to 4 nitrogen atoms, including for example, quinolinyl, isoquinolinyl, quinazolinyl, isoquinazolinyl, aza-quinazolinyl, and the like; unsaturated 5- to 6-membered heteromonocyclic group containing an oxygen atom, for example, pyranyl, 2-furyl, 3-furyl, benzofuryl, etc.; unsaturated 5 to 6-membered heteromonocyclic group containing a sulfur atom, for example, 2-thienyl, 3-thienyl, benzothienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, isothiazolyl, thiadiazolyl [e.g., 1,2,4-thiadiazolyl, 1,3,4-thiadiazolyl, 1,2,5-thiadiazolyl].

The term “heterocyclic”, when used alone or in combination, means a partially or fully saturated ring moiety containing one, two or even three rings wherein such rings may be attached together in a fused manner, formed from carbon atoms and including one or more heteroatoms selected from N, O or S. Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

The term “heterocycle” also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Examples of heterocyclic radicals include five to ten membered fused or unfused radicals.

Examples of partially saturated and fully saturated heterocyclyls include, without limitation, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl, and the like.

The phrase “a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S” as used herein is intended to encompass all monocyclic and bicyclic rings as small as three atoms to as large as 12 atoms in size, including both carbocyclic rings and heterocyclic, aromatic and non-aromatic rings. The non-aromatic rings may be partially or fully saturated in nature.

The term "alkylamino" includes "N-alkylamino" where amino radicals are independently substituted with one alkyl radical. Preferred alkylamino radicals are "lower alkylamino" radicals having one to six carbon atoms. Even more preferred are lower alkylamino radicals having one to three carbon atoms. Examples of such lower alkylamino radicals include N-methylamino, and N-ethylamino, N-propylamino, N-isopropylamino and the like.

The term "dialkylamino" includes "N,N-dialkylamino" and —"N-di-$C_{\alpha-\beta}$-alkyl" where amino radicals are independently substituted with two $C_{\alpha-\beta}$-alkyl radicals. Preferred alkylamino radicals are "lower alkylamino" radicals having one to six carbon atoms. Even more preferred are lower alkylamino radicals having one to three carbon atoms. Examples of such lower alkylamino radicals include N,N-dimethylamino, N,N-diethylamino, N-methyl,N-ethylamino and the like.

The term "oxo" is also used herein synonymously with "carbonyl" and denotes —(C═O). The term "carbonyl" whether used alone or with other terms, such as "aminocarbonyl", also denotes —(C═O)—. "The term "aminocarbonyl" denotes an amide group of the formula $—C(═O)NH_2$.

The term "alkylthio" or "thioalkoxy" embraces radicals containing a linear or branched alkyl radical, of one to ten carbon atoms, attached to a divalent sulfur atom. An example of "alkylthio" or "thioalkoxy" is methylthio,($CH_3S—$).

The term "Formula I" includes any sub formulas, such as Formula II.

The term "pharmaceutically-acceptable" when used with reference to a compound of Formulas I or II is intended to refer to a form of the compound that is safe for administration. For example, a salt form, a solvate, a hydrate or derivative form of a compound of Formula I or of Formula II would be pharmaceutically acceptable if it has been approved for mammalian use, via oral ingestion or other routes of administration, by a governing body or regulatory agency or authority, such as the Food and Drug Administration (FDA) of the United States.

Included in the compounds of Formulas I and II are the pharmaceutically acceptable salt forms of the free-base compounds. The term "pharmaceutically-acceptable salts" embraces salts commonly used to form alkali metal salts and to form addition salts of free acids or free bases. As appreciated by those of ordinary skill in the art, salts may be formed from ionic associations, charge-charge interactions, covalent bonding, complexation, coordination, etc. The nature of the salt is not critical, provided that it is pharmaceutically acceptable.

Suitable pharmaceutically acceptable acid addition salts of compounds of Formulas I and II may be prepared from an inorganic acid or from an organic acid. Examples of such inorganic acids are hydrochloric, hydrobromic, hydroiodic, hydrofluoric, nitric, carbonic, sulfuric and phosphoric acid. Appropriate organic acids may be selected from aliphatic, cycloaliphatic, aromatic, arylaliphatic, heterocyclic, carboxylic and sulfonic acids, Examples of classes of suitable organic acids include, without limitation, formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, thiocyanic, undecanoic, stearic, algenic, β-hydroxybutyric, salicylic, galactaric and galacturonic acid. Suitable pharmaceutically-acceptable base addition salts of compounds of Formulas I and II include metallic salts, such as salts made from aluminum, calcium, lithium, magnesium, potassium, sodium and zinc, or salts made from organic bases including, without limitation, primary, secondary and tertiary amines, substituted amines including cyclic amines, such as caffeine, arginine, diethylamine, N-ethyl piperidine, histidine, glucamine, isopropylamine, lysine, morpholine, N-ethyl morpholine, piperazine, piperidine, triethylamine, disopropylethylamine and trimethylamine. All of these salts may be prepared by conventional means from the corresponding compound of the invention by reacting, for example, the appropriate acid or base with the compound of Formulas I-II.

Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Additional examples of such salts can be found in Berge et al., J. Pharm. Sci., 66:1 (1977). Conventional methods may be used to form the salts. For example, a phosphate salt of a compound of the invention may be made by combining the desired compound free base in a desired solvent, or combination of solvents, with phosphoric acid in a desired stoichiometric amount, at a desired temperature, typically under heat (depending upon the boiling point of the solvent). The salt can be precipitated upon cooling (slow or fast) and may crystallize (i.e., if crystalline in nature), as appreciated by those of ordinary skill in the art. Further, hemi-, mono-, di, tri- and poly-salt forms of the compounds of the present invention are also contemplated herein. Similarly, hemi-, mono-, di, tri- and poly-hydrated forms of the compounds, salts and derivatives thereof, are also contemplated herein.

The term "derivative" is intended to encompass any salt of a compound of this invention, any ester of a compound of this invention, or any other compound, which upon administration to a patient is capable of providing (directly or indirectly) a compound of this invention, or a metabolite or residue thereof, characterized by the ability to the ability to modulate an enzyme.

The term "pharmaceutically-acceptable derivative" as used herein, denotes a derivative which is pharmaceutically acceptable.

The term "prodrug", as used herein, denotes a compound which upon administration to a subject or patient is capable of providing (directly or indirectly) a compound of this invention. Examples of prodrugs would include esterified or hydroxylated compounds where the ester or hydroxyl groups would cleave in vivo, such as in the gut, to produce a compound according to Formula I-II. A "pharmaceutically-acceptable prodrug" as used herein, denotes a prodrug which is pharmaceutically acceptable. Pharmaceutically acceptable modifications to the compounds of Formula I-II are readily appreciated by those of ordinary skill in the art.

The compound(s) of Formulas I or II may be used to treat a subject by administering the compound(s) as a pharmaceutical composition. To this end, the compound(s) can be combined with one or more excipients, including without limitation, carriers, diluents or adjuvants, to form a suitable composition, which is described in more detail herein.

The term "excipient", as used herein, denotes any pharmaceutically acceptable additive, carrier, adjuvant, or other suitable ingredient, other than the active pharmaceutical ingredient (API), which is typically included for formulation and/or administration purposes. "Diluent" and "adjuvant" are defined hereinafter.

The terms "treat", "treating," "treatment," and "therapy" as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The phrase "effective dosage amount" is intended to quantify the amount of each agent, which will achieve the goal of improvement in disorder severity and the frequency of incidence over treatment of each agent by itself, while avoiding adverse side effects typically associated with alternative therapies. Accordingly, this term is not limited to a single dose, but may comprise multiple dosages required to bring about a therapeutic or prophylactic response in the subject. For example, "effective dosage amount" is not limited to a single capsule or tablet, but may include more than one capsule or tablet, which is the dose prescribed by a qualified physician or medical care giver to the subject.

The term "leaving group" (also denoted as "LG") generally refers to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., $SCH_3$), N-hydroxsuccinimide, N-hydroxybenzotriazole, and the like. Nucleophiles are species that are capable of attacking a molecule at the point of attachment of the leaving group causing displacement of the leaving group. Nucleophiles are known in the art. Examples of nucleophilic groups include, but are not limited to, amines, thiols, alcohols, Grignard reagents, anionic species (e.g., alkoxides, amides, carbanions) and the like.

General Synthetic Procedures

The present invention further comprises procedures for the preparation of compounds of Formulas I and II. The compounds of Formulas I or II can be synthesized according to the procedures described in the following Schemes 1-9, wherein the substituents are as defined for Formulas I and II above, except where further noted. The synthetic methods described below are merely exemplary, and the compounds of the invention may also be synthesized by alternate routes utilizing alternative synthetic strategies, as appreciated by persons of ordinary skill in the art.

The following list of abbreviations used throughout the specification represent the following and should assist in understanding the invention:

ACN, MeCN—acetonitrile
Aq., aq.—aqueous
Ar—argon (gas)
BOP—benzotriazol-1-yl-oxy Hexafluorophosphate
BuLi—Butyllithium
$Cs_2CO_3$—cesium carbonate
$CHCl_3$—chloroform
$CH_2Cl_2$, DCM—dichloromethane, methylene chloride
Cu(1)I—copper(1) iodide
DCC—dicyclohexylcarbodiimide
DIC—1,3-diisopropylcarbodiimide
DIEA, DIPEA—diisopropylethylamine
DME—dimethoxyethane
DMF—dimethylformamide
DMAP—4-dimethylaminopyridine
DMS—dimethylsulfide
DMSO—dimethylsulfoxide
EDC, EDCI—1-(3-dimethylaminopropyl)-3-ethylcarbodiimide
$Et_2O$—diethyl ether
EtOAc—ethyl acetate
FBS—fetal bovine serum
G, gm—gram
h, hr—hour
$H_2$—hydrogen
$H_2O$—water
HATU—O-(7-azabenzotriazol-1-yl)-N,N,N',N'-tetramethyluroniumhexafluorophosphate
HBr—hydrobromic acid
HCl—hydrochloric acid
HOBt—1-hydroxybenzotriazole hydrate
HOAc—acetic acid
HPLC—high pressure liquid chromatography
IPA, IpOH—isopropyl alcohol
$K_2CO_3$—potassium carbonate
KI—potassium iodide
LG—leaving group
LDA—Lithium diisopropylamide
LiOH—lithium hydroxide
$MgSO_4$—magnesium sulfate
MS—mass spectrum
MeOH—methanol
$N_2$—nitrogen
$NaCNBH_3$—sodium cyanoborohydride
$Na_2CO_3$—sodium carbonate
$NaHCO_3$—sodium bicarbonate
NaH—sodium hydride
NaI—sodium iodide
$NaBH_4$—sodium borohydride
NaOH—sodium hydroxide
$Na_2SO_4$—sodium sulfate
$NH_4Cl$—ammonium chloride
$NH_4OH$—ammonium hydroxide
$P(t\text{-}bu)_3$—tri(tert-butyl)phosphine
PBS—phospate buffered saline
Pd/C—palladium on carbon
$Pd(PPh_3)_4$—palladium(0)triphenylphosphine tetrakis
$Pd(dppf)Cl_2$—palladium(1,1-bisdiphenylphosphinoferrocene) II chloride
$Pd(PhCN)_2Cl_2$—palladium di-cyanophenyl dichloride
$Pd(OAc)_2$—palladium acetate
$Pd_2(dba)_3$—tris(dibenzylideneacetone) dipalladium
PyBop—benzotriazol-1-yl-oxy-tripyrrolidino-phosphonium hexafluorophosphate
RT, rt—room temperature
RBF, rbf—round bottom flask
TLC, tlc—thin layer chromatography
TBAF—Tetrabutylammonium flouride
TBTU—O-benzotriazol-1-yl-N,N,N,N'-tetramethyluronium tetrafluoroborate
TEA, $Et_3N$—triethylamine
TFA—trifluoroacetic acid
THF—tetrahydrofuran
UV—ultraviolet light While the synthetic strategy for preparing the compounds of Formulas I and II may vary, as appreciated by persons skilled in the art, one strategy for devising a method of making compounds of these formulas is by retro-synthetic disconnection. For example,

I

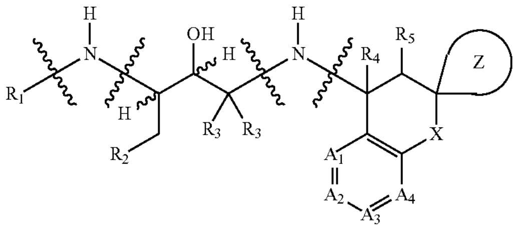

and

-continued

II

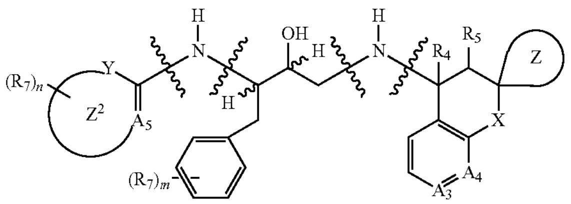

as shown in Formulas I-II above, each squiggly line represents a possible point of bond-construction, whose order is generally dependent upon the particular compound being synthesized. Such bond construction methods are generally described in synthetic Schemes 1-9 below.

Scheme 1

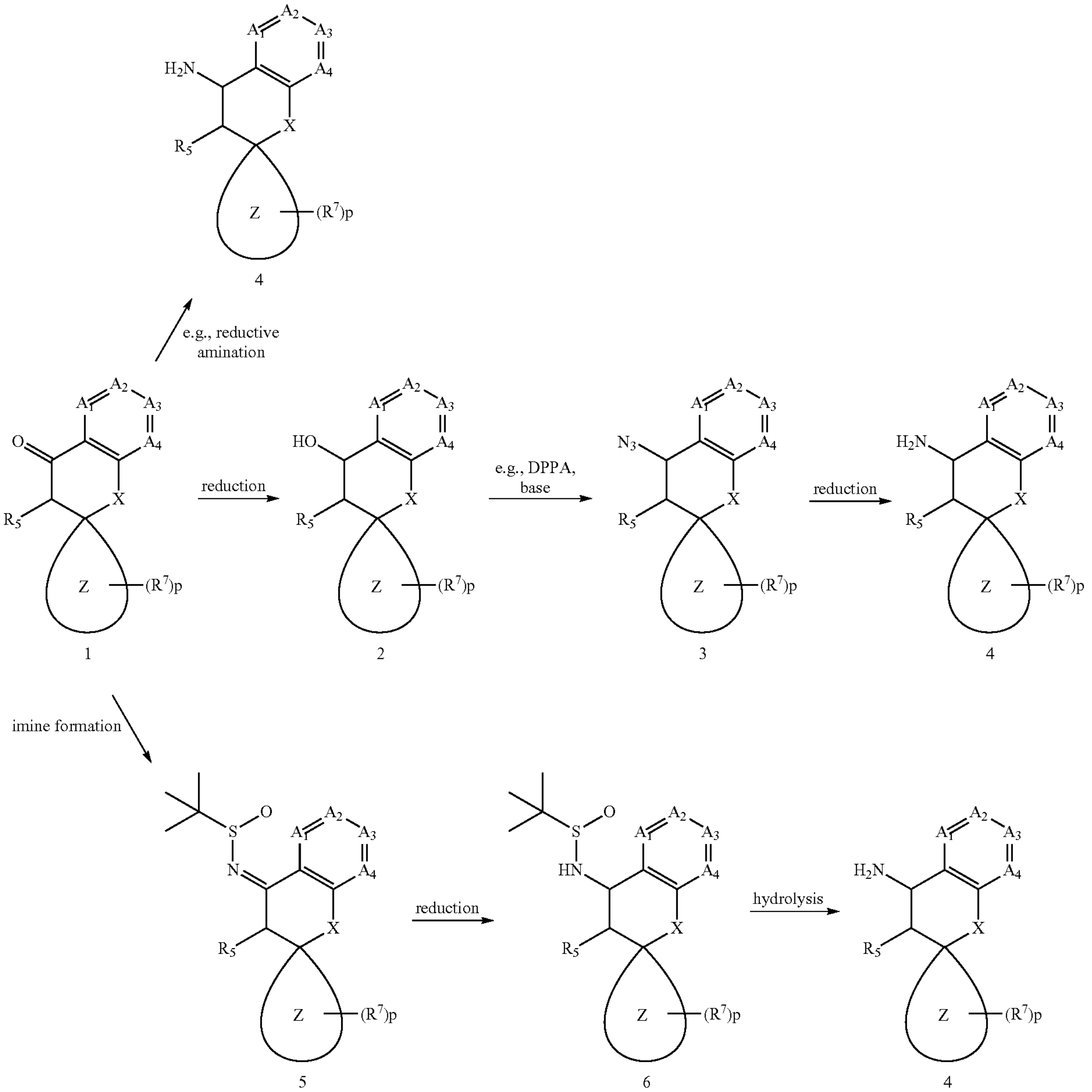

Amine intermediate 4 can be prepared according to the method generally described in Scheme 1. As shown, spiro-substituted- or gem-dialky-substituted (not shown) oxo-$R^5$ ring intermediates 1 can be converted directly to the amino-intermediate 4 using known reductive amination methods, such as in the presence of sodium cyanoborohydride and ammonium acetate. Alternatively, the carbonyl of compound 1 may be reduced to the corresponding alcohol 2 using conventional reducing reagents, and then displaced to form the corresponding azido-intermediate 3 using known reagents, such as DPPA, in the presence of a suitable base as shown. Intermediate 3 may be reduced with a suitable reducing agent or by known methods, including triphenylphosphene, trimethylphosphene or lithium aluminum hydride (LAH), to produce the desired amino adduct 4.

Yet another method of forming the amine adduct 4, can be via an imine formation to form compound 5. The imine double bond of compound 5 may then be successively reduced and hydrolyzed to yield the primary amine product 4. Such steps may be conducted using known, convention methods, as appreciated by those skilled in the art.

Scheme 2

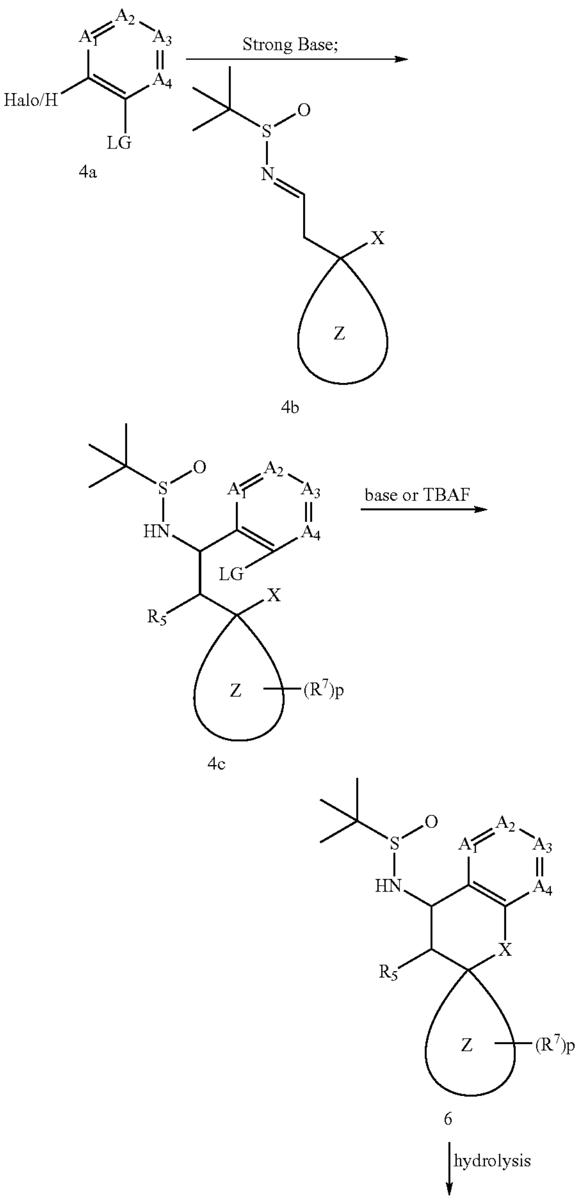

4a

4b

4c

6

-continued

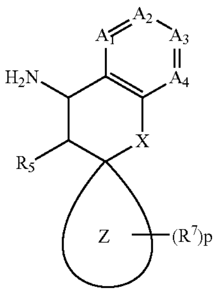

4

Alternatively, amine intermediates 4 may be prepared by the method shown in scheme 2 above. Desirably substituted compounds 4a may first be treated with a strong base, such as LDA or n-butyl lithium, to form an anion that may then be added to a sufinylimine intermediate 4b to form the corresponding coupled adduct 4c. Open intermediate 4c may subsequently be treated with a strong base, such as NaH (wherein, e.g., X is a nucleophile such as OH, SH or $NHR^6$ or TBAF (wherein, e.g., X1 is $OSiR_3$) to form intermediate 6. Intermediate 6 may then be deprotected to provide the desired spiro amine compound 4.

Scheme 3

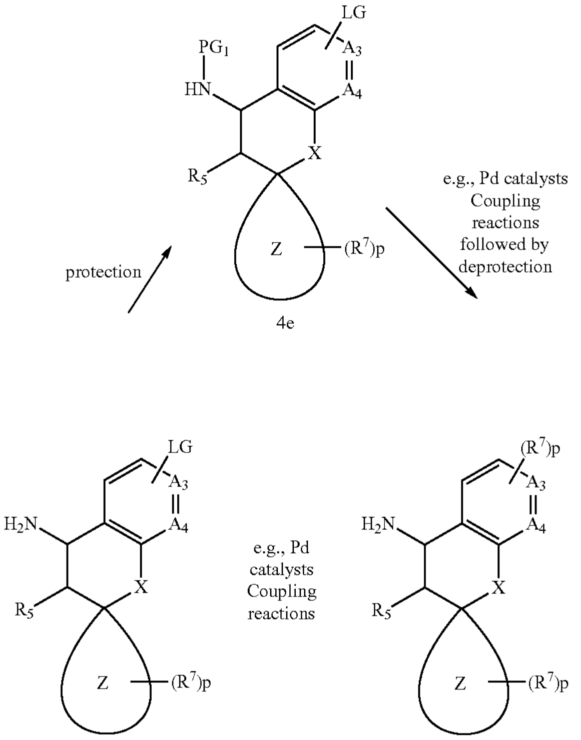

4e

4d

4

-continued

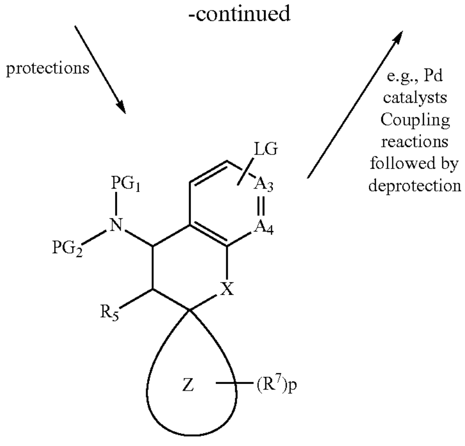

4f

LG = Cl, Br, I, OTf, etc.

Amine intermediate 4 can also be prepared from other amine 4 precursors such as 4d containing an appropriate leaving group (LG, e.g., Cl, Br, I, OTf, etc) as shown in scheme 3 above. Using this method, compound 4d, with the amino group used as is, mono-protected (compound 4e), or doubly protected (compound 4f having PG1 and PG2 protecting groups as shown), can be coupled with the requisite neucleophilic reagents with a catalyst such as a Pd-catalyst selected from appropriate sources. The said neucleophilic reagents can be selected from, but not limited to, commercial or pre-formed boronic reagents, stannane reagents, Zinc- or Magnesium-derived metallic reagents. After deprotection if necessary, amine intermediate 4 can be obtained.

Scheme 4

1.

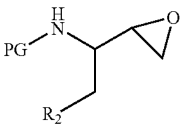

+

6'

PG = protecting group

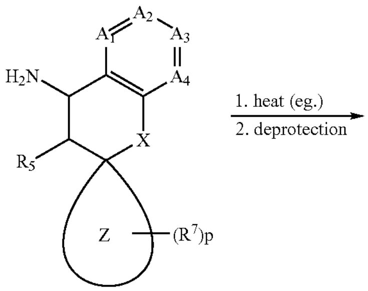

4

-continued

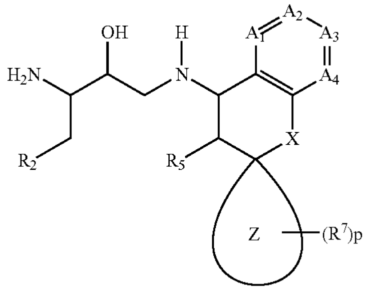

8'

2.

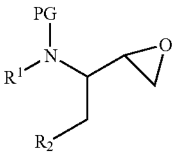

+

6

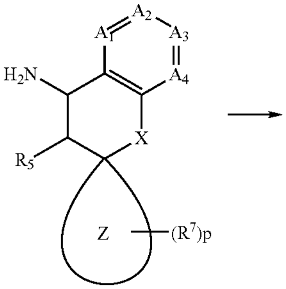

4

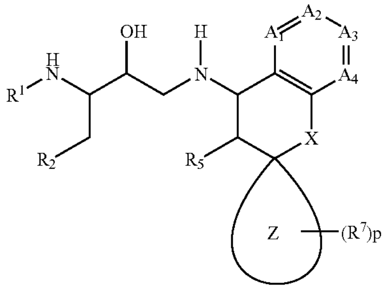

8

3.

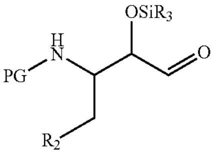

+

7'

PG = protecting group

-continued

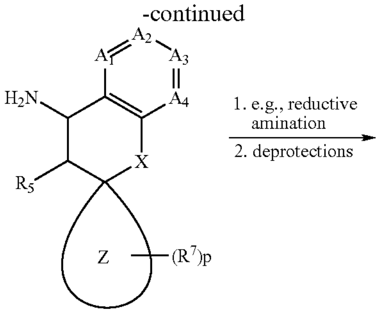

4

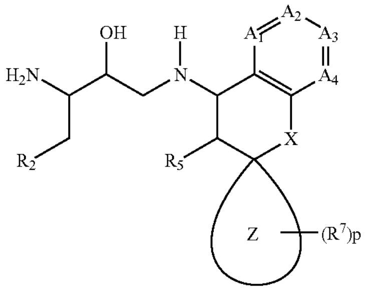

8'

4.

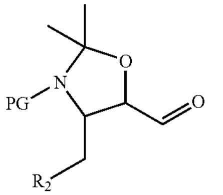

+

7

PG = protecting group

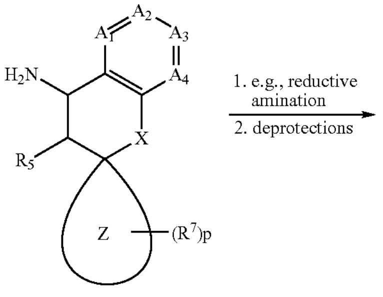

4

-continued

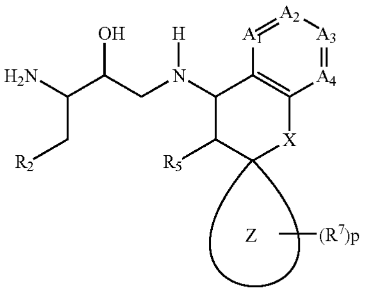

8'

Scheme 4 describes, generally, multiple different methods for constructing the bond between the propyl backbone starting material or intermediate 6' (sub-scheme 1) or 6 (sub-scheme 2) and an spino ring intermediate 4, thereby synthesizing a desired intermediate 8' or a final compound 8 of Formulas I-II. One method to make this bond is to react an epoxide intermediate 6 or 6' (Note: the epoxide 6 or 6' may be purchased commercially or made via known, published methods such as from the olefin precursor), with an amino-spino intermediate 4, as shown. The reaction may proceed in the presence of a polar solvent, such as an alcohol or dioxanes, and may require additional reagents, as appreciated by those skilled in the art. Additionally, the reaction may require heat for a period of time. Note that while the scheme described the addition of heat, this is by way of example, and not every reaction would require heat as appreciated by those of ordinary skill in the art. The protecting group may be removed using an acid, such as HCl, such that the bonded adduct 8' is recovered as an HCl salt.

Alternatively, desired intermediates 8' may be synthesized starting with an amine-protected aldehyde intermediate 7' (sub-scheme 3) or 7 (sub-scheme 4) and condensing the aldehyde with a primary or secondary amine 4 to form an imine (not shown, generally formed in-situ and not isolated). The imine can then be reduced using a known reducing agent, such as a hydride or borohydride, the reduced intermediate may be deprotected to provide an intermediate 8' having an amine useful to prepare compounds 8 of Formulas I-II.

Scheme 5

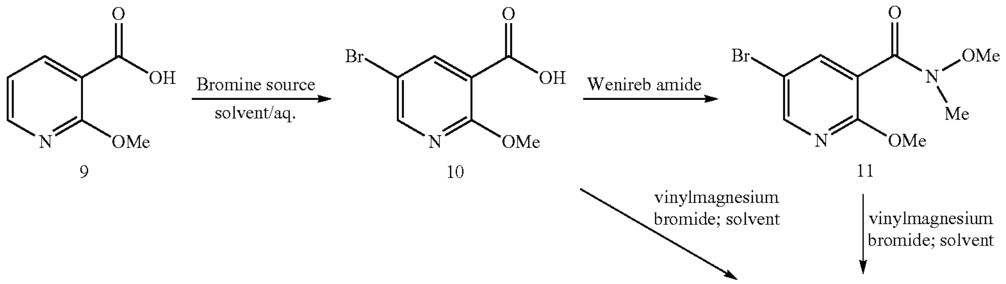

9 10 11

-continued

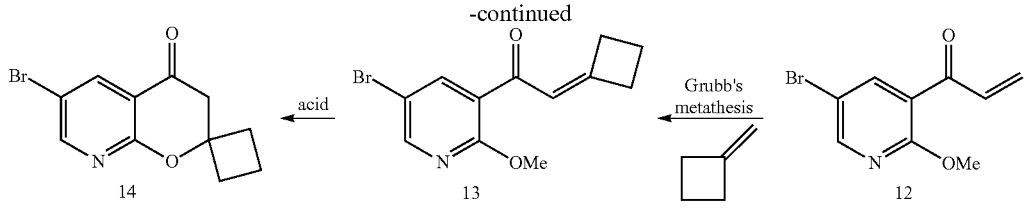

14 13 12

Scheme 5 describes, generally, another method for constructing gem-dialkyl (not shown) or spiro (shown) compounds 4 in schemes 2 and 3 above, by first preparing the corresponding bromo-keto-intermediate 14 as schematically illustrated above. As shown, a methoxy picolinic acid 9 can be reacted with an aqueous bromine source, such bromine, in the presence of a suitable solvent, such as DCM/water, to form the corresponding brominated intermediate 10. The acid group of compound 10 can be converted to the corresponding Weinreb amide under known conditions, such as using EDC-HCl in the presence of HOBt, a base such as TEA, and a suitable solvent such as DCM. Weinreb 11 may be treated with a desired Grignard reagent, such as vinylmagnesium bromide as shown above, in the presence of a suitable solvent, such as THF, to form the allylic ketone species 12. Alternatively, the Weinreb amide species may be bypassed by treating compounds 10 directly with the Grignard reagents, such the one shown above, to afford compounds 12. Compound 12 can undergo a Grubb's metathesis, such as by utilizing exo-methylene cyclobutane as shown above, to form intermediate 13, which may then be cyclized to ring closure using a suitable acidic environment, such as in EtOH/HCl, to provide the desired compounds 14. An additional method to prepare mono-substituted aza-chroman compounds, but not gem-dialkyl or spiro aza-chroman compounds 14 is described in Sarges et at, *J. Med. Chem.,* 1990, 33, 1859-1865, which disclosure is hereby incorporated herein by reference in its entirety. The keto-intermediate 14 can then be converted to the corresponding primay amino species using the chemistry taught herein.

Scheme 6

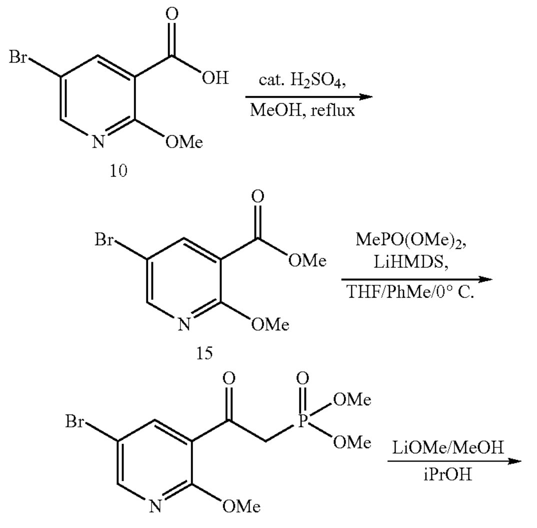

10 15 16

-continued

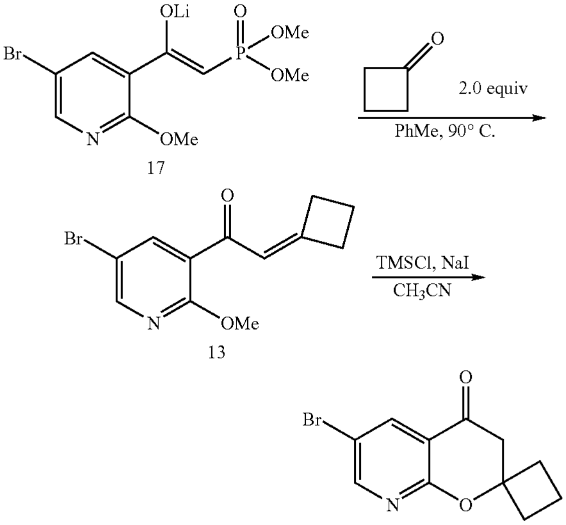

17 13 14

Scheme 6 describes, generally, yet another method for constructing gem-dialkyl (not shown) or spiro (shown) intermediates 13 in scheme 5 above. Compound 13 in turn may be converted to the desired bromo-keto-intermediate 14 as schematically illustrated above. As shown, brominated intermediate 10 from scheme 5 can be reacted with an acid, such as sulfuric acid as shown, in a protic solvent, such as MeOH, to form the corresponding methyl ester intermediate 15. The ester group of compound 15 can be converted to the corresponding phosphonate ester under Horner-Emmons type conditions, which are known in the art, such as using a phosphonate species in the presence of a strong base, such as LiHMDS as shown, and a suitable solvent such as THF and toluene. The resulting phosphonate adduct 16 may be deprotonated with a strong base, such as with liOMe in the presence of an alcoholic solvent such as MeOH and/or I—PrOH, and the lithium enolate can then be reacted with cyclobutanone to afford the adduct compound 13 in high yield. Intermediate 13 may then be cyclized to ring closure using suitable conditions, such as those shown above in scheme 6, to provide the desired compounds 14. Additional description of useful methods which may be used to prepare compounds similar to compound 14 are described in general in Harada et at, JP patent application no. 08099982A, Yasuda et al, *J. Org. Chem.* 2004, 69, pg 1958, Yazbeck et al, *Org. Process Res. Dev.* 2006, 10, pg 655, and in Keneko et al, *Chem. Pharm. Bull.,* 2004, 52, pg 675, which disclosures are hereby incorporated herein by reference in its entirety. The keto-intermediate 14 can then be converted to the corresponding primay amino species using the chemistry taught herein.

It should be appreciated that schemes 5 and 6 illustrate exemplary methods for preparing the right-side spiro or gem-dialkyl pieces of compounds of Formulas I and II. Reaction yields for each step in schemes 5 and 6 range from about 50% to 90+%. Accordingly, these methods may provide a more efficient process for preparing desired intermediates 14. Further, utilizing these methods may afford other spirocyclic rings of differing sizes and heteroatoms, encompassed in the compounds of the present invention.

Scheme 7 (Method A)

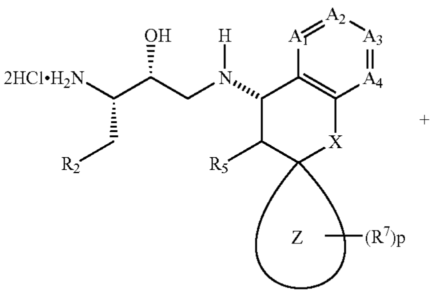

8'

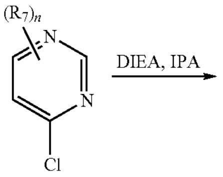

18

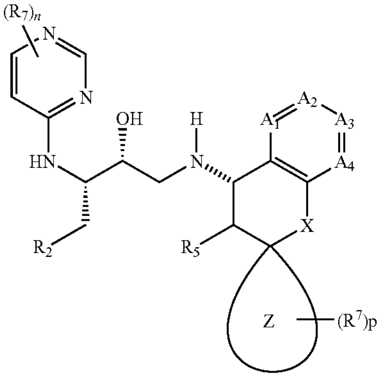

19

Scheme 7 illustrates how one may construct the $R^1$ to amine-backbone bond, where $R^1$, as shown, is an aromatic moiety. Intermediate 8' can be heated in a microwave oven with a desirably substituted chloro-substituted aromatic compound 18 in the presence of a suitable base, such as diisopropylethylamine (DIEA) in a suitable solvent, such as isopropyl alcohol (IPA) to afford the desired product compound 19 of Formula I or II.

Scheme 8 (Method B)

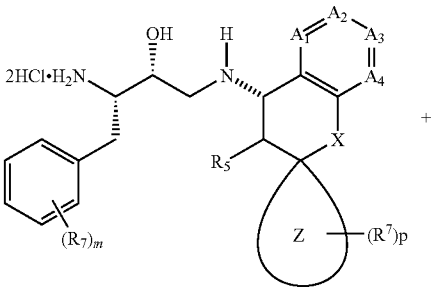

20

-continued

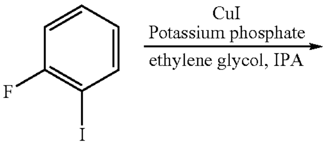

21

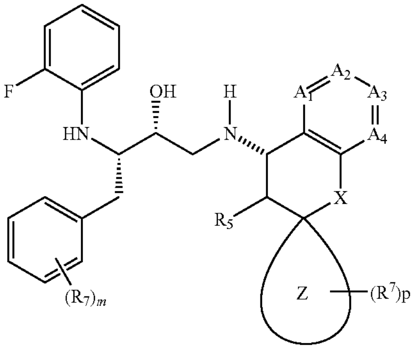

22

Scheme 8 illustrates an alternative method of constructing the $R^1$ to amine backbone bond, where $R^1$, as shown, is another aromatic moiety. Intermediate 20 can be heated together with an iodo-fluorophenyl compound 21 in the presence of Copper iodide (CuI), a suitable base such as potassium phosphate, and a suitable solvent or combination of solvents, such as ethylene glycol and IPA, for a suitable time period to afford the desired product compound 22 of Formula I or II.

Scheme 9 (Method C)

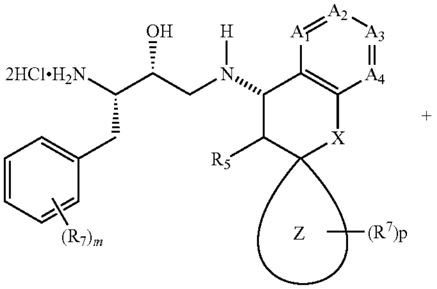

20

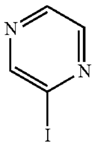

23

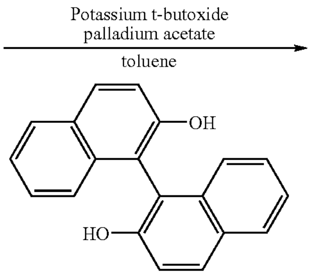

-continued

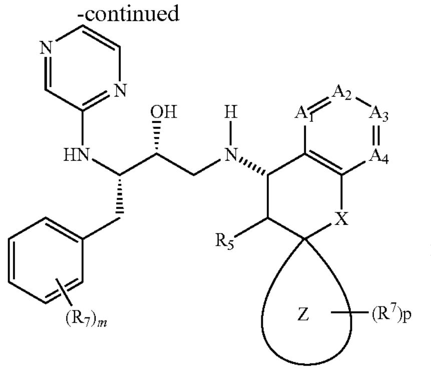

24

Scheme 9 illustrates yet another alternative method of constructing the $R^1$ to amine backbone bond, where $R^1$, as shown, is an aromatic moiety. Intermediate 20 can be combined with suitable amounts of potassium 2-methylpropan-2-olate in toluene and stirred at RT. To this mixture is added 2-iodopyrazine 23 and BINAP, followed by palladium (II) acetate and the mixture is heated to about 50° C. for a suitable time period in which to afford the desired compound 24. The reaction mixture is then cooled and compound 24 can be purified from this mixture using known conventional methods, such as column chromatography or HPLC methods.

To enhance the understanding and appreciation of the present invention, the following specific examples (starting reagents, intermediates and compounds of Formulas I-II) are set forth. The following analytical methods were used to purify and/or characterize the compounds, and intermediates, described in the examples below. Additional general and specific exemplary methods for making the intermediates and building block compounds are described in PCT publication No. WO 2007061670, which disclosure is incorporated herein by reference in its entirety.

Analytical HPLC and LC-MS Methods:

Unless otherwise indicated, all analytical HPLC analyses were run on an Agilent Model 1100 series system LC/MSD SL using one of the two following Columns: (a) Phenomenex Sernegi (4 micron, C18, 50×2 mm) or (b) a Gemini column (5 micron, C18, 100×2 mm) A typical run through the instrument included: eluting at 1 ml/min with an linear gradient of 10% (v/v) to 100% MeCN (0.1% v/v TFA) in water (0.1% TFA) over 10 minutes; conditions may be varied to achieve optimal separation.

Chromatography: Unless otherwise indicated, crude product-containing residues were purified by passing the crude material orconcentrate through an ISCO brand silica gel column (pre-packed or individually packed with $SiO_2$) and eluting the product off the column with a solvent gradient as indicated. For example a description of (330 g $SiO_2$, 0-40% EtOAc/Hexane) means the product was obtained by elution from the column packed with 330 gms of silica, with a solvent gradient of 0% to 40% EtOAc in Hexanes.

Preparative HPLC Method:

Unless otherwise indicated, the compounds described herein were purified via reverse phase HPLC using one of the following instruments: Shimadzu, varian, Gilson; utilizing one of the following two HPLC columns: (a) a Phenomenex Luna or (b) a Gemini column (5 micron or 10 micron, C18, 150×50 mm)

A typical run through the instrument included: eluting at 45 ml/min with a linear gradient of 10% (v/v) to 100% MeCN (0.1% v/v TFA) in water (0.1% TFA) over 10 minutes; conditions can be varied to achieve optimal separations.

Proton NMR Spectra:

Unless otherwise indicated, all $^1H$ NMR spectra were run on a Bruker series 300 MHz instrument or a Bruker series 400 MHz instrument. Where so characterized, all observed protons are reported as parts-per-million (ppm) downfield from tetramethylsilane (TMS) or other internal reference in the appropriate solvent indicated.

Mass Spectra (MS)

Unless otherwise indicated, all mass spectral data for starting materials, intermediates and/or exemplary compounds are reported as mass/charge (m/z), having an $(M+H^+)$ molecular ion. The molecular ion reported was obtained by electrospray detection method (commonly referred to as an ESI MS) utilizing a PE SCIEX API 150EX MS instrument. Compounds having an isotopic atom, such as bromine and the like, are generally reported according to the detected isotopic pattern, as appreciated by those skilled in the art.

Naming Convention

The compounds disclosed and described herein have been named using the naming convention provided with Chem-Draw Ultra 8.0 software, available in Chem. Office. In some instances, compounds were named with the term "spirocarbocycle" inserted where appropriate. For example, where the chroman is substituted with 2,2-spirocyclobutyl, "2,2-spirocyclobutyl" is added to the Chem-Draw nomenclature in the appropriate place. Chem-Draw utilizes the ISIS Draw software compound naming convention, as appreciated by those skilled in the art.

EXAMPLES

The Examples, described herein below, represent various exemplary starting materials, intermediates and compounds of Formulas I-II, which should assist in a better understanding and appreciation of the scope of the present invention and of the various methods which may be used to synthesize compounds of Formulas I and II. It should be appreciated that the general methods above and specific examples below are illustrative only, for the purpose of assistance and of understanding the present invention, and should not be construed as limiting the scope of the present invention in any manner.

Example 1

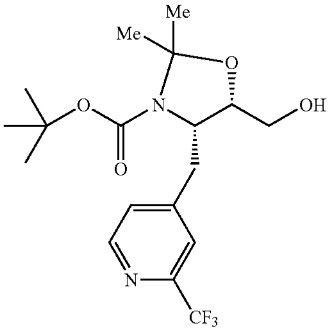

(4S,5S)-tert-Butyl 5-(hydroxymethyl)-2,2-dimethyl-4-((2-(trifluoromethyl)pyridin-4-yl)methyl)oxazolidine-3-carboxylate Step 1: (S)-Methyl 2-(tert-butoxycarbonyl)-3-(2-(trifluoromethyl)pyridin-4-yl)propanoate The title compound was prepared according to previously reported procedure (U.S. patent application Ser. No. 11/575,187) from (R)-methyl 2-(tert-butoxycarbonyl)-3-iodopropanoate and 4-iodo-2-(trifluoromethyl)pyridine (this starting material was prepared according to a procedure described in *Eur. J. Org. Chem.* 2003, 1559-1568).

Step 2: (4S,5S)-tert-Butyl 5-(hydroxymethyl)-2,2-dimethyl-4-(2-(trifluoromethyl)pyridin-4-yl)methyl) oxazolidine-3-carboxylate The title compound was prepared according to procedure described in U.S. patent application Ser. No. 11/575,187, from (S)-methyl 2-(tert-butoxycarbonyl)-3-(2-(trifluoromethyl)pyridin-4-yl)propanoate.

Example 2

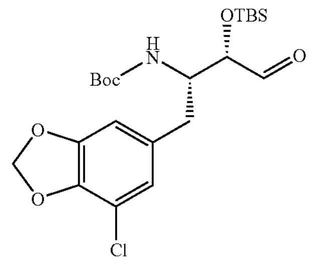

(S)-tert-Butyl 3-(7-chlorobenzo[d][1,3]dioxol-5-yl)-1-oxo-1-(thiazol-2-yl)propan-2-ylcarbamate Step 1: (S)-tert-Butyl 3-(7-chlorobenzo[d][1,3]dioxol-5-yl)-1-oxo-1-(thiazol-2-yl)propan-2-ylcarbamate A solution of 2-bromothiazole (3 ml, 37 mmol) in ether (75 mL) was cooled to −78° C. and treated with n-butyllithium 2M in hexanes (18 ml, 37 mmol). After stirring the reaction for 30 minutes, a solution of (S)-methyl 2-(tert-butoxycarbonyl)-3-(7-chlorobenzo[d][1,3]dioxol-5-yl)propanoate (6.610 g, 18 mmol) in ether (75 mL) was added, and the reaction mixture was allowed to stir at −78° C. for 1 hour. The reaction mixture was quenched with saturated NH4Cl solution, washed with water and brine. The organic layers were dried over $MgSO_4$ and concentrated under reduced pressure. Purification of the crude residue by column chromatography gave (S)-tert-butyl 3-(7-chlorobenzo[d][1,3]dioxol-5-yl)-1-oxo-1-(thiazol-2-yl)propan-2-ylcarbamate (4.22 g, 56% yield) as a yellow oil.

Step 2: tert-Butyl (1S,2S)-3-(7-chlorobenzo[d][1,3] dioxol-5-yl)-1-hydroxy-1-(thiazol-2-yl)propan-2-ylcarbamate A cooled solution (0° C.) of (S)-tert-butyl 3-(7-chlorobenzo[d][1,3]dioxol-5-yl)-1-oxo-1-(thiazol-2-yl)propan-2-ylcarbamate (4.220 g, 10 mmol) in EtOH (60 mL) was added dropwise via cannula to a cooled solution (−78° C.) of lithium tri-tert-butoxyaluminum hydride 1M in THF (21 ml, 21 mmol) in EtOH (40 mL). After stirring for 2 hours, the reaction mixture was quenched with 1N HCl and diluted with EtOAc. The organic layer was washed with water, saturated $NaHCO_3$ solution, and brine. The organic layer was dried over MgSO4 and concentrated under reduced pressure. The crude residue was crystallized from hot EtOH/water and the solid was collected yielding tert-butyl (1S,2S)-3-(7-chlorobenzo[d][1,3]dioxol-5-yl)-1-hydroxy-1-(thiazol-2-yl)propan-2-ylcarbamate (3.250 g, 77% yield) as a white solid.

Step 3: tert-Butyl (1S,2S)-1-(tert-butyldimethylsilyloxy)-3-(7-chlorobenzo[d][1,3]-dioxol-5-yl)-1-(thiazol-2-yl)propan-2-ylcarbamate A suspension of tert-butyl (1S,2S)-3-(7-chlorobenzo[d][1,3]dioxol-5-yl)-1-hydroxy-1-(thiazol-2-yl)propan-2-ylcarbamate (3.250 g, 8 mmol) in DCM (24 mL) was treated with 2,6-lutidine (1 ml, 12 mmol) followed by tert-butyldimethylsilyl triflate (2 ml, 9 mmol) and was allowed to stir at RT for 2 hours. An additional equivalent of TBS triflate was added followed by an additional equivalent of base. After 1 hour, DIEA (2 ml, 12 mmol) was added, followed by di-tert-butyldicarbonate 1M in THF (8 ml, 8 mmol), and the reaction mixture was allowed to stir at RT overnight. The reaction mixture was quenched with 2N HCl solution, diluted with DCM, and washed with saturated $NaHCO_3$ solution and brine. The organics were dried over $MgSO_4$ and concentrated under reduced pressure. Purification of the crude residue by column chromatography gave tert-butyl (1S,2S)-1-(tert-butyldimethylsilyloxy)-3-(7-chlorobenzo[d][1,3]dioxol-5-yl)-1-(thiazol-2-yl)propan-2-ylcarbamate (1.850 g, 45% yield).

Step 4: tert-Butyl (2S,3S)-3-(tert-butyldimethylsilyloxy)-1-(7-chlorobenzo[d][1,3]-dioxol-5-yl)-4-oxobutan-2-ylcarbamate A solution tert-butyl (1S,2S)-1-(tert-butyldimethylsilyloxy)-3-(7-chlorobenzo[d][1,3]dioxol-5-yl)-1-(thiazol-2-yl) propan-2-ylcarbamate (1.85 g, 3.51 mmol) in MeCN (14 mL) was treated with 4 A mol. seives and was allowed to stir at RT for 10 minutes. Methyl trifluoromethanesulfonate (0.464 ml, 4.21 mmol) was added, and the reaction mixture was allowed to stir for 30 minutes. The reaction mixture was then concentrated under reduced pressure, and the crude residual material was dissolved in MeOH (14 mL), and cooled to 0° C. The mixture was then treated with sodium borohydride (0.398 g, 10.5 mmol) and allowed to warm to RT and stir for an additional 20 minutes. The reaction mixture was diluted with EtOAc, filtered through celite and concentrated under reduced pressure. The residue was dissolved in MeCN (10 mL) and water (4 mL) and was treated with mercury(II) chloride (0.953 g, 3.51 mmol). After stirring for 30 minutes the reaction mixture was diluted with ether and filtered through a short plug of silica. The filtrate was then concentrated under reduced pressure and the crude residue was purified by column chromatography yielding tert-butyl (2S,3S)-3-(tert-butyldimethylsilyloxy)-1-(7-chlorobenzo[d][1,3] dioxol-5-yl)-4-oxobutan-2-ylcarbamate.

Example 3

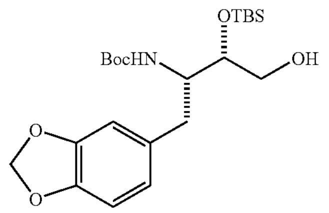

tert-Butyl (2S,3S)-1-(benzo[d][1,3]dioxol-5-yl)-3-(tert-butyldimethylsilyloxy)-4-hydroxybutan-2-ylcarbamate Step 1: N-((2S,3S)-1-(benzo[d][1,3]dioxol-4-yl)-3,4-bis(tert-butyldimethylsilyloxy)butan-2-yl)-2-methylpropane-2-sulfinamide To a slurry of magnesium turnings (1.09 g, 44.8 mmol) in 5 mL of THF was added iodine (0.0650 g, 0.256 mmol), followed by a solution of 5-(chloromethyl)benzo[d][1,3]dioxole (6.55 g, 38.4 mmol) in 30 mL of THF. After 1 minute, the exothermic reaction mixture was placed in an ice bath for 1 minute and then stirred at ambient temperature for 1 hour. TMEDA (7.68 ml, 51.2 mmol) was added to the reaction and the mixture was cooled to −78° C. for 5 minutes at which point a solution of (E)-N—((S)-2,3-bis(tert-butyldimethylsilyloxy)propylidene)-2-methylpropane-2-sulfinamide (5400 mg, 12.8 mmol) in 25 mL THF was added via a syringe pump over 15 minutes. The reaction was allowed to warm to RT over the course of 2 hours then stirred at RT for an additional hour. The mixture was diluted with ethyl acetate (100 mL) and poured in saturated ammonium chloride (250 mL). The aqueous layer was extracted with ethyl acetate (2×250 mL) and the combined organic layers were washed with water and then brine and dried over $Na_2SO_4$. The organic colvents were filtered, concentrated under reduced pressure and the crude material was purified by silica gel to provide N-42R,3S)-1-(benzo[d][1,3]dioxol-5-yl)-3,4-bis(tert-butyldimethylsilyloxy)butan-2-yl)-2-methylpropane-2-sulfinamide (4.51 g, 63.1% yield) as a colorless oil.

Step 2: tert-Butyl (2S,3S)-1-(benzo[d][1,3]dioxol-4-yl)-3-(tert-butyldimethylsilyloxy)-4-hydroxybutan-2-ylcarbamate To a solution of N-((2S,3S)-1-(benzo[d][1,3]dioxol-5-yl)-3,4-bis(tert-butyldimethylsilyloxy)butan-2-yl)-2-methylpropane-2-sulfinamide (2300 mg, 4 mmol) in 25 mL of ethanol at 0° C. was added 4M HCl in dioxane (6 ml, 25 mmol). After stirring at 0° C. for a total of 7 hours, TEA (4 ml, 29 mmol) was added dropwise followed by addition of 25 mL of DCM and di-tert-butyl dicarbonate (2 g, 9 mmol). The mixture was stirred at rt for 48 hours, then diluted with DCM (50 mL) and poured in saturated ammonium chloride (250 mL). The aqueous layer was extracted with DCM (4×100 mL). The combined organic layers were washed with water and brine and dried over $Na_2SO_4$, filtered and concentrated under reduced pressure, to provide an oil that was flashed through a plug of silica gel to provide tert-butyl (2S,3S)-1-(benzo[d][1,3]dioxol-5-yl)-3-(tert-butyldimethylsilyloxy)-4-hydroxybutan-2-ylcarbamate as a colorless oil.

Example 4

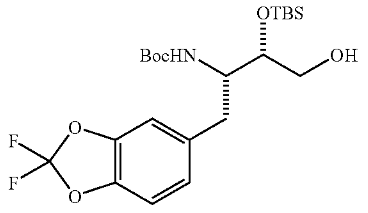

(4S,5S)-tert-Butyl 4-((2,2-difluorobenzo[d][1,3]dioxol-5-yl)methyl)-5-(hydroxymethyl)-2,2-dimethyloxazolidine-3-carboxylate Step 1: (S)-Methyl 2-(tert-butoxycarbonyl)-3-(2,2-difluorobenzo[d][1,3]dioxol-5-yl)propanoate To a 25 mL RBF was added zinc powder (1.03 g, 15.8 mmol) and iodine (0.0161 g, 0.0633 mmol). The mixture was heated with a heat gun for 5 minutes and the resulting mixture was then flushed with nitrogen 3 times and allowed to cool to rt. A solution of (R)-methyl 2-(tert-butoxycarbonyl)-3-iodopropanoate (3.47 g, 10.5 mmol) in 5 mL of DMF was added dropwise to the mixture over 3 minutes and the resulting grey slurry was stirred at 0° C. for 20 minutes before being warmed to rt. After stirring at rt for 30 minutes, 5-bromo-2,2-difluorobenzo[d][1,3]dioxole (2.50 g, 10.5 mmol), $Pd_2(dba)_3$ (0.193 g, 0.211 mmol) and S(Phos) (0.346 g, 0.844 mmol) were added and the reaction mixture was heated to 40° C. for 2 hours. The resulting mixture was cooled to rt and partitioned between ethyl acetate (50 mL) and a solution of ~9:1 saturated ammonium chloride/ammonium hydroxide pH=9 (250 mL). The aqueous layer was extracted with ethyl acetate (3×100 mL) and the combined organic layers were washed with water, brine, and dried over sodium sulfate. Concentration of the filtered solvents and purification of resulting crude material by silica gel chromatography provided (S)-methyl 2-(tert-butoxycarbonyl)-3-(2,2-difluorobenzo[d][1,3]dioxol-5-yl)propanoate (1.89 g, 49.9% yield) as a slightly brown oil.

Step 2: (S)-2-(tert-Butoxycarbonyl)-3-(2,2-difluorobenzo[d][1,3]dioxol-5-yl)propanoic acid To a solution of (S)-methyl 2-(tert-butoxycarbonyl)-3-(2,2-difluorobenzo[d][1,3]dioxol-5-yl)propanoate (1850 mg, 5 mmol) in 50 mL of THF at 0° C. was added LiOH (0.2 M, 26 ml, 5 mmol) over 10 minutes. The reaction was stirred for 2 hours and was then washed with ether (200 mL), acidified to pH 4 with 2 N HCl and extracted with ethyl acetate (4×100 mL). The organics were washed with water and brine and dried over sodium sulfate. Concentration provided (S)-2-(tert-butoxycarbonyl)-3-(2,2-difluorobenzo[d][1,3]dioxol-5-yl)propanoic acid (1.75 g, 98% yield) as a colorless oil.

Step 3: (S)-3-(tert-Butoxycarbonyl)-4-(2,2-difluorobenzo[d][1,3]dioxol-5-yl)-2-oxobutyl acetate To a solution of (S)-2-(tert-butoxycarbonyl)-3-(2,2-difluorobenzo[d][1,3]dioxol-5-yl)propanoic acid (1650 mg, 5 mmol) in 50 mL of THF at 0° C. was added TEA (0.7 ml, 5 mmol) and isobutyl chloroformate (0.6 ml, 5 mmol). The reaction mixture was stirred at 0° C. for 1.5 hours then filtered through a frit containing celite. The solution was cooled to 0° C. and treated with freshly prepared diazomethane (0.5 M in ether, 14 ml, 7 mmol). After stirring for 1 hour at 0° C. the reaction was poured into saturated sodium bicarbonate 250 mL and the aqueous layer was extracted with ethyl acetate (3×100 mL). The combined organic layers were washed with water and then brine and dried over $Na_2SO_4$. Concentration of solvents under reduced pressure provided the diazo ketone as a yellow solid that was carried on without further purification. The derived diazo ketone was taken up in 50 mL of THF and cooled to 0° C. at which point hydrobromic acid, 33 wt. % in acetic acid (0.7 ml, 12 mmol) was added dropwise over 1 minute. After stirring at 0° C. for 1 hour potassium carbonate (1.0 g, 7 mmol) and sodium acetate (4 g, 48 mmol) were added to the mixture. The THF was removed in vacuo and 15 mL of DMF was added to the reaction. The resulting slurry was stirred for 10 minutes at which point the reaction mixture was diluted with ethyl acetate (50 mL) and poured in water 100 mL. The aqueous layer was extracted with ethyl acetate (2×100 mL). The combined organic layers were washed with water and then brine and dried over $Na_2SO_4$. Concentration of the solvents under reduced provided (S)-3-(tert-butoxycarbonyl)-4-(2,2-difluorobenzo[d][1,3]dioxol-5-yl)-2-oxobutyl acetate (1.10 g, 57% yield) as a white solid.

Step 4: (2S,3S)-3-(tert-butoxycarbonyl)-4-(2,2-difluorobenzo[d][1,3]dioxol-5-yl)-2-hydroxybutyl acetate A solution of (S)-3-(tert-butoxycarbonyl)-4-(2,2-difluorobenzo[d][1,3]dioxol-5-yl)-2-oxobutyl acetate (1100 mg, 2741 μmol) in 45 mL of ethanol cooled to 0° C. was added to lithium aluminumtri-tert-butoxyhydride (1 M in THF, 5481 μA 5481 μmol) in 15 mL of ethanol at −78° C. dropwise via cannula over 5 minutes. After stirring at −78° C. for 2 hours the reaction was quenched with 10 mL of 1 N HCl and the mixture was diluted with ethyl acetate (500 mL). The reaction was poured into 200 mL of water, the layers were separated and the aqueous layer was extracted with ethyl acetate (3×100 mL). The combined organics were washed with water, brine, and dried over sodium sulfate, filtered and concentrated to provide (2S,3S)-3-(tert-butoxycarbonyl)-4-(2,2-difluorobenzo[d][1,3]dioxol-5-yl)-2-hydroxybutyl acetate (1060 mg, 96% yield) as a white solid.

Step 5: (4S,5S)-tert-butyl 4-((2,2-difluorobenzo[d][1,3]-dioxol-5-yl)-methyl)-5-(hydroxymethyl)-2,2-dimethyloxazolidine-3-carboxylate To a solution of (2S,3S)-3-(tert-butoxycarbonyl)-4-(2,2-difluorobenzo[d][1,3]dioxol-5-yl)-2-hydroxybutyl acetate (1050 mg, 2603 μmol) in 5 mL of DMF was added 2-methoxypropene (872 μA 9111 μmol) and CSA (181 mg, 781 μmol). The mixture was stirred at rt overnight, and 91 mg of CSA and 0.872 mL of 2-methoxypropene were added. The reaction was stirred for 2 hours, then poured into ice-cold aqueous saturated sodium bicarbonate (150 mL) and extracted with ethyl acetate (3×50 mL). The combined organic layers were washed with water, brine, and dried over sodium sulfate. The derived yellow oil was taken up in 10 mL of methanol cooled to 0° C. and treated with potassium carbonate (1079 mg, 7809 μmol). After warming to rt over the course of 1 hour the reaction was diluted with ethyl acetate (25 mL) and poured in saturated ammonium chloride (50 mL). The aqueous layer was extracted with ethyl acetate (3×50 mL) and the combined organic layers were washed with water and then brine and dried over $Na_2SO_4$. Concentration of the solvents under reduced pressure and purification by silica gel provided (4S,5S)-tert-butyl 4-((2,2-difluorobenzo[d][1,3]dioxol-5-yl)methyl)-5-(hydroxymethyl)-2,2-dimethyloxazolidine-3-carboxylate as a colorless oil.

Example 5

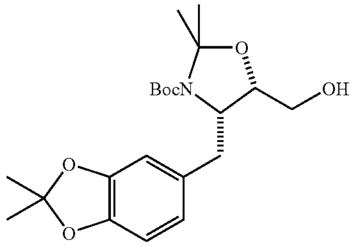

(4S,5S)-tert-Butyl 4-((2,2-dimethylbenzo[d][1,3]dioxol-5-yl)methyl)-5-(hydroxymethyl)-2,2-dimethyloxazolidine-3-carboxylate Step 1: (Z)-Methyl 2-(tert-butoxycarbonyl)-3-(2-methylbenzo[d][1,3]dioxol-5-yl)acrylate To a solution of methyl 2-(tert-butoxycarbonyl)-2-(dimethoxyphosphoryl)acetate (5255 mg, 17678 μmol) in 25 mL of DCM at 0° C. was added DBU (2665 μl, 17678 μmol) dropwise. To the mixture was then added a solution of 2,2-dimethylbenzo[d][1,3]dioxole-5-carbaldehyde (3000 mg, 16836 μmol) in 10 mL of DCM over 5 minutes so as to maintain internal temperature below 10° C. The reaction was warmed to rt and stiffed overnight before being diluted with DCM (25 mL) and poured in saturated ammonium chloride (100 mL). The aqueous layer was extracted with DCM (1×50 mL). The combined organic layers were washed with 10% aqueous sodium bicarbonate then water then brine and dried over $Na_2SO_4$. Concentration under reduced pressure and purification by silica gel provided (Z)-methyl 2-(tert-butoxycarbonyl)-3-(2,2-dimethylbenzo[d][1,3]dioxol-5-yl)acrylate (5005 mg, 85.1% yield) as a white solid.

Step 2: (S)-Methyl 2-(tert-butoxycarbonyl)-3-(2,2-dimethylbenzo[d][1,3]dioxol-5-yl)propanoate To a slurry of (Z)-methyl 2-(tert-butoxycarbonyl)-3-(2,2-dimethylbenzo[d][1,3]dioxol-5-yl)acrylate (5000 mg, 14311 μmol) in 30 mL of MeOH was added [Rh(duanphos)cod]$BF_4$ (101.1 mg, 143.1 μmol) followed by an additional 15 mL of methanol. The mixture was purged with hydrogen 3 times and then sealed at 50 psi of $H_2$. After 3 hours reaction the reaction was concentrated and purified by silica gel chromatography to provide (S)-methyl 2-(tert-butoxycarbonyl)-3-(2,2-dimethylbenzo[d][1,3]dioxol-5-yl)propanoate (5000 mg, 99.43% yield) as a colorless oil.

Step 3: (S)-2-(tert-Butoxycarbonyl)-3-(2,2-dimethylbenzo[d][1,3]dioxol-5-yl)propanoic acid To a solution of (S)-methyl 2-(tert-butoxycarbonyl)-3-(2,2-dimethylbenzo[d][1,3]dioxol-5-yl)propanoate (5000 mg, 14229 μmol) in 100 mL of THF at 0° C. was added lithium hydroxide (0.2 M, 28458 μl, 14229 μmol) over 10 minutes. After stirring at 0° C. for 1 hour the reaction was poured into a separatory funnel and 100 mL of water was added. The mixture was washed with 150 mL of ether, then acidified to pH 2-3- with 1 N HCl. Ethyl acetate was added, the layers were separated and the aqueous layer was extracted with ethyl acetate (3×100 mL). The combined organics were washed with water and then brine before being dried over sodium sulfate, filtered and concentrated to furnish (S)-2-(tert-butoxycarbonyl)-3-(2,2-dimethylbenzo[d][1,3]dioxol-5-yl) propanoic acid (4005 mg, 83% yield) as a colorless viscous oil.

Step 4: (S)-3-(tert-Butoxycarbonyl)-4-(2,2-dimethylbenzo[d][1,3]dioxol-5-yl)-2-oxobutyl acetate To a solution of (S)-2-(tert-butoxycarbonyl)-3-(2,2-dimethylbenzo[d][1,3]dioxol-5-yl)propanoic acid (4000 mg, 11857 μmol) in 100 mL of THF at 0° C. was added TEA (1653 μl, 11857 μmol) and isobutyl chloroformate (1551 μl, 11857 μmol). Reaction was stirred at 0° C. for 2 hours then filtered through a small frit of celite. The filtered solution was cooled to 0° C. and freshly prepared diazomethane (0.5 M in ether, 35570 μl, 17785 μmol) was added. The reaction solution was maintained at 0° C. for 1 hour then poured into saturated sodium bicarbonate 250 mL. The aqueous layer was extracted with ethyl acetate (3×100 mL). The combined organic layers were washed with water and then brine and dried over $Na_2SO_4$. Concentration under reduced pressure provided the diazo ketone as a yellow oil that was carried on without further purification. The diazo ketone was taken up in 100 mL of THF, cooled to 0° C. and treated with HBr (33 wt % in AcOH) (2147 μl, 11857 μmol). After stirring for 30 minutes potassium carbonate (2458 mg, 17785 μmol) and sodium acetate (9726 mg, 118565 μmol) were added and the THF was removed in vacuo. 25 mL of DMF was added and the reaction slurry was stirred at rt for 10 minutes, then diluted with ethyl acetate (50 mL) and poured into water (100 mL). The aqueous layer was extracted with ethyl acetate (2×100 mL) and the combined organic layers were washed with water and then brine and dried over $Na_2SO_4$. Concentration under reduced pressure and purification of the crude by silica gel chromatography (Analogix, 120 g) 0-25% ethyl acetate in hexanes provided (S)-3-(tert-butoxycarbonyl)-4-(2,2-dimethylbenzo[d][1,3]dioxol-5-yl)-2-oxobutyl acetate (3560 mg, 76% yield) as a slightly yellow oil.

Step 5: (2S,3S)-3-(tert-Butoxycarbonyl)-4-(2,2-dimethylbenzo[d][1,3]dioxol-5-yl)-2-hydroxybutyl acetate A solution of (S)-3-(tert-butoxycarbonyl)-4-(2,2-dimethylbenzo[d][1,3]dioxol-5-yl)-2-oxobutyl acetate (3270 mg, 8311 μmol) in 100 mL of ethanol was cooled to −78° C. and added to a solution of lithium aluminum tri-tert-butoxyhydride (16623 μl, 16623 μmol) in 45 mL of ethanol at −78 C dropwise via a cannula over 10 minutes. After stirring at −78° C. for 2 hours the reaction was quenched with 25 mL of 1 N HCl and diluted with ethyl acetate (500 mL). The mixture was poured into 200 mL of water, the layers were separated and the aqueous layer was extracted with ethyl acetate (3×100 mL). The combined organics were washed with water, brine, and dried over sodium sulfate and concentrated to provide (2S,3S)-3-(tert-butoxycarbonyl)-4-(2,2-dimethylbenzo[d][1,3]dioxol-5-yl)-2-hydroxybutyl acetate (3220 mg, 98% yield) as a white solid.

Step 6: (4S,5S)-tert-butyl 4-((2,2-dimethylbenzo[d][1,3]dioxol-5-yl)methyl)-5-(hydroxymethyl)-2,2-dimethyloxazolidine-3-carboxylate To a solution of (2S,3S)-3-(tert-butoxycarbonyl)-4-(2,2-dimethylbenzo[d][1,3]dioxol-5-yl)-2-hydroxybutyl acetate (1350 mg, 3414 μmol) in 5 mL of DMF was added 2-methoxyprop-1-ene (1961 μl, 20483 μmol) and ((1S,4R)-7,7-dimethyl-2-oxobicyclo[2.2.1]heptan-1-yl)methanesulfonic acid (397 mg, 1707 μmol). After stirring for 20 hours the reaction was poured into ice-cold aqueous saturated sodium bicarbonate (150 mL) and extracted with ethyl acetate (3×50 mL). The combined organic layers were washed with water, brine, and dried over sodium sulfate. The orange oil was taken up in 30 mL of methanol, cooled to 0° C. and treated with potassium carbonate (1415 mg, 10242 μmol). The reaction was allowed to warm to rt over the course of 1 hour and stirred for a total of 2 hours. The reaction was diluted with ethyl acetate (25 mL) and poured in saturated ammonium chloride 50 mL. The aqueous layer was extracted with ethyl acetate (3×50 mL). The combined organic layers were washed with water, brine dried over $Na_2SO_4$, filtered, concentrated under reduced pressure and purification of the resulting crude material by silica gel chromatography provided (4S,5S)-tert-butyl 4-((2,2-dimethylbenzo[d][1,3]dioxol-5-yl)methyl)-5-(hydroxymethyl)-2,2-dimethyloxazolidine-3-carboxylate as an orange foam.

Example 6 (9)

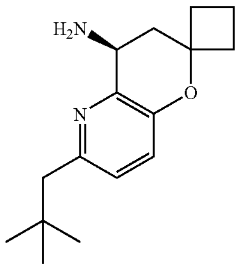

(4S)-2,2-Spirocyclobutan-6-neopentyl-3,4-dihydro-2H-pyrano[3,2-b]pyridin-4-amine Step 1: 5-(methoxymethoxy)-2-neopentylpyridine-N-oxide 5-(Methoxymethoxy)-2-neopentylpyridine (11.0 g, 52.6 mmol) was dissolved in $CH_2Cl_2$ (200 mL) to which mCPBA (18.1 g, 105 mmol) was added, and the mixture was stirred under $N_2$ for about 4 h. The mixture was quenched with 1M NaOH (200 mL) and stirring was continued vigorously for 10 min. The mixture was extracted with $CH_2Cl_2$ (2×200 mL), the combined organic layers were washed with saturated NaCl, dried ($Na_2SO_4$), and evaporated to give 5-(methoxymethoxy)-2-neopentylpyridine-N-oxide (11.8 g, 99.7% yield) as a brown oil which was used without purification in the next step.

Step 2: 3-(methoxymethoxy)-6-neopentylpicolinonitrile 5-(Methoxymethoxy)-2-neopentylpyridine-N-oxide (11.5 g, 51 mmol) was dissolved in $CH_2Cl_2$ (50 mL) to which benzoyl chloride (12 ml, 102 mmol) and (trimethylsilyl)formonitrile (14 ml, 102 mmol) were added. The mixture was stirred under $N_2$ 4 h, quenched with saturated $NaHCO_3$ (150 mL), and extracted with $CH_2Cl_2$ (3×100 mL). The combined organic layers were washed with saturated $NaHCO_3$ (2×50 mL), dried ($MgSO_4$), and evaporated to give the crude product as a brown oil, which was purified by ISCO (330 g $SiO_2$, 0-40% EtOAc/Hexane) to give 3-(methoxymethoxy)-6-neopentylpicolinonitrile (8.8 g, 74% yield) as a clear oil.

Step 3: 1-(3-(methoxymethoxy)-6-neopentylpyridin-2-yl)ethanone 3-(Methoxymethoxy)-6-neopentylpicolinonitrile (8.3 g, 35 mmol) was dissolved in THF (125 mL). The solution was cooled to 0° C. and methylmagnesium chloride (24 ml, 71 mmol) (3.0 M in $Et_2O$) was added. The reaction mixture stirred for 2 h at rt under $N_2$ then quenched with saturated $NH_4Cl$ (50 mL) and extracted with EtOAc (3×50 mL). The organic layer was dried over $MgSO_4$ and evaporated to give the crude product as a yellow oil. Purification of the crude residue by ISCO (40 g $SiO_2$, 0-40% EtOAc/Hexane) gave 1-(3-(methoxymethoxy)-6-neopentylpyridin-2-yl)ethanone (3.8 g, 43% yield) as a clear, light orange oil.

Step 4: 1-(3-hydroxy-6-neopentylpyridin-2-yl)ethanone

A solution of 1-(3-(methoxymethoxy)-6-neopentylpyridin-2-yl)ethanone (3.75 g, 15 mmol) in (2:1:1) 5 M HCl: i-PrOH:THF (100 mL) was stirred 16 h at rt. The mixture was concentrated to remove the THF and i-PrOH. The resulting solution consisting of the product in aqueous HCl was quenched by slow addition to a solution of saturated aqueous $NaHCO_3$ (500 mL) containing excess solid $NaHCO_3$ (28 g). The aqueous layer was extracted with $CH_2Cl_2$ (3×100 mL), the organic layers combined and washed with saturated aqueous NaCl (100 mL), dried ($MgSO_4$), and concentrated to give the crude product as a brown oil. The product was purified by ISCO (0-10% EtOAc/Hexanes) to give 1-(3-hydroxy-6-neopentylpyridin-2-yl)ethanone (1.98 g, 64% yield) as a clear, colorless oil.

Step 5: 2,2-spirocyclobutan-6-neopentyl-2,3-dihydropyrano[3,2-b]pyridin-4-one

A mixture of 1-(3-hydroxy-6-neopentylpyridin-2-yl)ethanone (1.90 g, 9167 μmol), pyrrolidine (2296 μl, 27501 μmol), and cyclobutanone (2570 mg, 36667 μmol) in $CH_3CN$ (20 mL) was heated in a 65° C. oil bath for 3 h. The mixture was cooled to rt, then diluted with EtOAc (25 mL), washed with $H_2O$, saturated aqueous $NH_4Cl$, saturated aqueous NaCl, dried ($MgSO_4$), and concentrated. Purification of the resulting crude material by ISCO (40 g $SiO_2$, 10-20% EtOAc/Hexanes) gave 2,2-spirocyclobutan-6-neopentyl-2,3-dihydropyrano[3,2-b]pyridin-4-one (710 mg, 29.9% yield) as a yellow solid.

Step 6: (4R)-2,2-spirocyclobutan-6-neopentyl-3,4-dihydro-2H-pyrano[3,2-b]pyridin-4-ol To a vial containing 2,2-spirocyclobutan-6-neopentyl-2,3-dihydropyrano[3,2-b]pyridin-4-one (710 mg, 2738 μmol) was added sodium formate (1862 mg, 27377 μmol) and tetrabutylammonium bromide (26.5 mg, 82.1 μmol). Toluene (5 mL) and $H_2O$ (2.5 mL) were added and the solution purged 3× with $N_2$, then with an Ar balloon for 15 min. [(1R,2R)-2-Amino-1,2-diphenyl-N-(p-tolylsulfonyl)ethylamido]chloro ($\eta^6$-p-cymene)ruthenium(II) (53.4 mg, 82.1 μmol) was added and the biphasic reaction was stirred at rt under Ar for 24 h. $H_2O$ (10 mL) was added and the reaction was extracted with $CH_2Cl_2$ (3×20 mL). The combined organic layers were dried ($Na_2SO_4$), and concentrated to give a brown oil, which was purified by ISCO (40 g $SiO_2$, 5-40% EtOAc/Hexane) gives (4R)-2,2-spirocyclobutan-6-neopentyl-3,4-dihydro-2H-pyrano[3,2-b]pyridin-4-ol (460 mg, 64.3% yield) as a clear oil.

Step 7: (4S)-4-azido-2,2-spirocyclobutan-6-neopentyl-3,4-dihydro-2H-pyrano[3,2-b]pyridine To a solution of (4R)-2,2-spirocyclobutan-6-neopentyl-3,4-dihydro-2H-pyrano[3,2-b]pyridin-4-ol (460 mg, 1760 μmol) in toluene (4 mL) is added diphenylphosphoryl azide (531 μl, 2464 μmol) then 1,8-diazabicyclo(5.4.0)-7-undecene (368 μl, 2464 μmol). The reaction mixture was stirred under $N_2$ at rt 23 h. The clear, light yellow solution first turned into a brown cloudy/opaque solution after 30 min. To speed up the reaction rate, the mixture was heated to 40° C. and stirred an additional 5 h. Water (20 mL) was added and the reaction mixture was extracted with EtOAc (3×20 mL). The combined organic layers were dried ($Na_2SO_4$), and concentrated to give the crude product as a brown oil, which was purified by ISCO (40 g $SiO_2$, 0-20% EtOAc/Hexane) gives (4S)-4-azido-2,2-spirocyclobutan-6-neopentyl-3,4-dihydro-2H-pyrano[3,2-b]pyridine (250 mg, 49.6% yield) as a white solid.

Step 8: (4S)-2,2-spirocyclobutan-6-neopentyl-3,4-dihydro-2H-pyrano[3,2-b]pyridin-4-amine A solution of (4S)-4-azido-2,2-spirocyclobutan-6-neopentyl-3,4-dihydro-2H-pyrano[3,2-b]pyridine (250 mg, 873 μmol) in methanol (10 mL) was purged with $N_2$ (3×), then palladium (260 mg, 244 μmol) (10 wt % on carbon) was added. The reaction was purged with $H_2$ (3×), then stirred at rt under $H_2$ 1.5 h. The suspension was filtered through a pad of Celite, MeOH wash (4×5 mL), and the solution concentrated to give the crude product (245 mg) as a white oily solid, which was purified by ISCO (12 g $SiO_2$, 0-10% MeOH/$CH_2Cl_2$) to give the title compound as a white solid.

Example 7

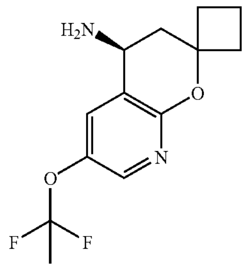

(4S)-6-(1,1-Difluoroethoxy)-2,2-spirocyclobutan-3,4-dihydro-2H-pyrano[2,3-b]pyridin-4-amine Step 1: (4S)-tert-Butyl-6-acetyl-2,2-spirocyclobutan-3,4-dihydro-2H-pyrano[2,3-b]pyridin-4-yl(allyl) carbamate To a solution of (4S)-tert-butyl 6-bromo-2,2-spirocyclobutan-3,4-dihydro-2H-pyrano[2,3-b]pyridin-4-yl(allyl)carbamate (8.1 g, 20 mmol) in $Et_2O$ (100 mL) at −78° C. was added tert-butyllithium (23 ml, 40 mmol) over 3 minutes. The reaction was allowed to stir 10 min. at −78° C., then acetaldehyde (4.5 ml, 79 mmol) was added, the reaction was then warmed to rt over 30 min, and quenched with $NH_4Cl$ (200 mL). The reaction was extracted with EtOAc (3×100 mL), the combined organic layers were washed with saturated NaCl (100 mL), dried ($Na_2SO_4$), and concentrated to give crude product as a dark yellow/orange oil. The crude was carried on into the next step without purification. To a solution of the crude product from above in $CH_2Cl_2$ (50 mL) at 0° C., was added sodium bicarbonate (6.64 g, 79.0 mmol) and Dess-Martin periodinane (10.5 g, 24.7 mmol) simultaneously. The ice bath was removed and the reaction was stirred for 2 h at rt, then quenched with saturated $Na_2SO_3$ (300 mL), extracted with $CH_2Cl_2$ (3×200 mL), and concentrated. The crude material was purified by ISCO (10-50% EtOAc/Hexane) to give the title compound (4.10 g, 55.7% yield over 2 steps) as a clear, light yellow oil.

Step 2: (4S)-1-(4-amino-2,2-spirocyclobutan-3,4-dihydro-2H-pyrano[2,3-b]pyridin-6-yl)ethanone To a 150 mL rbf with (4S)-tert-butyl 6-acetyl-2,2-spirocyclobutan-3,4-dihydro-2H-pyrano[2,3-b]pyridin-4-yl(allyl) carbamate (2.05 g, 5504 μmol) and $CH_2Cl_2$ (50 mL) was added 2,2,2-trifluoroacetic acid (5089 μl, 66048 μmol). The reaction was allowed to stir at RT for 5 h, then diluted with $CH_2Cl_2$ (50 mL). The mixture was washed with saturated $NaHCO_3$ (2×100 mL) and the organic layer degassed with Argon for 10 minutes. The degassed solution was treated with 1,3-dimethylpyrimidine-2,4,6(1H,3H,5H)-trione (2.21 g, 14154 μmol) and tetrakistriphenylphosphine palladium(0) (254 mg, 220 μmol) and stirred at rt for 24 hours. The reaction mixture was washed with NaOH (1N, 2×50 mL), and HCl (1N, 2×50 mL). The acidic aqueous layer was then basified to pH 14 with NaOH (5N, 25 mL) and extracted with DCM (3×50 mL). The combined organic layers were dried ($Na_2SO_4$) and concentrated to give (4S)-1-(4-amino-2,2-spirocyclobutan-3,4-dihydro-2H-pyrano[2,3-b]pyridin-6-yl) ethanone (810 mg, 63.4%) as a light yellow oil.

Step 3: (4S)-6-(1,1-difluoroethoxy)-2,2-spirocyclobutyl-3,4-dihydro-2H-pyrano[2,3-b]pyridin-4-amine To a 20 mL polyethylene vial was added (4S)-1-(4-amino-2,2-spirocyclobutan-3,4-dihydro-2H-pyrano[2,3-b]pyridin-6-yl)ethanone (410 mg, 1765 μmol) and HF/pyridine (1 mL). Xenon difluoride (359 mg, 2118 μmol) was added to the mixture followed by $CH_2Cl_2$ (1 mL). The reaction was stirred at rt 24 h, then quenched by slowly adding it to saturated $NaHCO_3$ (100 mL) with solid $NaHCO_3$ (5 g). The mixture was extracted with $CH_2Cl_2$ (3×50 mL). The combined organic layers were collected, dried ($Na_2SO_4$) and concentrated to give the crude product as a brown oil. The crude was purified by ISCO (2×12 g $SiO_2$ stacker, 0-8% MeOH/$CH_2Cl_2$) to give (4S)-6-(1,1-difluoroethoxy)-2,2-spirocyclobutyl-3,4-dihydro-2H-pyrano[2,3-b]pyridin-4-amine as an orange oil.

Example 8

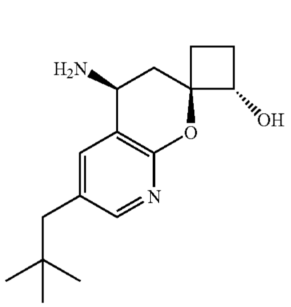

+

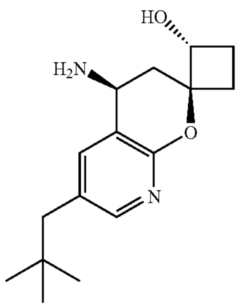

(1R,2S,4'S)-2-Hydroxy-3',4'dihydrospiro[cyclobutane-1,2'-pyrano[2,3-b]pyridin-4'-amine and (1S,2R,4'S)-2-hydroxy-3',4'dihydrospiro[cyclobutane-1,2'-pyrano[2,3-b]pyridin-4'-amine Step 1: (cis)-1-Allyl-2-(benzyloxy)cyclobutanol and (trans)-1-allyl-2-(enzyloxy)cyclobutanol To a RBF under argon was added 2-(benzyloxy)cyclobutanone (8.0 g, 45 mmol) and THF (100 mL). The reaction was cooled to 0° C. and allylmagnesium bromide (113 ml, 113 mmol) (1.0 M in $Et_2O$) was added over 20 min. The clear colorless solution turned into a tan solution with a white suspension. The ice bath was removed and the reaction warmed to rt and stirred 7 h. The reaction was quenched by slow addition to saturated aqueous $NH_4Cl$ (500 mL). The reaction was diluted with EtOAc (300 mL) and extracted. The aqueous layer was extracted with EtOAc (2×250 mL), the combined organic layers washed with saturated NaCl (250 mL), dried ($Na_2SO_4$), and concentrated to give a clear, light yellow oil, which was purified by ISCO (330 g $SiO_2$, 10-40% EtOAc/Hexane) gives the less polar isomer (cis)-1-allyl-2-(benzyloxy)cyclobutanol (4.0 g, 40% yield) followed by the more polar isomer (trans)-1-allyl-2-(benzyloxy)cyclobutanol (2.4 g, 24% yield) as a clear, colorless oils.

Step 2: ((1,2-cis)-1-Allyl-2-(benzyloxy)cyclobutoxy)(tert-butyl)dimethylsilane (Cis)-1-Allyl-2-(benzyloxy)cyclobutanol (4.00 g, 18.3 mmol) was dissolved in $CH_2Cl_2$ (100 mL) to which tert-butyldimethylsilyl trifluoromethanesulfonate (5.05 ml, 22.0 mmol) and N-ethyl-N-isopropylpropan-2-amine (3.99 ml, 22.9 mmol) were added. The reaction mixture was stirred at rt for 5 h. The reaction was quenched with 10% $NaCO_3$ (300 mL), and the aqueous layer was extracted with $CH_2Cl_2$ (2×100 mL). The combined organic layers were washed with saturated NaCl (50 mL), dried ($Na_2SO_4$), and concentrated to give a yellow oil, which was purified by ISCO (40 g $SiO_2$, 100% Hexane to give ((cis)-1-allyl-2-(benzyloxy)cyclobutoxy)(tert-butyl)dimethylsilane (5.38 g, 88.3% yield) as a clear, colorless oil.

Step 3: 2-((1,2-cis)-2-(Benzyloxy)-1-(tert-butyldimethylsilyloxy)cyclobutyl)acetaldehyde ((cis)-1-Allyl-2-(benzyloxy)cyclobutoxy)(tert-butyl)dimethylsilane (5.37 g, 16 mmol) was dissolved in t-butanol (30 mL, 319 mmol) and $H_2O$ (30 mL) followed by the addition of 4-methylmorpholine n-oxide (3.4 g, 29 mmol) in one portion. After the reactants dissolved, osmium tetroxide (5.1 mL, 0.40 μmol) was added and the reaction mixture was stirred at RT for 17 h. The reaction mixture was worked up by the addition of 6 g of sodium sulfite and allowed to stir for 1 h. The reaction mixture was extracted with ether and the organic phase was concentrated and used directly in the next step. The crude was dissolved in 1:1 t-BuOH/$H_2O$ (60 mL) and sodium periodate (6.2 g, 29 μmol) was added. The mixture was stirred for 3 h. Then $H_2O$ (100 mL) was added and the mixture was extracted with $Et_2O$ (3×100 mL). The combined organic layers were dried ($MgSO_4$) and concentrated. The crude was purified by ISCO (120 g $SiO_2$, 5-20% EtOAc/Hexane to give 2-((cis)-2-(benzyloxy)-1-(tert-butyldimethylsilyloxy)cyclobutyl)acetaldehyde (4.0 g, 74% yield) as a clear, colorless oil.

Step 4: 2-((1,2-cis)-2-(Benzyloxy)-1-(tert-butyldimethylsilyloxy)cyclobutyl)-1-(2-fluoro-5-neopentylpyridin-3-yl)ethanol To a flame-dried 250 mL rbf with 2,2,6,6-tetramethylpiperidine (3.41 ml, 20.1 mmol) was added THF (40 mL) and the solution is cooled to −78° C. n-Butyllithium (10.8 ml, 1.60 M, 17.2 μmol) was added dropwise and the reaction was warmed to 0° C. and stirred 5 min. The reaction was recooled to −78° C. and 2-fluoro-5-neopentylpyridine (2.40 g, 14.3 mmol) in THF (10 mL) was added and the reaction stirred 45 min at −78° C. Then 2-((cis)-2-(benzyloxy)-1-(tert-butyldimethylsilyloxy)cyclobutyl)acetaldehyde (4.00 g, 12.0 mmol) in THF (10 mL) was added dropwise. The reaction mixture was stirred 15 min at −78° C., then quenched by addition of saturated $NH_4Cl$ (50 mL), warmed to rt, diluted with $H_2O$ (50 mL) and extracted with $Et_2O$ (3×100 mL). The combined organic layers were washed with saturated NaCl (100 mL), dried ($Na_2SO_4$), and concentrated to give a crude product, which was purified by ISCO (120 g $SiO_2$, 0-20% EtOAc/Hexane) to give the title compound (5.18 g, 86.3%) as a 1:1 mixture of diastereomers, as a clear, light yellow oil.

Step 5: (1,2-cis)-2-(Benzyloxy)-1-(2-(2-fluoro-5-neopentylpyridin-3-yl)-2-hydroxyethyl)cyclobutanol To a flame-dried 100 mL rbf with 2-((1,2-cis)-2-(benzyloxy)-1-(tert-butyldimethylsilyloxy)cyclobutyl)-1-(2-fluoro-5-neopentylpyridin-3-yl)ethanol (5.18 g, 10 mmol) was added THF (10 mL) followed by TBAF (12 ml, 1.0 M in THF, 12 mmol). The reaction was stirred at rt for 30 min, then diluted with $H_2O$ (100 mL) and extracted with $Et_2O$ (3×50 mL). The combined organic layers were washed with saturated NaCl (100 mL), dried ($Na_2SO_4$) and concentrated to give a crude material, which was purified by ISCO (120 g $SiO_2$, 0-20% EtOAc/Hexane) to give (1,2-cis)-2-(benzyloxy)-1-(2-(2-fluoro-5-neopentylpyridin-3-yl)-2-hydroxyethyl)cyclobutanol (3.25 g, 81%) as a 1:1 mixture of diastereomers, a clear, light yellow oil.

Step 6: (1,2-cis)-2-Benzyloxy-6' neopentyl-3',4'dihydrospiro[cyclobutane-1,2'-pyrano[2,3-b]pyridin-4'-one To a flame-dried 100 mL rbf with (1,2-cis)-2-(benzyloxy)-1-(2-(2-fluoro-5-neopentylpyridin-3-yl)-2-hydroxyethyl)cyclobutanol (3.06 g, 7.9 μmol) was added THF (500 mL) followed by NaH (1.6 g, 39 mmol, 60% in mineral oil). The reaction was heated in a 60° C. oil bath under $N_2$ for 4 h, then cooled to rt and quenched with saturated $NH_4Cl$ (200 mL). The aqueous layer was extracted with EtOAc (3×100 mL), and the combined organic layers dried ($MgSO_4$) and concentrated to give the crude alcohol, which was used in the next step without purification. The crude material was dissolved in $CH_2Cl_2$ (100 mL) and Dess-Martin periodinane (3.3 g, 7.9 mmol) and sodium bicarbonate (0.66 g, 7.9 mmol) were added at the same time. The reaction was stirred for 2 h at rt. The reaction was quenched with saturated aqueous $Na_2SO_3$ (100 mL), extracted, then extracted with additional $CH_2Cl_2$ (2×100 mL). The combined organic layers were washed with saturated NaCl (100 mL), dried ($Na_2SO_4$), and concentrated to give the crude product as a yellow oil. Purification of the oil by ISCO (120 g $SiO_2$, 0-80% EtOAc/Hexane) gave the title compound (2.67 g, 93%) as a clear, light yellow oil.

Step 7: (1R,2S,4'R)-2-Benzyloxy-3',4' dihydrospiro[cyclobutane-1,2'-pyrano[2,3-b]pyridin-4'-ol To a stirred solution of (s)-2-methyl-cbs-oxazaborolidine (0.70 ml, 0.70 mmol) in THF (10 mL) at 0° C. was added borane-methyl sulfide complex (1.2 ml, 12 mmol) followed by a solution of (1,2-cis)-2-benzyloxy-6'neopentyl-3',4'dihydrospiro[cyclobutane-1,2'-pyrano[2,3-b]pyridin-4'-one (2.57 g, 7.0 mmol) in THF (20 mL) dropwise via syringe pump over about 2.8 h. The reaction was stirred an additional 30 min, then was quenched by dropwise addition (1 drop/10 sec) of 5 M HCl (25 mL) at 0° C. After 15 mL HCl was added, bubbling had ceased and the addition rate was increased as the ice bath was removed. The reaction was stirred an additional 2 h at rt. The reaction was recooled to 0° C. and neutralized with 5 M NaOH (27 mL). The mixture was then extracted with EtOAc (2×150 mL), washed with saturated aqueous NaCl (200 mL), dried ($MgSO_4$), and concentrated to give a yellow oil. Purification of the oil by ISCO (120 g $SiO_2$, 20% EtOAc/Hexane) gave a mixture of (1R,2S,4'R)-2-benzyloxy-6'-neopentyl-3',4' dihydrospiro[cyclobutane-1,2'-pyrano[2,3-b]pyridin-4'-ol (1.3 g, 50%) and (1S,2R, 4'R)-2-benzyloxy-6'-neopentyl-3',4'dihydrospiro[cyclobutane-1,2'-pyrano[2,3-b]pyridin-4'-ol (1.3 g, 50%) as a white foam.

Step 9: (1R,2S,4'S)-2-Benzyloxy-6'-neopentyl-3',4' dihydrospiro[cyclobutane-1,2'-pyrano[2,3-b]pyridin-4'-azide and (1S,2R,4'S)-2-benzyloxy-6'neopentyl-3',4' dihydrospiro[cyclobutane-1,2'-pyrano[2,3-b]pyridin-4'-azide To a solution of (1,2-cis,4'R)-2-benzyloxy-6'-neopentyl-3',4'dihydrospiro[cyclobutane-1,2'-pyrano[2,3-b]pyridin-4'-ol (2.6 g, 7.1 mmol) (1:1 mixture of 1,2-spirocyclobutyl diastereomers) in toluene (14 mL) was added diphenylphosphoryl azide (2.1 ml, 9.9 mmol) then 1,8-diazabicyclo(5.4.0)-7-undecene (1.5 ml, 9.9 mmol). The reaction was stirred under $N_2$ at rt for 18 h. The clear, light yellow solution turned into a yellow cloudy/opaque solution after 10 min. Water (100 mL) was added and the reaction mixture extracted with EtOAc (3×200 mL). The combined organic layers were washed with saturated NaCl (150 mL), dried ($MgSO_4$), and concentrated to give the crude product as a brown oil.

To a solution of the brown oil from above in 10:1 THF/$H_2O$ (40 mL) at 0° C. is added NaOH (2.85 ml, 14.3 mmol). After 5 min, trimethylphosphine (2.52 ml, 28.5 mmol) was added dropwise over 4 min. The ice bath was allowed to melt as the reaction warmed to rt and stirred a total of 18 h. The mixture was recooled to 0° C. and 5 N HCl (50 mL) was added. The resulting mixture was extracted with $CH_2Cl_2$ (3×100 mL), the combined organic layers were washed with 2.5 N HCl (2×50 mL). The combined aqueous layers were cooled to 0° C. and basified to pH 14 with 5 N NaOH (200 mL). The aqueous layer was extracted with $CH_2Cl_2$ (3×100 mL) the combined organic layers dried ($Na_2SO_4$), and concentrated to give 2.9 g crude product as a viscous yellow oil. Purification of the oil by ISCO (120 $SiO_2$, 0-10% MeOH/$CH_2Cl_2$ gradient elution) gave a 1:1 mixture of the title compounds (1.870 g, 71.6% yield) as a yellow oil.

Step 10: (1R,2S,4'S)-2-Hydroxy-6'-neopentyl-3',4'dihydrospiro[cyclobutane-1,2'-pyrano[2,3-b]pyridin-4'-amine and (1S,2R,4'S)-2-hydroxy-6'neopentyl-3',4'dihydrospiro[cyclobutane-1,2'-pyrano[2,3-b]pyridin-4'-amine To a solution of (1,2-cis,4'S)-2-benzyloxy-6'neopentyl-3',4'dihydrospiro[cyclobutane-1,2'-pyrano[2,3-b]pyridin-4'-azide (1.320 g, 3.6 mmol) in MeOH (50 mL) under Ar is added Pd Black (76.7 mg, 720 μmol). $H_2$ gas was bubbled though the suspension for 15 min. The reaction was then stirred at rt under an atmosphere of $H_2$ (balloon) for 48 h.

After 48 h, the $H_2$ atmosphere was replaced with $N_2$, and palldium hydroxide (506 mg, 720 μmol) was added, the reaction was sparged with $H_2$ and stirred for 24 h at rt. The $H_2$ atmosphere was replaced with $N_2$, and the suspension was filtered through a plug of Celite, washed with MeOH (3×50 mL), and the combined filtrates were concentrated in vacuo to give the crude product. Purification of the crude material by ISCO (120 g $SiO_2$, 0-30% $MeOH/CH_2Cl_2$ gradient elution) gave a mixture of (1R,2S,4'S)-2-hydroxy-6'-neopentyl-3',4'dihydrospiro[cyclobutane-1,2'-pyrano[2,3-b]pyridin-4'-amine (415 mg, 41.7% yield) and (1S,2R,4'S)-2-hydroxy-6'neopentyl-3',4'dihydrospiro[cyclobutane-1,2'-pyrano[2,3-b]pyridin-4'-amine as a yellow solid.

The following intermeciate materials were made using a procedure similar to that described in Examples 6, but with different starting materials.

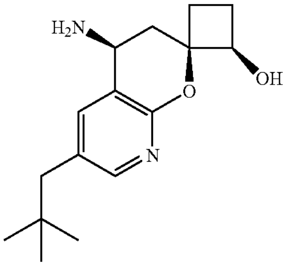

+

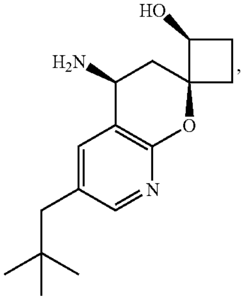

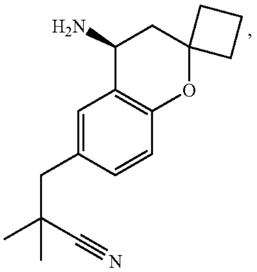

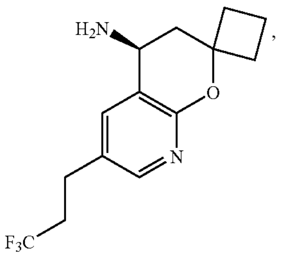

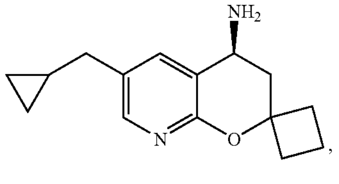

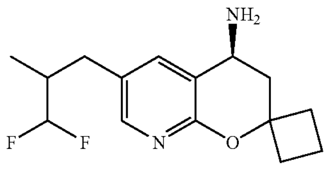

-continued

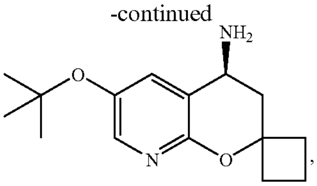

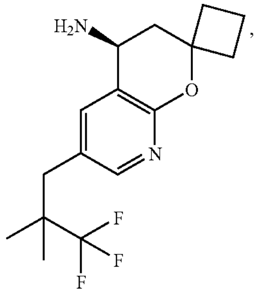

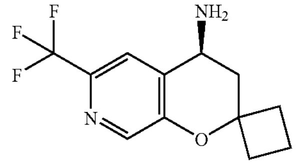

Example 9

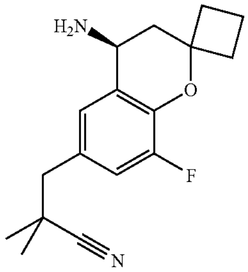

(S)-3-(4-Amino-8-fluoro-2,2-spirocyclobutyl-6-yl)-2,2-dimethylpropanenitrile

Step 1: 1-(5-Bromo-3-fluoro-2-hydroxyphenyl)ethanone

4-Bromo-2-fluorophenyl acetate (126 g, 540 mmol) in 1,2-dichlorobenzene (53 mL) was added dropwise to aluminum (III) chloride (72 g, 540 mmol) in 1,2-dichlorobenzene (64 mL) with vigorous stirring to give a red solution. The solution was heated to 120° C. for 60 hours, cooled, diluted with DCM, and added to 1N HCl at 0° C. The layers were separated and the aqueous layer was extracted with DCM. The combined organic layers were washed with 1N HCl, water, brine, and dried over sodium sulfate and concentrated. The crude material was taken up in hexanes and added to aqueous 1N NaOH at 0° C. The solid was collected and washed with hexanes. The aqueous filtrate and solid were acidified with concentrated HCl and extracted with ethyl acetate. The combined organic layers were washed with water, brine, dried over sodium sulfate, and concentrated. The crude solid was recrystallized from MeOH to afford the title compound (46 g, 37% yield).

Step 2: 6-Bromo-8-fluoro-2,2-spirocyclobutyl-4-one 1-(5-Bromo-3-fluoro-2-hydroxyphenyl)ethanone (15.00 g, 64 mmol), pyrrolidine (8 ml, 97 mmol), DIPEA (11 ml, 64 mmol), and cyclobutanone (9 ml, 129 mmol) were heated at 65° C. for 12 hours. After cooling, the reaction was diluted with EtOAc and washed with 1N HCl. The aqueous layer was extracted with EtOAc. The organic layers were combined, washed with water, brine, dried over sodium sulfate and concentrated. The residue was chromatographed on a silica gel column (10:1 Hexanes/Ether) to afford the title compound (9.73 g, 53% yield) as an orange solid. MS m/z: 285.0 (100%, M).

Step 3:
(R)-6-Bromo-8-fluoro-2,2-spirocyclobutyl-4-ol (s)-2-Methyl-cbs-oxazaborolidine, 1M in toluene (3.41 ml, 3.41 mmol) was added to a solution of borane-dimethyl sulfide (4.86 ml, 51.2 mmol) in 74 mL of toluene at 0° C. After stirring 20 minutes, 6-bromo-8-fluoro-2,2-spirocyclobutyl-4-one (9.73 g, 34.1 mmol) was added via syringe pump in 106 mL of toluene over 1.5 hour at −5° C. After stirring an additional 30 minutes at −5° C. the reaction was quenched by the addition of methanol and then 1N HCl. The mixture was extracted with ethyl acetate and the combined organic layers were washed 2× with 50% saturated ammonium chloride, brine, and dried over sodium sulfate. Concentration of the filtered organic layer afforded the title compound as yellow oil.

Step 4:
(S)-4-Azido-6-bromo-8-fluoro-2,2-spirocyclobutyl

Diphenyl azidophosphate (4.90 ml, 22.7 mmol) was added to a solution of (R)-6-bromo-8-fluoro-2,2-spirocyclobutyl-4-ol (4.35 g, 15.2 mmol) and DBU (3.43 ml, 22.7 mmol) in toluene (28 mL). The reaction was allowed to stir 48 hours and was filtered through a pad of silica gel and washed with EtOAc. Concentration of the EtOAc afforded the title compound.

Step 5:
(S)-6-Bromo-8-fluoro-2,2-spirocyclobutyl-4-amine

Raney nickel (2800), slurry, in water (0.4 g, 6 mmol) was added to (S)-4-azido-6-bromo-8-fluoro-2,2-spirocyclobutyl. (4.73 g, 15 mmol) dissolved in i-PrOH (150 mL). Hydrazine, monohydrate (5 ml, 76 mmol) was added and the reaction mixture was stirred 30 minutes before being filtered through a pad of Celite washing with ethanol. The EtOH solvent was concentrated, and the resulting crude material was purified by silica gel chromatography (20:1 DCM/MeOH (2M $NH_3$) to afford the title product. MS m/z: 269.0 (100%, M-17).

Step 6: (S)-tert-Butyl 6-bromo-8-fluoro-2,2-spirocyclobutyl-4-ylcarbamate (S)-6-Bromo-8-fluoro-2,2-spirocyclobutyl-4-amine (3.00 g, 10 mmol), TEA (2.2 ml, 16 mmol), and BOC-anhydride (3.0 g, 14 mmol) were stirred in DCM (30 mL) for 12 hrs and concentrated. The crude material was taken up in EtOAc and washed with saturated ammonium chloride, water, brine, dried over sodium sulfate and concentrated. The crude material was purified by recrystallization from methanol and water to afford the title product as a white solid.

Step 7: (S)-tert-Butyl allyl(6-bromo-8-fluoro-2,2-spirocyclobutyl-4-yl)carbamate (S)-tert-Butyl 6-bromo-8-fluoro-2,2-spirocyclobutyl-4-ylcarbamate (5.7 g, 15 mmol) was dissolved in DMF (70 mL) and cooled to 0° C. NaH (0.71 g, 18 mmol) was added carefully to the mixture and the solution was allowed to stir for 40 minutes. Allyl bromide (1.4 ml, 16 mmol) was added and the reaction mixture was stirred 45 minutes and then diluted with saturated aqueous ammonium chloride. Water was added and the solution was extracted with ether. The combined organic layers were washed with water, brine, dried over magnesium sulfate, filtered and concentrated to afford the title compound. MS m/z: 370.1 (100%, M-55).

Step 8: (S)-tert-Butyl allyl(8-fluoro-6-(hydroxymethyl)-2,2-spirocyclobutyl-4-yl)carbamate (S)-tert-Butyl allyl(6-bromo-8-fluoro-2,2-spirocyclobutyl-4-yl)carbamate (6.30 g, 15 mmol) was dissolved in diethyl ether (75 mL) and cooled to −78° C. tert-butyllithium (1.7 M) (19 ml, 33 mmol) was added dropwise to give a dark orange solution. After 20 minutes, DMF (13 ml, 163 mmol) was added and the solution was stirred for 45 minutes before being quenched by the addition of saturated ammonium chloride and water. The aqueous solution was extracted with EtOAc and the combined organic layers were washed with water, brine, dried over sodium sulfate and concentrated. The crude material was dissolved in 80 mL of MeOH, cooled to 0° C. and $NaBH_4$ (0.84 g, 22 mmol) was added to the cooled mixture. After stirring 40 minutes the reaction mixture and was quenched by addition of saturated ammonium chloride and water. The aqueous solution was extracted with EtOAc and the combined organic layers were washed with water, brine, dried over sodium sulfate and concentrated. The crude residue was purified by column chromatography (4:1 Hex/EtOAc) to give the title product.

Step 9: (S)-tert-Butyl allyl(6-(2-cyano-2-methylpropyl)-8-fluoro-2,2-spirocyclobutyl-4-yl)carbamate Dibromotriphenylphosphorane (4.28 g, 10.1 mmol) was added to a solution of (S)-tert-butyl allyl (8-fluoro-6-(hydroxymethyl)-2,2-spirocyclobutyl-4-yl)carbamate (3.48 g, 9.22 mmol) and N-ethyl-N-isopropylpropan-2-amine (1.61 ml, 9.22 mmol) in DCM (80 mL) at 0° C. After stirring 45 minutes at 0° C. and 30 minutes at ambient temperature, the reaction was concentrated and taken up in THF (40 mL). In a separate flask, diisopropylamine (8.21 ml, 58.1 mmol) was added to THF (90 mL) and the solution was cooled to −78° C. n-Butyllithium (22.1 ml, 55.3 mmol) was added and the solution was stirred 20 minutes at 0° C. Isobutyronitrile (4.96 ml, 55.3 mmol) was added and the yellow solution was stirred 40 minutes at 0° C. before the intermediate benzyl bromide described above in THF (40 mL) was added dropwise via addition funnel. The reaction was stirred at 0° C. and after 1 hour was complete. The reaction was quenched with saturated ammonium chloride and was extracted with EtOAc and the combined organic layers were washed with water, brine, dried over sodium sulfate and concentrated. The crude material was purified by silica gel chromatography (1.5:1 Hex/EtOAc) to afford the title product. MS m/z: 373.3 (100%, M-55).

Step 10: (S)-3-(4-(Allylamino)-8-fluoro-2,2-spirocyclobutyl-6-yl)-2,2-dimethylpropanenitrile (S)-tert-Butyl allyl (6-(2-cyano-2-methylpropyl)-8-fluoro-2,2-spirocyclobutyl-4-yl)carbamate (2.90 g, 6.8 mmol) and TFA (25 ml, 324 mmol) were stirred in DCM (50 mL) for 3 hours and concentrated. The crude product was taken up in DCM and 1 N NaOH and separated. The aqueous layer was extracted with DCM and the combined organic layers were washed with brine and dried over sodium sulfate. Concentration afforded the title product which was used without further purification. MS m/z: 329.3 (100%, M+1).

Step 11: (S)-3-(4-Amino-8-fluoro-2,2-spirocyclobutyl-6-yl)-2,2-dimethylpropanenitrile (S)-3-(4-(Allylamino)-8-fluoro-2,2-spirocyclobutyl-6-yl)-2,2-dimethylpropanenitrile was dissolved in degassed ($N_2$) DCM (40 mL) and 1,3-dimethylbarbituric acid (3.2 g, 20 mmol) was added. After two minutes, $Pd(PPh_3)_4$ (0.78 g, 0.68 mmol) was added and the reaction was stirred at ambient temperature for 12 hours. The reaction was diluted with DCM and 10% aqueous sodium carbonate and the layers were separated. The aqueous layer was extracted with DCM and the combined organic layers were washed with brine, dried over sodium sulfate and concentrated. The crude product was purified by silica gel chromatography (20:1 DCM/MeOH (2M $NH_3$)) to afford the title product. MS m/z: 289.2 (37%, M+1); 272.2 (100%, M-16).

Example 10

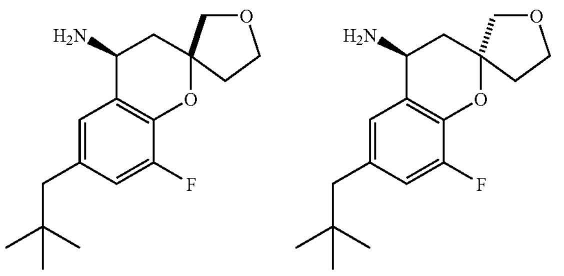

(S)-8-Fluoro-2,2-tetrahydrospirofuranyl-6-neopentylchroman-4-amine

Step 1: 6-Bromo-8-fluoro-2,2-tetrahydrospirofuranylchroman-4-one 1-(5-Bromo-3-fluoro-2-hydroxyphenyl)ethanone (0.200 g, 0.858 mmol), dihydrofuran-3(2H)-one (0.222 g, 2.57 mmol), and pyrrolidine (0.142 ml, 1.72 mmol) were dissolved in MeCN (0.5 mL) and heated in the microwave for 20 minutes fixed at 60° C. After cooling, the reaction was diluted with EtOAc and washed with 1N HCl. The aqueous layer was extracted with EtOAc. The organic layers were combined, washed with water, brine, dried over sodium sulfate, and concentrated. The crude product was purified by silica gel chromatography (1:4 EtOAc/hexanes) to afford the titled products. MS m/z: 301.0 (100%, M).

Step 2: (R)-6-Bromo-8-fluoro-2,2-tetrahydrospirofuranylchroman-4-ol (s)-2-Methyl-cbs-oxazaborolidine (0.767 ml, 0.767 mmol) was added to a solution of borane-methyl sulfide complex (1.09 ml, 11.5 mmol) in 16 mL of toluene at 0° C. After stirring 20 minutes, 6-bromo-8-fluoro-2,2-tetrahydrospirofuranylchroman-4-one (2.31 g, 7.67 mmol) was added via syringe pump in 23 mL of toluene over 1.5 hour at −5° C. After stirring an additional 30 minutes at −5° C. the reaction was quenched by the addition of MeOH and then 1N HCl. The mixture was extracted with ethyl acetate and the combined organic layers were washed twice with 50% saturated ammonium chloride, brine, and dried over sodium sulfate. Concentration of the filtered organic layer afforded the titled product as a yellow oil.

Step 3: (S)-4-Azido-6-bromo-8-fluoro-2,2-tetrahydrospirofuranylchroman

Diphenylphosphoryl azide (1.93 ml, 8.96 mmol) was added to a solution of (R)-6-bromo-8-fluoro-2,2-tetrahydrospirofuranylchroman-4-ol (1.81 g, 5.97 mmol) and DBU (1.35 ml, 8.96 mmol) in toluene (10 mL). The reaction was allowed to stir 48 hours and was filtered through a pad of silica gel with ethyl acetate. Concentration of the filtered organic layer afforded the titled products which were used without further purification.

Step 4. (S)-6-Bromo-8-fluoro-2,2-tetrahydrospirofuranylchroman-4-yl-amine

Raney nickel (2800, as a slurry in water) (0.19 g, 3.3 mmol) was added to (S)-4-azido-6-bromo-8-fluoro-2,2-tetrahydrospirofuranylchroman. (1.2 g, 3.7 mmol) dissolved in i-PrOH (50 mL). Hydrazine hydrate (1.1 ml, 18 mmol) was added and the reaction was stirred 30 minutes and then filtered through a pad of celite with ethanol, concentrated, and purified by silica gel chromatography (20:1 DCM/MeOH—NH3) to afford the titled products. MS m/z: 302.1 (5%, M); 285.1 (100%, M-17).

Step 5: (S)-8-Fluoro-2,2-tetrahydrospirofuranyl-6-neopentylchroman-4-amine

To zinc chloride, 0.5M solution in THF (31 ml, 15 mmol) was added 2,2-dimethylpropylmagnesium chloride, 1.0 M solution in diethyl ether (25 ml, 25 mmol) in a sealed tube and stirred 20 minutes. 1,1'-Bis(diphenylphosphino)ferrocene-palladium dichloride (0.2 g, 0.3 mmol) was added to the mixture followed by (S)-6-bromo-8-fluoro-2,2-tetrahydrospirofuranylchroman-4-amine (0.932 g, 3 mmol) in THF (8 mL). The tube was sealed and heated to 70° C. for 12 h. The reaction was cooled and diluted with DCM and an aq. solution of a 9:1 saturated ammonium chloride/ammonium hydroxide and the layers were separated. The aqueous layer was extracted with DCM, and the combined organic layers were washed with a 9:1 saturated ammonium chloride/ammonium hydroxide solution, water, brine, dried over sodium sulfate, and concentrated. Purification of the crude concentrate by silica gel chromatography (20:1 DCM/MeOH—NH3) afforded the title products.

Example 11

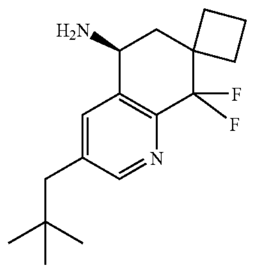

(S)-8,8-Difluoro-7,7-spirocyclobutyl-3-neopentyl-5,6,7,8-tetrahydroquinolin-5-amine Step 1: (S)-tert-butyl 7,7-spirocyclobutyl-3-neopentyl-5,6,7,8-tetrahydroquinolin-5-ylcarbamate (S)-7,7-Spirocyclobutyl-3-neopentyl-5,6,7,8-tetrahydroquinolin-5-amine (3.47 g, 13.4 mmol), TEA (2.81 ml, 20.1 mmol), and di-tert-butyl dicarbonate (2.93 g, 13.4 mmol) were stirred in DCM (60 mL) for 12 hrs and concentrated. The crude material was taken up in ethyl acetate and washed with saturated ammonium chloride, water, brine, dried over sodium sulfate, and concentrated. The crude material was purified by column chromotography (10:1 to 1:1 Hexanes/EtOAc) to afford the titled product.

Step 2: N-oxide of (S)-tert-butyl 7,7-spirocyclobutyl-3-neopentyl-5,6,7,8-tetrahydroquinolin-5-ylcarbamate m-Chloroperbenzoic acid (0.662 g, 2.30 μmol) was added to a solution of (S)-tert-butyl 7,7-spirocyclobutyl-3-neopentyl-5,6,7,8-tetrahydroquinolin-5-ylcarbamate (0.688 g, 1.92 mmol) in DCM (20 mL) and the solution was stirred 12 hrs before being diluted with aqueous saturated sodium bicarbonate and aqueous sodium thiosulfate. The mixture was stirred vigorously for 1.5 hrs then separated. The aqueous layer was extracted with DCM and the combined organic layers were washed with aqueous sodium thiosulfate, 10% sodium carbonate, water, brine, and dried over sodium sulfate. The organic layer was filtered and concentrated to afford the title product.

Step 3: S-tert-Butyl 8-hydroxy-7,7-spirocyclobutyl-3-neopentyl-5,6,7,8-tetrahydroquinolin-5-ylcarbamate The N-oxide from above (0.719 g, 1.92 mmol, Step 2) was dissolved in DCM (9 mL). Trifluoroacetic anhydride (1.33 ml, 9.60 mmol) was added and the reaction was refluxed for 2 hours and concentrated. The crude product was dissolved in THF (4.5 mL) and aqueous saturated sodium bicarbonate was added by pipette in dropwise fashion until no further bubbling was observed. The reaction was diluted with ethyl acetate and water and the layers were separated. The aqueous layer was extracted with ethyl acetate and the combined organic layers were washed with water, brine, and dried over sodium sulfate, filtered and concentrated. The crude product was purified by silica gel chromatography (25:1 DCM/MeOH) to afford the titled product. MS m/z: 375.3 (100%, M+1).

Step 4: (S)-tert-Butyl 7,7-spirocyclobutyl-3-neopentyl-8-oxo-5,6,7,8-tetrahydroquinolin-5-ylcarbamate (S)-tert-Butyl 8-hydroxy-7,7-spirocyclobutyl-3-neopentyl-5,6,7,8-tetrahydroquinolin-5-ylcarbamate (0.285 g, 0.761 mmol) and Dess-Martin Periodinane (0.968 g, 2.28 mmol) were stirred 12 hrs in DCM (7 mL). The reaction was diluted with ether and aqueous sodium thiosulfate and saturated aqueous sodium bicarbonate and stirred vigorously. The layers were separated and the aqueous layers were extracted with ether and the combined organic layers were washed with saturated aqueous sodium bicarbonate and water and concentrated. The residue was taken up in ethyl acetate and washed with brine, dried over sodium sulfate, and concentrated. Purification by silica gel chromatography (1:1 Hexanes/EtOAc) afforded the titled product. MS m/z: 373.3 (100%, M+1).

Step 5: (S)-tert-Butyl 8,8-difluoro-7,7-spirocyclobutyl-3-neopentyl-5,6,7,8-tetrahydroquinolin-5-ylcarbamate (S)-tert-Butyl 7,7-spirocyclobutyl-3-neopentyl-8-oxo-5,6,7,8-tetrahydroquinolin-5-ylcarbamate (0.183 g, 0.491 mmol) was dissolved in DCM (1.5 mL) and cooled to −78° C. DAST (0.130 ml, 0.983 mmol) was added and the reaction mixture was allowed to warm to RT over 12 hrs and stirred for four additional days. The reaction was diluted with DCM and aqueous 10% sodium carbonate and separated. The aqueous layer was extracted with DCM and the combined organic layers were washed with water, brine, and dried over sodium sulfate. Concentration of the filtered organic solvent afforded the titled product. MS m/z: 395.2 (100%, M+1).

Step 6: (S)-8,8-Difluoro-7,7-spirocyclobutyl-3-neopentyl-5,6,7,8-tetrahydroquinolin-5-amine (S)-tert-Butyl 8,8-difluoro-7,7-spirocyclobutyl-3-neopentyl-5,6,7,8-tetrahydroquinolin-5-ylcarbamate (0.194 g, 0.49 mmol) was stirred in a 2:1 solution of DCM and TFA (4.5 mL) for 3 hours and concentrated. The crude product was taken up in chloroform and 1N aq. NaOH and the layers were separated. The aqueous layer was extracted with chloroform and the combined organic layers were washed with brine, dried over sodium sulfate, filtered and concentrated. The crude product was purified by silica gel chromatography (30:1 DCM/MeOH—$NH_3$) to afford the titled product. MS m/z: 295.2 (100%, M+1).

Example 12

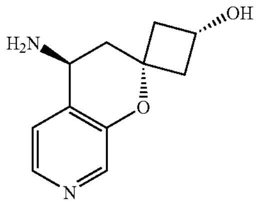

(1S,3S,4'S)-3-Hydroxy-3',4'-dihydrospiro[cyclobutane-1,2'-pyrano[2,3-c]pyridin-4'-amine Step 1: 3-(Methoxymethoxy)pyridine Pyridin-3-ol (25 g, 260 mmol) was added to a stirring mixture of NaH (11 g of a 60 wt % dispersion with mineral oil, 260 mmol) and DMF (350 mL) at 0° C. After 30 min, the reaction mixture was allowed to warm to RT, stirred for 90 min, and then chloromethoxymethane (20 mL, 260 mmol) was added. After 18 h, the reaction mixture was partitioned between ethyl acetate and saturated aqueous $NaHCO_3$. The layers were separated, the organic material was washed with saturated aqueous $NaHCO_3$, brine, dried ($Na_2SO_4$), filtered, and the filtrate was concentrated. The residue was dissolved with $CH_2Cl_2$, the solution was filtered through a plug of silica gel (sequential elution; 9:1→1:1 hexane-ethyl acetate), and the second filtrate was concentrated to give 10 g (27%) of 3-(methoxymethoxy)pyridine as a clear yellow oil.

Step 2: 1-(3-(Methoxymethoxy)pyridin-4-yl)ethanol

A solution of 3-(methoxymethoxy)pyridine (9.8 g, 70 mmol) and THF (40 mL) was added to a stirring mixture of tert-butyllithium (91 mL of a 1.7 M solution with pentane, 160 mmol) and THF (100 mL) at −78° C. After 1 h, acetaldehyde (9.9 mL, 180 mmol) was added, and the reaction mixture was stirred for 3 h and then warmed to RT. After 21 h, the reaction mixture was partitioned between ethyl acetate and saturated aqueous $NaHCO_3$, the layers were separated, the organic material was washed with saturated aqueous $NaHCO_3$, brine, dried ($Na_2SO_4$), filtered, and the filtrate was concentrated. The residue was purified by flash chromatography on silica gel (1:1 hexane-ethyl acetate) to afford 4.6 g (36%) of 1-(3-(methoxymethoxy)pyridin-4-yl)ethanol as a colorless solid.

Step 3: 1-(3-(methoxymethoxy)pyridin-4-yl)ethanone

Dess-Martin periodinane (18 g, 43 mmol) was added to a stirring mixture of 1-(3-(methoxymethoxy)pyridin-4-yl) ethanol (4.6 g, 25 mmol), $NaHCO_3$ (6.3 g, 75 mmol), and $CHCl_3$ (75 mL) at RT. After 24 h, 1.0 M aqueous $Na_2S_2O_3$ was added, the reaction mixture was stirred for 90 min, partitioned between ethyl acetate and 1.0 M aqueous $Na_2S_2O_3$, the layers were separated, the organic material was washed with 1.0 M aqueous $Na_2S_2O_3$, water, brine, dried ($Na_2SO_4$), filtered, and the filtrate was concentrated. The residue was purified by flash chromatography on silica gel (gradient elution; 2:1→1:1 hexane-ethyl acetate) to give 3.9 g (86%) of 1-(3-(methoxymethoxy)pyridin-4-yl)ethanone as a clear yellow-orange oil.

Step 4: (1S,3S)-3-tert-Butyldimethylsiloxy-3',4'-dihydrospiro[cyclobutane-1,2'-pyrano[2,3-c]pyridin-4'-one; and (1S,3R)-3-tert-Butyldimethylsiloxy-3',4'-dihydrospiro[cyclobutane-1,2'-pyrano[2,3-c]pyridin-4'-one 3-(tert-Butyldimethylsilyloxy)cyclobutanone (15 g, 77 mmol), 1-(3-Hydroxypyridin-4-yl)ethanone (10.5000 g, 77 mmol) and pyrrolidine (19 ml, 230 mmol) were dissolved in 500 ml $CH_3CN$ and stirred at 65° C. for 2 h. TLC analysis revealed the disappearance of the SM and the formation of a single new spot. The mixture was evaporated (100 ml residue) and partitioned between water and EtOAc. The phases were separated and the aqueous was extracted 3× with EtOAc. The combined organic extracts were dried over $MgSO_4$ and evaporated and the mixture was purified via glass col. chromatography. The title compounds (8.500 g, 35% yield) were obtained as a yellow solid (1:1 mixture of stereo isomers)

Step 5: (1S,3S,4'R)-3-tert-Butyldimethylsiloxy-3',4'-dihydrospiro[cyclobutane-1,2'-pyrano[2,3-c]pyridin-4'-ol; (1S,3R,4'R)-3-tert-Butyldimethylsiloxy-3',4'-dihydrospiro[cyclobutane-1,2'-pyrano[2,3-c]pyridin-4'-ol (1S,3S)-3-tert-Butyldimethylsiloxy-3',4'-dihydrospiro [cyclobutane-1,2'-pyrano[2,3-c]pyridin-4'-one and (1S,3R)-3-tert-Butyldimethylsiloxy-3',4'-dihydrospiro[cyclobutane-1,2'-pyrano[2,3-c]pyridin-4'-one (1:1 mixture of stereo isomers) (8.5000 g, 26.61 mmol) were dissolved in 150 ml toluene and 50 ml water was added. Ar gas was bubbled through the mixture for 15 min. Tetrabutylammonium bromide (0.2573 g, 0.7982 mmol), sodium formate (18.09 g, 266.1 mmol) and TPAP (0.5190 g, 0.7982 mmol) were added and the mixture was stirred for 14 h under an Ar atmosphere. The mixture was partitioned between EtOAc and water and the phases were separated. The aqueous was extracted 3 times with EtOAc, dried over $MgSO_4$ and evaporated. Glass col. chrom (10-50% EtOAc in hex.) provided the title compounds (6.630 g, 77.51% yield) as yellow oil. (1:1 mixture of stereo isomers). MS m/z: 322.2 (M+1).

Step 6: (1S,3S,4'S)-3-tert-Butyldimethylsiloxy-3',4'-dihydrospiro[cyclobutane-1,2'-pyrano[2,3-c]pyridin-4'-azide; (1S,3R,4'S)-3-tert-Butyldimethylsiloxy-3',4'-dihydrospiro[cyclobutane-1,2'-pyrano[2,3-c]pyridin-4'-azide (1S,3S,4'R)-3-tert-Butyldimethylsiloxy-3',4'-dihydrospiro[cyclobutane-1,2'-pyrano[2,3-c]pyridin-4'-ol, (1S,3R,4'R)-3-tert-Butyldimethylsiloxy-3',4'-dihydrospiro[cyclobutane-1,2'-pyrano[2,3-c]pyridin-4'-ol (1:1 mixture of stereo isomers) (6.6300 g, 20.62 mmol), diphenyl azidophosphate (6.667 ml, 30.93 mmol) and DBU (4.626 ml, 30.93 mmol) were dissolved in 40 ml $CH_2Cl_2$ and stirred over the weekend. Monitoring revealed that the starting materials were almost consumed and product formed, but still a large portion of the phosphonate ester remained. 40 ml of Water was added and the mixture was extracted 3 times with $Et_2O$, dried over $MgSO_4$ and evaporated. The crude product was used w/o purification in the next step. MS m/z: 347.2 (M+1).

Step 7: (1S,3S,4'S)-3-tert-Butyldimethylsiloxy-3',4'-dihydrospiro[cyclobutane-1,2'-pyrano[2,3-c]pyridin-4'-amine; (1S,3R,4'S)-3-tert-Butyldimethylsiloxy-3',4'-dihydrospiro[cyclobutane-1,2'-pyrano[2,3-c]pyridin-4'-amine The crude (1S,3S,4'S)-3-tert-Butyldimethylsiloxy-3',4'-dihydrospiro[cyclobutane-1,2'-pyrano[2,3-c]pyridin-4'-azide and (1S,3R,4'S)-3-tert-Butyldimethylsiloxy-3',4'-dihydrospiro[cyclobutane-1,2'-pyrano[2,3-c]pyridin-4'-azide (1:1 mixture of stereo isomers) from the previous reaction (6.9 g, 20 mmol) was dissolved in 200 ml THF and lithium aluminum hydride, 2M in THF (30 ml, 60 mmol) was added at 0° C. The mixture was stirred for 60 min and hydrolyzed with $Na_2SO_4$-$10H_2O$ until gas evolution had ceased. The mixture was filtered and evaporated and purified. (2-10% MeOH in $CH_2Cl_2$) glass col. chromatography provided the title compounds) as a yellow oil as a mixture of diastereomers. The diastereomers were separated by SFC. (1S,3S,4'S)-3-tert-Butyldimethylsiloxy-3',4'-dihydrospiro[cyclobutane-1,2'-pyrano[2,3-c]pyridin-4'-amine (1.200 g, 19% yield) and (1S,3R,4'S)-3-tert-Butyldimethylsiloxy-3',4'-dihydrospiro[cyclobutane-1,2'-pyrano[2,3-c]pyridin-4'-amine were obtained. MS m/z: 321.2 (M+1).

The following intermeciate materials were made using a procedure similar to that described in Examples 12, but with different starting materials.

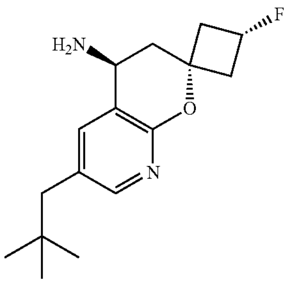

Example 13

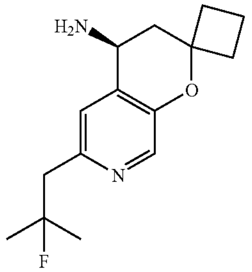

(4'S)-6'-(2-Fluoro-2-methylpropyl)-3',4'-dihydrospiro [cyclobutane-1,2'-pyrano[2,3-c]pyridin-4'amine

Step 1: 1-(5-(methoxymethoxy)pyridin-2-yl)-2-methylpropan-2-ol 5-(Methoxymethoxy)-2-methylpyridine (22.1500 g, 144.6 mmol) was dissolved in 1500 ml THF and cooled to −78° C. tert-Butyllithium (97.82 ml, 166.3 mmol) was added and the mixture was stirred for 15 min. Acetone, (42.52 ml, 578.4 mmol) was added and stirring of the mixture was continued for 15 min. The reaction was hydrolyzed with 300 ml $H_2O$ and extracted with 4 L EtOAc (2×). The combined organic extracts were dried over $MgSO_4$ and evaporated. Glas col. chrom (20-100% EtOAc provided the 2 products: 1-(5-(methoxymethoxy)pyridin-2-yl)-2-methylpropan-2-ol (7.5000 g, 24.55% yield) and 2-(5-(methoxymethoxy)-2-methylpyridin-4-yl)propan-2-ol (15.00 g, 49.10% yield). MS m/z: 212.0 (M+1).

Step 2: 2-(2-fluoro-2-methylpropyl)-5-(methoxymethoxy)pyridine 1-(5-(methoxymethoxy)pyridin-2-yl)-2-methylpropan-2-ol (7.600 g, 36.0 mmol) was dissolved in 200 ml $CH_2Cl_2$ and cooled to −78° C. DAST (9.51 ml, 72.0 mmol) was added drop wise to the solution and stirring was continued for 30 min The mixture was allowed to warm up to 0° C. and was hydrolyzed with $NaHCO_3$ (200 ml). Stirring was continued in the cold until gas evolution had ceased and the phases were separated.

The aqueous was extracted 2× with EtOAc and the combined organic layers were dried over $MgSO_4$ and evaporated. Glass col. Chromatography of the crude material provided 2-(2-fluoro-2-methylpropyl)-5-(methoxymethoxy)pyridine (5.80 g, 75.6% yield) as a pale yellow oil.

Step 3: 1-(2-(2-fluoro-2-methylpropyl)-5-(methoxymethoxy)pyridin-4-yl)ethanol 2,2,6,6-Tetramethylpiperidine (8.26 ml, 49.0 mmol) was dissolved with 270 ml THF and 1-butyllithium (14.1 ml, 35.4 mmol) was added at −78° C. The mixture was stirred for 10 min in an ice bath and cooled back to −78° C. A solution of 2-(2-fluoro-2-methylpropyl)-5-(methoxymethoxy)pyridine (5.8000 g, 27.2 mmol) in 20 ml THF was added dropwise and the reaction was stirred for 20 min. Acetylaldehyde (7.65 ml, 136 mmol) was added to the dark red solution and the color disappeared. Stirring was continued for 20 min and the mixture was hydrolyzed with 50 ml of water. The mixture was warmed to RT and extracted 3× with $CH_2Cl_2$ (300 ml each). The combined organic extracts were dried over $MgSO_4$ and evaporated and purified via glass col. chrom. (30-80% EtOAc in hex.) to provide 1-(2-(2-fluoro-2-methylpropyl)-5-(methoxymethoxy)pyridin-4-yl)ethanol a white solid. MS m/z: 258.2 (M+1).

Example 14

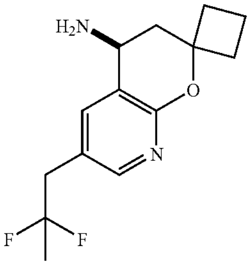

(4S)-6-(2,2-Difluoropropyl)-2,2-cyclobutyl-3,4-dihydro-2H-pyrano[2,3-b]pyridin-4-amine

Step 1: (4S)-tert-Butyl 6-(2-oxopropyl)-2,2-cyclobutyl-3,4-dihydro-2H-pyrano[2,3-b]pyridin-4-ylcarbamate Anhydrous, de-gassed THF (20 mL) was added to 2-(dicyclohexylphosphino)-2'-methylbiphenyl (1.2 g, 3.2 mmol) and tris(dibenzylideneacetone)dipalladium (0) chloroform adduct (1.4 g, 1.4 mmol), and the resulting solution was warmed to 45° C. and sparged with $N_2$. After 20 min, the reaction mixture was allowed to cool to RT, then added to a stirring, degassed mixture of (S)-tert-butyl 6-bromo-2,2-cyclobutyl-3,4-dihydro-2H-pyrano[2,3-b]pyridin-4-ylcarbamate (10 g, 27 mmol), finely ground potassium phosphate tribasic (14 g, 68 mmol), and acetone (100 mL, 1400 mmol) at RT, and the resulting mixture was sparged with $N_2$. After 20 min, the reaction mixture was heated at reflux for 24 h. The reaction mixture was allowed to cool to RT, filtered through a 0.45 μm Teflon filter, and the filtrate was concentrated. The residue was purified by flash chromatography on silica gel (gradient elution; 1:1→2:1 ethyl acetate-hexane) to afford 3.7 g (39%) of (S)-tert-butyl 6-(2-oxopropyl)-2,2-cyclobutyl-3,4-dihydro-2H-pyrano[2,3-b]pyridin-4-ylcarbamate as a yellow solid.

Step 2: (4S)-tert-Butyl 6-(2,2-difluoropropyl)-2,2-cyclobutyl-3,4-dihydro-2H-pyrano[2,3-b]pyridin-4-ylcarbamate Diethylaminosulfurtrifluoride (13 mL, 110 mmol) was added to a stirring solution of (S)-tert-butyl 6-(2-oxopropyl)-

2,2-cyclobutyl-3,4-dihydro-2H-pyrano[2,3-b]pyridin-4-ylcarbamate (3.7 g, 11 mmol), ethanol (0.12 mL, 2.2 mmol), and $CH_2Cl_2$ (55 mL) at RT. After 24 h, the reaction mixture was added to a rapidly stirring solution of aqueous 10% $Na_2CO_3$. After 1 h, ethyl acetate was added, the layers were separated, the organic material was washed sequentially with aqueous 10% $Na_2CO_3$ and brine, dried ($Na_2SO_4$), filtered, and the filtrate was concentrated. The residue was purified by flash chromatography on silica gel (49:1 $CH_2Cl_2$-methanol) to afford 1.8 g (46%) of (S)-tert-butyl 6-(2,2-difluoropropyl)-2,2-cyclobutyl-3,4-dihydro-2H-pyrano[2,3-b]pyridin-4-ylcarbamate as a yellow solid.

Step 3: (S)-6-(2,2-Difluoropropyl)-2,2-cyclobutyl-3,4-dihydro-2H-pyrano[2,3-b]pyridin-4-amine Hydrogen chloride (12 mL of a 4.0 M solution with 1,4-dioxane, 49 mmol) was added to a stirring solution of (4S)-tert-butyl 6-(2,2-difluoropropyl)-2,2-cyclobutyl-3,4-dihydro-2H-pyrano[2,3-b]pyridin-4-ylcarbamate (1.8 g, 4.9 mmol) and $CH_2Cl_2$ (49 mL) at RT. After 24 h, the reaction mixture was concentrated, the residue was partitioned between aqueous 10% $Na_2CO_3$ and EtOAc, the layers were separated. The organic layer was washed with aqueous 10% $Na_2CO_3$, brine, dried ($Na_2SO_4$), filtered, and the filtrate was concentrated to afford (S)-6-(2,2-difluoropropyl)-2,2-cyclobutyl-3,4-dihydro-2H-pyrano[2,3-b]pyridin-4-amine as a yellow oil.

Example 15

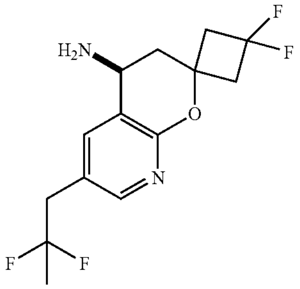

(S)-6-(2,2-Difluoropropyl)-2,2-(2',2'-difluorocyclobutyl)-3,4-dihydro-2H-pyrano[2,3-b]pyridin-4-amine Step 1: 1-(6-Fluoropyridin-3-yl)propan-2-one Anhydrous, de-gassed THF (20 mL) was added to 2-(dicyclohexylphosphino)-2'-methylbiphenyl (1.2 g, 3.2 mmol) and tris(dibenzylideneacetone)dipalladium (0) chloroform adduct (1.4 g, 1.4 mmol), and the resulting solution was warmed to 45° C. and sparged with $N_2$. After 20 min, the reaction mixture was allowed to cool to RT, then added to a stirring, degassed mixture of 5-bromo-2-fluoropyridine (4.8 g, 27 mmol), finely ground potassium phosphate tribasic (14 g, 68 mmol), and acetone (100 mL, 1400 mmol) at RT, and the resulting mixture was sparged with $N_2$. After 20 min, the reaction mixture was heated at reflux for 24 h, the reaction mixture was allowed to cool to room temperature, filtered through a 0.45 μm Teflon filter, and the filtrate was concentrated. The residue was purified by flash chromatography on silica gel (gradient elution; 4:1→2:1 hexane-ethyl acetate) to give 2.3 g (55%) of 1-(6-fluoropyridin-3-yl)propan-2-one as a brown oil.

Step 2: 5-(2,2-Difluoropropyl)-2-fluoropyridine

Diethylaminosulfurtrifluoride (9.8 mL, 75 mmol) was added to a stirring solution of 1-(6-fluoropyridin-3-yl)propan-2-one (2.3 g, 15 mmol), ethanol (0.18 mL, 3.0 mmol), and $CH_2Cl_2$ (60 mL) at RT. After 24 h, the reaction mixture was added to a rapidly stirring solution of aqueous 10% $Na_2CO_3$. After 1 h, ethyl acetate was added, the layers were separated, the organic layer was washed sequentially with aqueous 10% $Na_2CO_3$ and brine, dried ($Na_2SO_4$), filtered, and the filtrate was concentrated. The residue was purified by flash chromatography on silica gel (9:1 hexane-ethyl acetate) to afford 1.5 g (57%) of 5-(2,2-difluoropropyl)-2-fluoropyridine as a yellow-orange oil.

Step 3: (4S)-2-(1,3-Bis(tert-butyldimethylsiloxy)cyclobutyl)-1-(5-(2,2-difluoropropyl)-2-fluoropyridin-3-yl)-ethyl-((R)-tert-butylsulfinyl)amine Butyllithium (4.1 mL of a 2.5 M solution with toluene, 10 mmol) was added to a stirring solution of 2,2,6,6-tetramethylpiperidine (2.0 mL, 12 mmol) and THF (43 mL) at −78° C. After 5 min, the reaction mixture was raised above the cooling bath for 10 min, re-cooled to −78° C., and then a solution of 5-(2,2-difluoropropyl)-2-fluoropyridine (1.5 g, 8.6 mmol) and THF (8.6 mL) was added. After 30 min, a solution of 2-(1,3-bis(tert-butyldimethylsiloxy)cyclobutyl)acetaldehyde (R)-tert-butylsulfinylimine (4.4 g, 9.4 mmol) and THF (9.4 mL) was added. After 20 min, saturated aqueous $NaHCO_3$ was added, the reaction mixture was allowed to warm to RT, partitioned between saturated aqueous $NaHCO_3$ and ethyl acetate, the layers were separated, the organic layer was washed with saturated aqueous $NaHCO_3$, brine, dried ($NaSO_4$), filtered, and the filtrate was concentrated. The residue was purified by flash chromatography on silica gel (gradient elution; 4:1→3:1→2:1 hexane-ethyl acetate) to afford 2.9 g (53%) of (4S)-2-(1,3-bis(tert-butyldimethylsiloxy)cyclobutyl)-1-(5-(2,2-difluoropropyl)-2-fluoropyridin-3-yl)-ethyl-((R)-tert-butylsulfinyl)amine as a yellow solid.

Step 4: (S)-6-(2,2-difluoropropyl)-2,2-((R)-2'-hydroxy)cyclobutyl-3,4-dihydro-2H-pyrano[2,3-b]pyridin-4-amine and (S)-6-(2,2-difluoropropyl)-2,2-((S)-2'-hydroxy)cyclobutyl-3,4-dihydro-2H-pyrano[2,3-b]pyridin-4-amine Hydrogen fluoride (24 mL of a 70 wt % solution with pyridine, 1300 μmol) was added to (S)-2-(1,3-bis(tert-butyldimethylsiloxy)cyclobutyl)-1-(5-(2,2-difluoropropyl)-2-fluoropyridin-3-yl)-ethyl((R)-tert-butylsulfinyl) amine (1.7 g, 2.7 mmol) in Teflon™ reaction vessel, and the reaction mixture was heated at 80° C. After 48 h, the reaction mixture was added to aqueous 10% $Na_2CO_3$, the mixture was stirred vigorously for 2 h, ethyl acetate was added, the layers were separated, the organic material was washed with aqueous 10% $Na_2CO_3$, brine, dried ($Na_2SO_4$), filtered, and the filtrate was concentrated to afford 0.64 g (84%) of a mixture of (S)-6-(2,2-difluoropropyl)-2,2-((R)-2'-hydroxy)cyclobutyl-3,4-dihydro-2H-pyrano[2,3-b]pyridin-4-amine and (S)-6-(2,2-difluoropropyl)-2,2-((S)-2'-hydroxy)cyclobutyl-3,4-dihydro-2H-pyrano[2,3-b]pyridin-4-amine as a yellow solid.

Step 5: (S)-tert-butyl 6-(2,2-difluoropropyl)-2,2-((R)-2'-hydroxy)cyclobutyl-3,4-dihydro-2H-pyrano[2,3-b]pyridin-4-ylcarbamate and (S)-tert-butyl 6-(2,2-difluoropropyl)-2,2-((S)-2'-hydroxy)cyclobutyl-3,4-dihydro-2H-pyrano[2,3-b]pyridin-4-ylcarbamate Di-tert-butyl dicarbonate (0.64 g, 2.9 mmol) was added to a stirring solution of the (S)-6-(2,2-difluoropropyl)-2,2-((R)-2'-hydroxy)cyclobutyl-3,4-dihydro-2H-pyrano[2,3-b]pyridin-4-amine and (S)-6-(2,2-difluoropropyl)-2,2-((S)-2'-hydroxy)cyclobutyl-3,4-dihydro-2H-pyrano[2,3-b]pyridin-4-amine mixture (0.64 g, 2.3 mmol), $CH_2Cl_2$ (23 mL), and diisopropyethylamine (2.0 mL, 11 mmol) at RT. After 24 h, aqueous 10% $Na_2CO_3$ was added, the mixture was stirred vigorously for 1 h, EtOAc was added, the layers were separated, the organic layer was washed with aqueous 10% $Na_2CO_3$, brine, dried ($Na_2SO_4$), filtered, and the filtrate was concentrated. The residue was purified by flash chromatography on silica gel (19:1 $CH_2Cl_2$-methanol) to afford 0.32 g (37%) of a mixture of (S)-tert-butyl 6-(2,2-difluoropropyl)-2,2-((R)-2'-hydroxy)cyclobutyl-3,4-dihydro-2H-pyrano[2,3-b]pyridin-4-ylcarbamate and (S)-tert-butyl 6-(2,2-difluoropropyl)-2,2-((S)-2'-hydroxy)cyclobutyl-3,4-dihydro-2H-pyrano[2,3-b]pyridin-4-ylcarbamate as a yellow-brown solid.

Step 6: (S)-tert-butyl 6-(2,2-difluoropropyl)-2,2-cyclobutan-2'-one-3,4-dihydro-2H-pyrano[2,3-b]pyridin-4-ylcarbamate Dess-Martin periodinane (0.49 g, 1.2 mmol) was added to a mixture of (S)-tert-butyl 6-(2,2-difluoropropyl)-2,2-((R)-2'-hydroxy)cyclobutyl-3,4-dihydro-2H-pyrano[2,3-b]pyridin-4-ylcarbamate and (S)-tert-butyl 6-(2,2-difluoropropyl)-2,2-((S)-2'-hydroxycyclobutyl)-3,4-dihydro-2H-pyrano[2,3-b]pyridin-4-ylcarbamate (0.32 g, 0.83 mmol), $CH_2Cl_2$ (8.3 mL), and $NaHCO_3$ (0.21 g, 2.5 mmol) at RT. After 2 h, the reaction mixture was purified by flash chromatography on silica gel (1:1 hexane-ethyl acetate) to afford 0.24 g (75%) of (S)-tert-butyl 6-(2,2-difluoropropyl)-2,2-cyclobutan-2'-one-3,4-dihydro-2H-pyrano[2,3-b]pyridin-4-ylcarbamate as a colorless solid.

Step 7: (S)-tert-butyl 6-(2,2-difluoropropyl)-2,2-(2',2'-difluorocyclobutyl)-3,4-dihydro-2H-pyrano[2,3-b]pyridin-4-ylcarbamate Diethylaminosulfur trifluoride (0.41 mL, 3.1 mmol) was added to a stirring solution of (S)-tert-butyl 6-(2,2-difluoropropyl)-2,2-cyclobutan-2'-one-3,4-dihydro-2H-pyrano[2,3-b]pyridin-4-ylcarbamate (0.24 g, 0.63 mmol), $CH_2Cl_2$ (6.3 mL), and ethanol (7.3 L, 0.13 mmol) at RT. After 24 h, the reaction mixture was added to a stirring solution of aqueous 10% $Na_2CO_3$, the mixture was stirred for 1 h, partitioned between EtOAc and aqueous 10% $Na_2CO_3$, the layers were separated, the organic layer was washed with aqueous 10% $Na_2CO_3$, brine, dried ($Na_2SO_4$), filtered, and the filtrate was concentrated. The residue was purified by flash chromatography on silica gel (2:1 hexane-ethyl acetate) to give 0.15 g (59%) of (S)-tert-butyl 6-(2,2-difluoropropyl)-2,2-(2',2'-difluorocyclobutyl)-3,4-dihydro-2H-pyrano[2,3-b]pyridin-4-ylcarbamate as a colorless solid.

Step 8: (4S)-6-(2,2-difluoropropyl)-2,2-(2',2'-difluorocyclobutyl)-3,4-dihydro-2H-pyrano[2,3-b]pyridin-4-amine Hydrogen chloride (0.93 mL of a 4.0 M solution with 1,4-dioxane, 3.7 mmol) was added to a stirring solution of (S)-tert-butyl 6-(2,2-difluoropropyl)-2,2-(2',2'-difluorocyclobutyl)-3,4-dihydro-2H-pyrano[2,3-b]pyridin-4-ylcarbamate (0.15 g, 0.37 mmol) and $CH_2Cl_2$ (3.7 mL) at RT. After 24 h, the reaction mixture was concentrated, the residue was partitioned between aqueous 10% $Na_2CO_3$ and ethyl acetate, the layers were separated, the organic material was washed with aqueous 10% $Na_2CO_3$, brine, dried ($Na_2SO_4$), filtered, and the filtrate was concentrated to afford (S)-6-(2,2-difluoropropyl)-2,2-(2',2'-difluorocyclobutyl)-3,4-dihydro-2H-pyrano[2,3-b]pyridin-4-amine as a yellow solid.

Example 16

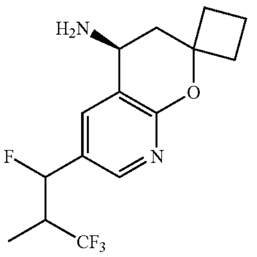

(4S)-2,2-Spirocyclobutyl-6-(1,3,3,3-tetrafluoro-2-methylpropyl)-3,4-dihydro-2H-pyrano(2,3-b)pyridine-4-amine Step 1: tert-Butyl allyl((S)-2,2-spirocyclobutyl-6-(3,3,3-trifluoro-1-hydroxy-2-methylpropyl)-3,4-dihydro-2H-pyrano(2,3-b)pyridine-4-yl)carbamate To a cooled (−78° C.) solution of (S)-tert-butyl allyl(6-bromo-2,2-spirocyclobutyl-3,4-dihydro-2H-pyrano(2,3-b)pyridine-4-yl)carbamate (8.70 g, 21 mmol) in diethylether was added tert-butyllithium (25 ml, 43 mmol) dropwise. After stirred for 15 min, the fresh distilled 3,3,3-trifluoro-2-methylpropanal (5.8 ml, 53 mmol) was added, and the reaction was stirred for 30 min, and then quenched with saturated NH4Cl. The resulted mixture was allowed to warm to RT and extracted with EtOAc (3×). The organic layers were combined, dried over Na2SO4, filtered and concentrated. The residue was purified on silica gel column to afford the title compound as a mixture of isomers (4.5 g, 46% yield) as light yellow oil. MS m/z: 457 (M+1).

Step 2: tert-Butyl allyl((S)-2,2-spirocyclobutyl-6-(1,3,3,3-tetrafluoro-2-methylpropyl)-3,4-dihydro-2H-pyrano(2,3-b)pyridine-4-yl)carbamate To a cooled (−78° C.) solution of tert-butyl allyl((S)-2,2-spirocyclobutyl-6-(3,3,3-trifluoro-1-hydroxy-2-methylpropyl)-3,4-dihydro-2H-pyrano(2,3-b)pyridine-4-yl)carbamate (1.24 g, 2.7 mmol) in toluene was added (diethylamino)sulfur trifluoride (0.54 ml, 4.1 mmol) via a syringe. The reaction was stirred for 50 min, then quenched with saturated $NH_4Cl$ (10 ml) and warmed to RT. The layers were separated. The aqueous layer was extracted with EtOAc (2×20 ml). The organic layers were combined, dried over $Na_2SO_4$, filtered and concentrated. The crude residue was purified on a silica gel column (10-15% EtOAc/hexane) to afford the title compound as a mixture of isomers as colorless oil. MS m/z: 459 (M+1).

Step 3: (4S)—N-Allyl-2,2-spirocyclobutyl-6-(1,3,3,3-tetrafluoro-2-methylpropyl)-3,4-dihydro-2H-pyrano(2,3-b)pyridine-4-amine To a solution of tert-butyl allyl((S)-2,2-spirocyclobutyl-6-(1,3,3,3-tetrafluoro-2-methylpropyl)-3,4-dihydro-2H-pyrano(2,3-b)pyridine-4-yl)carbamate (430 mg, 938 μmol) in MeOH was added hydrogen chloride 4.0 m in 1,4-dioxane (2.0 ml, 8000 μmol). The reaction was stirred for 2 days (over the weekend) at RT, then concentrated and neutralized with 10% $Na_2CO_3$ and extracted with DCM (3×). The organic layers were combined, dried over $Na_2SO_4$ and filtered. The filtrate was concentrated and dried in vacuum to afford the title compound as a mixture of isomers as a light yellow oil. MS+ m/z: 359 (M+1).

Step 4: (4S)-2,2-Spirocyclobutyl-6-(1,3,3,3-tetrafluoro-2-methylpropyl)-3,4-dihydro-2H-pyrano(2,3-b)pyridine-4-amine The crude product from step 3 above was dissolved in $CH_2Cl_2$ (10 ml) to which 1,3-dimethylpyrimidine-2,4,6(1H,3H,5H)-trione (439 mg, 2814 μmol) was added. The mixture was purged with $N_2$ gas for 10 min and tetrakis(triphenylphosphine)palladium (0) (54 mg, 47 μmol) was added. The reaction was heated at 40° C. for 3 h, then cooled and diluted with DCM and washed with 10% $Na_2CO_3$ (2×). The aqueous layer was back extracted with EtOAc (2×). The organic layers were combined, dried over $Na_2SO_4$, filtered and concentrated. The residue was dried in vacuum to afford the title compound as mixture of isomers as a yellow oil. MS m/z: 319 (M+1).

The following intermeciate materials were made using a procedure similar to that described in Examples 16, but with different starting materials.

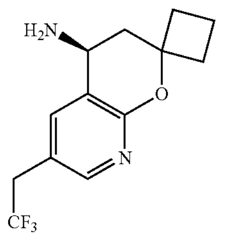

Example 17

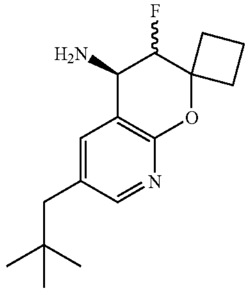

6-(2',2'-Dimethylpropyl)-2,2-spirocyclobutyl-3-fluoro-3,4-dihydro-2H-pyrano[2,3-b]pyridin-4-amine Step 1: (±) 6-Bromo-2,2-spirocyclobutyl-3-fluoro-3,4-dihydro-2H-pyrano[2,3-b]pyridin-4-one A mixture of 6-bromo-2,2-spirocyclobutyl-3,4-dihydro-2H-pyrano[2,3-b]pyridin-4-one (4.9 g, 18 mmol) and SLECTFLUOR (7.1 g, 20 mmol) in 40 ml of anhydrous MeOH was heated at 110-130° C. in a pressure bottle for 16 h. The mixture was cooled down and the solids were filtered off The filtrate was concentrated to give an oil which was purified by silica gel chromatography using EtOAc-Hexanes (0-12%) to give the tile compound as a clear oil which solidified upon drying.

Step 2: (±) 6-Bromo-2,2-spirocyclobutyl-3-fluoro-3,4-dihydro-2H-pyrano[2,3-b]pyridin-4-yl-(S)-tert-butylsulfinylimine A solution of (±) 6-Bromo-2,2-spirocyclobutyl-3-fluoro-3,4-dihydro-2H-pyrano[2,3-b]pyridin-4-one (3.0 g, 10 mmol) and (S)-2-methylpropane-2-sulfinamide (2.5 g, 21 mmol) in 5 ml of THF was treated with tetraethoxytitanium (8.7 ml, 42 mmol) at rt for 18 h. The reaction mixture was diluted with 100 ml of EtOAc and the resulting solution was added dropwise to 150 ml of sat. aq. $NaHCO_3$. White precipiates formed, and the mixture was stirred at rt vigorously for 1 h. The EtOAc layer was carefully decanted; the rest of mixture was filtered through a celite pad with $Na_2SO_4$. The celite pad was washed with 150 ml of EtOAc. The filtrates were combined and the EtOAc layer was separated. All organic layers were combined, dried ($Na_2SO_4$) and concentrated to give an oil that was purified by Isco (0-30% EtOAc in hexanes) to give the title compound as a yellow foam.

Step 3: (4R)-6-Bromo-2,2-spirocyclobutyl-3-fluoro-3,4-dihydro-2H-pyrano[2,3-b]pyridin-4-amine A solution of (±) 6-Bromo-2,2-spirocyclobutyl-3-fluoro-3,4-dihydro-2H-pyrano[2,3-b]pyridin-4-yl-(S)-tert-butylsulfinylimine from Step 2 (2.55 g, 6.6 mmol) in 20 ml of THF:$H_2O$ (98:2) at −50° C. was treated with sodium borohydride (0.74 g, 20 mmol) and the resulting mixture was stirred and warmed up to rt over 2 h, and then stirred overnight. The solvents were then removed, The crude residue was triturated with DCM, washed with sat. aq. $NaHCO_3$ (2×75 ml), dried over $Na_2SO_4$ and concentrated to give the title compound as an oil.

Step 4: (4R)-tert Butyl 6-Bromo-2,2-spirocyclobutyl-3-fluoro-3,4-dihydro-2H-pyrano[2,3-b]pyridin-4-carbamate A solution of (4R)-6-Bromo-2,2-spirocyclobutyl-3-fluoro-3,4-dihydro-2H-pyrano[2,3-b]pyridin-4-amine (1.23 g, 4.3 mmol) in 15 ml of dry DCM was treated with Boc anhydride (4.3 ml, 4.3 mmol) at rt overnight. The reaction solvent was removed and the resulting crude residue was purified by ISCO (0-20% EtOAc on hexanes) to give the titled compound.

Step 5: (4R)-6-(2'2'-dimethylpropyl)-2,2-spirocyclobutyl-3-fluoro-3,4-dihydro-2H-pyrano[2,3-b]pyridin-4-amine To a 50 mL RBF was added (4R)-tert butyl 6-bromo-2,2-spirocyclobutyl-3-fluoro-3,4-dihydro-2H-pyrano[2,3-b]pyridin-4-carbamate (580 mg, 1498 μmol), dioxane (10 mL).

The solution was degassed with $N_2$ for 10 minutes, and Pd catalyst (53 mg, 75 μmol) was added to the solution. A solution of neopentylzinc(II) iodide, in THF (8.0 ml, 4000 μmol) was then added and the reaction mixture was stirred at RT under $N_2$ for 16 hours. The reaction mixture was quenched with water (20 mL) and acidified to pH 2 with 1N HCl. The mixture was extracted with EtOAc (2×40 mL). The combined organic layers were washed with brine and concentrated in vacuo to give a dark brown oil, which was then treated with MeOH (30 mL) and HCl (4M in dioxane, 10 mL) and stirred overnight. The material was concentrated in vacuo and taken up in DCM (5% MeOH was added to improve solubility), and extracted with 1N HCl (2×20 mL). The combined acidic aqueous layers were washed with DCM (20 mL), neutralized with sat'd $NaHCO_3$ and extracted with DCM (3×20 mL). The combined organic layers were concentrated in vacuo to give the title compound.

Example 18

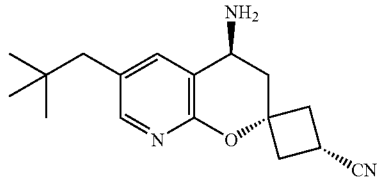

(4S)-6-Neopenyl-[(2,2-spirocyclobutyl)-3'-cis-cyano)]-2,3-dihydropyrano[2,3-b-]pyridin-4-amine Step 1: 3-Cyanocyclobutanone To a stirred mixture of 3-methylenecyclobutanecarbonitrile (5.0 g, 54 mmol) and ruthenium trichloride hydrate (0.086 ml, 1.2 mmol) in DCM/MeCN/$H_2O$ (215/215/315 ml) was added sodium meta periodate (12 ml, 225 mmol) in several portions (30 min.). The reaction mixture was slowly warmed to RT and stirred in 3 h. The precipitated solid was filtered off The filtrate was extracted with DCM (3×); dried over $MgSO_4$, concentrated and filtered through a short plug of silical gel, concentrated, to give the title compound as a light brown oil, which solidified upon standing at rt.

Step 2: 3-(2-(5-Bromo-2-methoxypyridin-3-yl)-2-oxoethylidene)cyclobutanecarbonitrile A mixture of lithium (Z)-1-(5-bromo-2-methoxypyridin-3-yl)-2-(dimethoxyphosphoryl)ethenolate (2.0 g, 5.8 mmol) and 3-oxocyclobutanecarbonitrile (1.1 g, 12 mmol) in p-dioxane (6 ml) was heated at 120° C. by Microwave in 1 h. The mixture was cooled, taken up in $H_2O$, extracted with EtOAc (3×), dried over $MgSO_4$, concentrated to provide the title compound. MS (m+1): 307.0.

Step 3: 6-Bromo-[(2,2-spirocyclobutyl)-3'-cyano)]-2,3-dihydropyrano[2,3-b-]pyridine-4-one A mixture of 3-(2-(5-bromo-2-methoxypyridin-3-yl)-2-oxoethylidene) cyclobutanecarbonitrile (3.4 g, 11 mmol), sodium iodide (1.8 ml, 44 mmol), and chlorotrimethyl silane (5.6 ml, 44 mmol) in MeCN (40 ml) was stirred at rt for 24 h, concentrated, taken up in $H_2O$, extracted with DCM (3×), washed with saturated $NH_4Cl$, brine, dried over $MgSO_4$, concentrated and purified by ISCO (20% EtOAc/Hexanes) to give the title compound as a yellow solid.

Step 4: (4R)-6-Bromo-[(2,2-spirocyclobutyl)-3'-cyano)]-2,3-dihydropyrano[2,3-b-]pyridine-4-ol To a stirred solution of (S)-2-methyl-CBS-oxazaborolidine (1M in toluene; 1.0 ml, 1.0 mmol) in toluene (5 ml) was added a solution of borane-methyl sulfide complex (0.5 ml, 5 mmol) in toluene (20 ml) and a solution of 6-bromo-[(2,2-spirocyclobutyl)-3'-cyano)]-2,3-dihydropyrano[2,3-b-]pyridine-4-one (1.40 g, 5 mmol) in toluene (20 ml) in 30 min at 0° C. The reaction mixture was stirred for another 15 min. then slowly quenched with 10% aq. HCl, extracted with EtOAc (3×), washed with $NaHCO_3$, brine, dried over $MgSO_4$, concentrated to give the title compound as a light yellow solid. MS (m+1): 296.1

Step 5: (4R)-6-Bromo-4-tert-butyldimethylsilyloxo-[(2,2-spirocyclobutyl)-3'-cyano)]-2,3-dihydropyrano[2,3-b-]pyridine To a stirred mixture of (4R)-6-bromo-[(2,2-spirocyclobutyl)-3'-cyano)]-2,3-dihydropyrano[2,3-b-]pyridine-4-ol (5.7 g, 19 mmol) and 1H-imidazole (22 ml, 193 mmol) in DMF (70 ml) was added tert-butylchlorodimethylsilane (15 g, 97 mmol). The reaction mixture was stirred at rt in 24 h, added water, extracted with ether (3×), dried over $MgSO_4$, concentrated and purified by ISCO (15% EtOAc/Hexanes) to give the title compound. MS (m+1): 410.4.

Step 6: (4R)-6-(2'2-dimethylpropyl)-4-tert-butyldimethylsilyloxo-[(2,2-spirocyclobutyl)-3'-cyano)]-2,3-dihydropyrano[2,3-b-]pyridine To a stirred solution of neopentylmagnesium chloride (1M, 15 ml, 15 mmol) at 0° C. was added dropwise a solution of zinc(II) chloride (8 ml, 8 mmol). The mixture was gradually warmed to rt in 30 min. $PdCl_2(dppf)_2$ (0.2 g, 0.2 mmol) and a solution of (4R)-6-bromo-4-tert-butyldimethylsilyloxo-[(2,2-spirocyclobutyl)-3'-cyano)]-2,3-dihydropyrano[2,3-b-]pyridine (1.56 g, 4 mmol) in THF (20 ml) were successively added to the mixture. The reaction mixture was stirred at 40° C. overnight, then cooled, quenched with saturated $NH_4Cl$, extracted with EtOAc, dried over $MgSO_4$, concentrated to provide the title compound. MS (m+1): 401.6.

Step 7: (4R)-6-Neopenyl-[(2,2-spirocyclobutyl)-3'-cis-cyano)]-2,3-dihydropyrano[2,3-b-]pyridine-4-ol and (4R)-6-neopenyl-[(2,2-spirocyclobutyl)-3'-trans-cyano)]-2,3-dihydropyrano[2,3-b-]pyridine-4-ol To a stirred solution of (4R)-6-neopentyl-4-tert-butyldimethylsilyloxo-[(2,2-spirocyclobutyl)-3'-cyano)]-2,3-dihydropyrano[2,3-b-]pyridine (1.5 g, 4 mmol) in THF (10 ml) was added tetrabutylammonium fluoride, 1.0M in THF (7 ml, 7 mmol). The reaction mixture was stirred in 2 h, quenched with $H_2O$, extracted with EtOAc, dried over $MgSO_4$, concentrated and purified by ISCO (40% EtOAc/Hexanes with 120 g column) to separate the cis- and trans-isomers of the title compound. MS (m+1): 287.4.

Step 8: (4S)-4-Azido-6-neopenyl-[(2,2-spirocyclobutyl)-3'-cis-cyano)]-2,3-dihydropyrano[2,3-b-]pyridine To a stirred solution of (4R)-6-neopenyl-[(2,2-spirocyclobutyl)-3'-cis-cyano)]-2,3-dihydropyrano[2,3-b-]pyridine- 4-ol (1.05 g, 3.67 mmol) in toluene (30 ml) was added DPPA (1.03 ml, 4.77 mmol) dropwise. After stirring for 15 min., DBU (0.713 ml, 4.77 mmol) was slowly added, and the reaction mixture was stirred at RT for 16 h. $H_2O$ was added and the mixture was extracted with EtOAc (3×), washed with brine, dried over $MgSO_4$, concentrated to give the title compound as a brown oil. MS (m+1): 312.4.

Step 9: (4S)-6-Neopenyl-[(2,2-spirocyclobutyl)-3'-cis-cyano)]-2,3-dihydropyrano[2,3-b-]pyridin-4-amine A mixture of (4S)-4-azido-6-neopenyl-[(2,2-spirocyclobutyl)-3'-cis-cyano)]-2,3-dihydropyrano[2,3-b-]pyridine (3 g, 10 mmol) and triphenylphosphine (3 g, 10 mmol) in THF (20 ml) was stirred at RT in 2 h, 3 ml of $H_2O$ was added and heated at 80° C. in 4 h. 40 ml of 10% aq. HCl was added and the mixture was heated for 10 min. at 80° C., then cooled and extracted with toluene, (discarded). The acidic aqueous layer was neutralized with solid $Na_2CO_3$, extracted with DCM (3×), dried over $MgSO_4$, purified by ISCO (3% MeOH/DCM) to give the title compound as a yellow foam. MS (m+1): 286.4.

The following intermeciate materials were made using a procedure similar to that described in Examples 18, but with different starting materials.

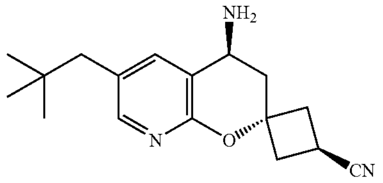

Example 19

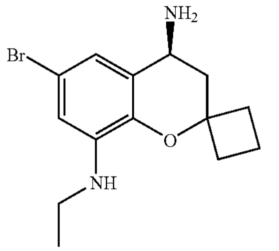

(S)-6-Bromo-$N^8$-ethyl-2,2,-spirocyclobutyl-3,4-dihydro-2H-chromene-4,8-diamine Step 1: 1-(3-amino-5-bromo-2-hydroxyphenyl)ethanone A mixture of 1-(5-bromo-2-hydroxy-3-nitrophenyl)ethanone (25 g, 96 mmol), iron (27 g, 481 mmol), and $NH_4Cl$ (5.1 g, 96 mmol) in EtOH/$H_2O$ (5:1,300 ml) was heated at reflux in 2 h, the mixture was cooled filtered the solid, the filtrate was concentrated, taken up in $H_2O$, extracted with DCM (3×), dried over $MgSO_4$, concentrated and purified by ISCO (10% EtOAc/Hexanes) to give the title compound as a yellow solid. MS (m+2): 232.1.

Step 2: 8-Amino-6-bromo-2,2-spirocyclobutyl-2,3-dihydrochromen-4-one

A mixture of 1-(3-amino-5-bromo-2-hydroxyphenyl)ethanone (4.5 g, 20 mmol), cyclobutanone (3 ml, 39 mmol), and pyrrolidine (5 ml, 59 mmol) in p-dioxane (80 ml) was heated at 65° C. for 24 h. The mixture was cooled, taken up in dilute acid, stirred, extracted with EtOAc (3×), dried over $MgSO_4$, concentrated and purified by ISCO (0-20% in 30 min.) to give the title compound as an orange solid. MS (m+2): 284.1.

Step 3: (4R)-8-Amino-6-bromo-2,2-spirocyclobutyl-2,3-dihydrochromen-4-ol

To a stirred solution of (s)-2-methyl-CBS-oxazaborolidine, 1M in toluene (1 ml, 1 mmol) in toluene (2 ml) was added a solution of borane-methyl sulfide complex (5 ml, 11 mmol) in toluene (20 ml) followed by addition of a solution of 8-amino-6-bromo-2,2-spirocyclobutyl-2,3-dihydrochromen-4-one (3 g, 11 mmol) in toluene (40 ml) dropwise. After the reaction was complete as monitored by TLC, it was quenched with 10% aq. HCl (40 ml), stirred for 15 min., extracted with EtOAc (3×), washed with brine, dried over $MgSO_4$, filtered and concentrated to give the title compound as a purple foam. MS (m+1): 285.2.

Step 4: (4R)-8-Amino-6-bromo-4-tertbutyldimethylsilyloxo-2,2-spirocyclobutyl-2,3-dihydrochromene A mixture of 8-amino-6-bromo-2,2-spirocyclobutyl-2,3-dihydrochromen-4-ol (3.2 g, 11 mmol) and imidazole (1 ml, 12 mmol) in DCM (30 ml) was added tert-butylchlorodimethylsilane (2 g, 12 mmol). The mixture was stirred for 3 h, then $H_2O$ was added and the layers were separated, dried over $MgSO_4$, concentrated and the crude was purified by ISCO (5% EtOAc/Hexanes) to give the title compound as a colorless oil. MS (m+1): 399.4.

Step 5: (4R)-8-ethylamino-6-bromo-4-tertbutyldimethylsilyloxo-2,2-spirocyclobutyl-2,3-dihydrochromene A mixture of (4R)-8-amino-6-bromo-4-tertbutyldimethylsilyloxo-2,2-spirocyclobutyl-2,3-dihydrochromene (2 g, 5 mmol), acetaldehyde (0.3 ml, 5 mmol), and trimethyl orthoformate (4 ml, 40 mmol) in DCE (20 ml) was stirred at RT in 30 min. Sodium triacetoxyborohydride (5 g, 25 mmol) was added and stirred in 3 h, quenched with diluted aq. HCl, extracted with DCM (3×), dried over $MgSO_4$, concentrated and purified by ISCO (5% EtOAc/Hexanes) to give the title compound as a light yellow oil. MS (m+1): 428.4.

Step 6: (4R)-6-Bromo-8-(ethylamino)-2,2-spirocyclobutyl-3,4-dihydro-2H-chromen-4-ol A mixture of (4R)-8-ethylamino-6-bromo-4-tertbutyldimethylsilyloxo-2,2-spirocyclobutyl-2,3-dihydrochromene (0.900 g, 2.2 mmol) [and tetrabutylammonium fluoride (2.6 ml, 2.6 mmol)] in THF (15 ml) was added tetrabutylammonium fluoride (2.6 ml, 2.6 mmol). The reaction mixture was stirred at rt in 2 h. $H_2O$ was added and the mixture was extracted with EtOAc (3×), dried over $MgSO_4$, concentrated to give the title compound as a brown oil. MS (m+1): 304.4.

Step 7: (S)-6-Bromo-$N^8$-ethyl-2,2,-spirocyclobutyl-3,4-dihydro-2H-chromene-4,8-diamine The title compound was obtained, as a white foam, by a method analogous to that described in Steps 6-8 of Example 6 above. MS (m+1): 312.2.

Example 20

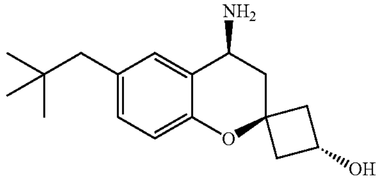

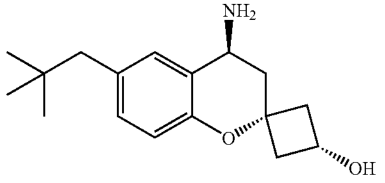

(4S)-[(2,2-Spirocyclobutyl-3'(trans)-hydroxyl)]-6-neopentyl-3,4-dihydro-2H-chromen-4-amine and (4S)-[(2,2-Spirocyclobutyl-3'(cis)-hydroxyl)]-6-neopentyl-3,4-dihydro-2H-chromen-4-amine Step 1: 2,2-Dichloro-3-oxocyclobutyl pivalate To a stirred mixture of vinyl pivalate (30 g, 234 mmol) and zinc (31 g, 468 mmol) in ether (300 ml) was added a solution of 2,2,2-trichloroacetyl chloride (55 g, 304 mmol) in ether (300 ml) dropwise (2-3 h) in a water bath. (Note: fast addition causes the reaction temp. to elevate) while maintaining the reaction temperature between 15-30° C. After the reaction was done (stained with $KMnO_4$ solution), it was filtered through Celite. The filtrate was washed with cold water, brine, dried over $MgSO_4$ and concentrated to give the title compound as an orange solid.

Step 2: 3-Oxocyclobutyl pivalate

To a stirred suspension of zinc dust (103 g, 1568 mmol) in HOAc (200 ml) was added a solution of 2,2-dichloro-3-oxocyclobutyl pivalate (75 g, 314 mmol) in HOAc (400 ml) dropwise in an ice bath. The reaction mixture was stirred for 1 h, filtered the solid through celite and washed with DCM. The DCM layer was washed with $H_2O$, $NaHCO_3$, brine, dried over $MgSO_4$, filtered and concentrated. The crude material was purified by ISCO (10% EtOAc/Hexanes) to give the title compound as a light yellow oil.

Step 3: 3-Hydroxylcyclobutyl pivalate

To a stirred solution of 3-oxocyclobutyl pivalate (15.1 g, 88.7 mmol) in ethanol (100 ml) at 0° C. was added sodium borohydride (4.69 ml, 133 mmol) in several portions. The reaction was stirred for 30 min, slowly quenched with 10% aqueous HCl and concentrated to remove ethanol. The solution was taken up with more 10% HCl, extracted with DCM (3×), washed with brine, dried over $MgSO_4$ and concentrated to give the title compound as a light yellow oil.

Step 4: 3-(tert-Butyldimethylsilyloxy)cyclobutyl pivalate

To a stirred mixture of 3-hydroxycyclobutyl pivalate (16.60 g, 96.4 mmol) and diea (25.2 ml, 145 mmol) in DCM (100 ml) at 0° C. was added tert-butyldimethylsilyl triflate (31.0 ml, 135 mmol) dropwise. The reaction was stirred for 2 h, then quenched with $H_2O$. The layers were separated, and the organic layer was washed with saturated $NaHCO_3$, brine, dried over $MgSO_4$ and concentrated to give the title compound as a light brown oil.

Step 5: 3-(tert-butyldimethylsilyloxy)cyclobutanol

To a stirred solution of 3-(tert-butyldimethylsilyloxy)cyclobutyl pivalate (4.32 g, 15 mmol) in THF (20 ml) at 0° C. was added diisobutylaluminum hydride, 1.0 m solution in hexanes (48 ml, 48 mmol) dropwise. The reaction was stirred in 1 h, then slowly quenched with Rochelle's salt. The quenched mixture was stirred and layers were separated. The organic layer was dried over $MgSO_4$ and concentrated to give the title compound as a colorless oil.

Step 6: 3-(tert-butyldimethylsilyloxy)cyclobutanone

A mixture of 3-(tert-butyldimethylsilyloxy)cyclobutanol (2.59 g, 13 mmol), sodium bicarbonate (3 ml, 38 mmol), and Reactant 1 [?] (7 g, 15 mmol) in DCM (40 ml) was stirred at RT in 4 h, the solid was filtered; the filtrated was purified by ISCO (5% EtOAc/Hexanes) to give the title compound as a colorless oil.

Step 7: (4S)-[(2,2-Spirocyclobutyl-3'(trans)-hydroxyl)]-6-neopentyl-3,4-dihydro-2H-chromen-4-amine and (4S)-[(2,2-Spirocyclobutyl-3' (cis)-hydroxyl)]-6-neopentyl-3,4-dihydro-2H-chromen-4-amine The title compounds were obtained, by a method analogous to that described in Steps 6-8 of Example 6 above, after separation of the cis- and trans-isomers by reverse phase HPLC. MS (m+1): 261.2.

Example 21

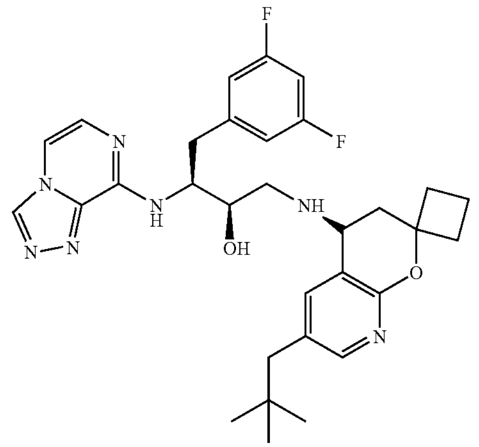

(2R,3,S)-3-([1,2,4]-triazolo[4,3-a]pyrazin-8-ylamino)-4-(3,5-difluorophenyl)-1-OR)-2,2-spirocyclobutane-6-neopentyl-3,4-dihydro-2H-pyrano[2,3-b]pyridine-4-ylamino)butan-2-ol Step 1: 2-Chloropyrimidin-4-amine To a suspension of 2,4-dichloropyrimidine (2.0 g, 13 mmol) in isopropanol (20 mL) was added ammonium hydroxide 28-30% (50 mL, 1385 mmol). The suspension went into solution immediately. The resulting solution was heated at 100° C. in a sealed tube for 18 h. The mixture was brought to RT, extracted with DCM and the combined organics were dried over $MgSO_4$, filtered, and concentrated to afford an off-white solid as 2-chloropyrimidin-4-amine (1.7 g, 57% yield). MS m/z: 130.0 (M+1).

Step 2: 1-(3-Chloropyrazin-2-yl)hydrazine 2,3-Dichloropyrazine (2 mL, 13 mmol) was dissolved in 95% ethanol (4 mL) and to this was added, dropwise and with stiffing, hydrazine anhydrous (2 mL, 67 mmol). During the addition of the hydrazine the solution became warm and yellowish. Following cooling of this mixture in an ice bath, the resulting material was isolated by filtration, washed with cold aqueous 95% ethanol to riled 1-(3-chloropyrazin-2-yl) hydrazine (1.42 g, 73% yield) as white crystals. No further purification was done. MS m/z: 145.0 (M+1).

Step 3: 8-chloro-[1,2,4]triazolo[4,3-a]pyrazine

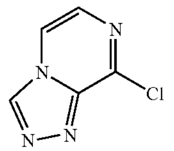

A mixture of 1-(3-chloropyrazin-2-yl)hydrazine (0.90 g, 62 mmol), triethyl orthoformate (2.3 mL), 14 mmol), and dry xylene (15 mL) was refluxed with stirring for 2 h. The mixture was brought to RT, diethyl ether was added and the suspension was filtered. The solid collected was washed with diethyl ether to afford 8-chloro-[1,2,4]triazolo[4,3-a]pyrazine (0.60 g, 62% yield). MS m/z: 155.0 (M+1).

Step 4: (2R,3,S)-3-([1,2,4]-triazolo[4,3-a]pyrazin-8-ylamino)-4-(3,5-difluorophenyl)-1-((R)-2,2-spirocyclobutane-6-neopentyl-3,4-dihydro-2H-pyrano[2,3-b]pyridine-4-ylamino)butan-2-ol A mixture of

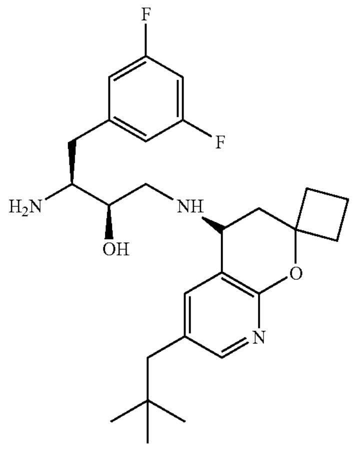

(0.070 g, 0.13 mmol), 8-chloro-[1,2,4]triazolo[4,3-a]pyrazine (0.020 g, 0.13 mmol) and sodium carbonate monohydrate (0.016 g, 0.13 mmol) in ethanol (2 mL) and dimethylformamide (2 mL) was heated at 45° C. for 4 days. The mixture was brought to RT, concentrated, and the residue was dissolved in ethyl acetate. The organic phase was washed with water, brine, dried over $MgSO_4$, filtered, concentrated, and purified by HPLC to afford (2R,3,S)-3-([1,2,4]triazolo[4,3-a]pyrazin-8-ylamino)-4-(3,5-difluorophenyl)-1-((R)-2,2-spirocyclobutane-6-neopentyl-3,4-dihydro-2H-pyrano[2,3-b]pyridine-4-ylamino)butan-2-ol as a light yellow solid. MS m/z: 577.8 (M+1).

Example 22

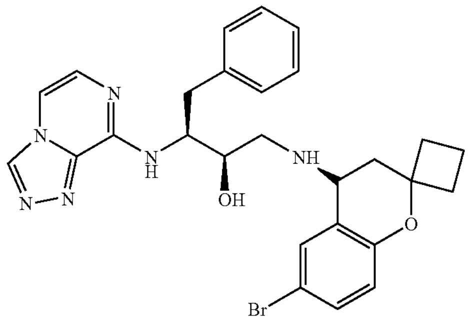

(2R,3S)-3-([1,2,4]-triazolo[4,3-a]pyrazin-8-ylamino)-1-((R)-6-bromo-2,2-spirocyclobutanechroman-4-ylamino)-4-phenylbutan-2-ol To a solution of 8-chloro-[1,2,4]triazolo[4,3-a]pyrazine (0.032 g, 0.21 mmol) and sodium carbonate monohydrate (0.026 g, 0.21 mmol) in ethanol (2 mL) and dimethylformamide was added the chroman-amine

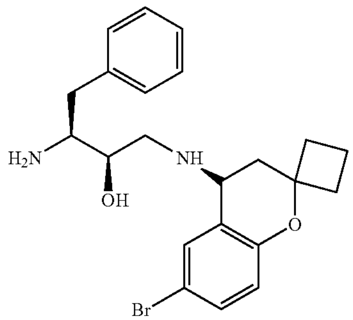

(0.89 g, 0.21 mmol). The resulting mixture was stirred and heated at 60° C. for 17 h. The mixture was concentrated and the residue was dissolved in ethyl acetate, washed with water, brine, dried over $Na_2SO_4$, filtered, concentrated, and purified by HPLC to afford a light yellow solid as 2R,3S)-3-([1,2,4] triazolo[4,3-a]pyrazin-8-ylamino)-1-((R)-6-bromo-2,2-spirocyclobutanechroman-4-ylamino)-4-phenylbutan-2-ol. MS m/z: 551.1 (M+1).

Example 23

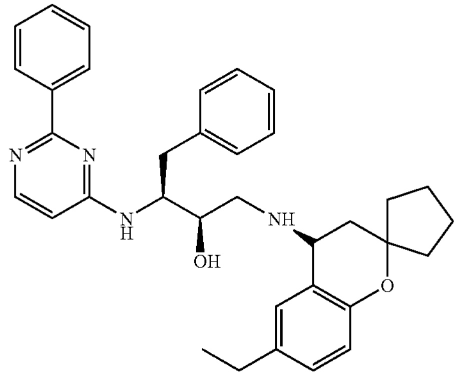

(2R,3S)-1-((R)-6-ethyl-2,2-spirocyclopentanechroman-4-ylamino)-4-phenyl-3-(2-phenylpyrimidin-4-ylamino)butan-2-ol Step 1: (2R,3S)-3-(2-chloropyrimidine-4-ylamino)-1-((R)-6-ethyl-2,2-spirocyclopentanechroman-4-ylamino)-4-phenylbutan-2-ol A solution of 2,4-dichloropyrimidine (0.050 g, 0.34 mmol), ethylchroman-amine

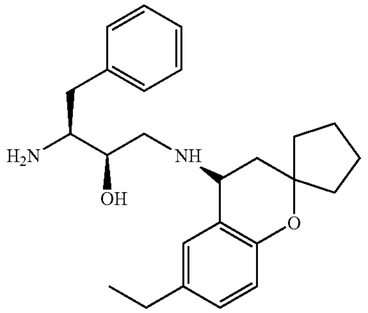

(0.13 g, 0.34 mmol), and sodium carbonate monohydrate (0.036 mg, 0.34 mmol) in isopropanol (3 mL) and dimethylformamide (3 mL) was heated in a sealed tube for 17 h. The mixture was brought to room temperature, concentrated and the residue was dissolved in ethyl acetate, washed with water, brine, dried over $Na_2SO_4$, filtered, and concentrated to afford (2R,3S)-3-(2-chloropyrimidine-4-ylamino)-1-((R)-6-ethyl-2,2-spirocyclopentanechroman-4-ylamino)-4-phenylbutan-2-ol (0.13 g, 76% yield). MS m/z: 507.2 (M+1).

Step 2: (2R,3S)-1-((R)-6-ethyl-2,2-spirocyclopentanechroman-4-ylamino)-4-phenyl-3-(2-phenylpyrimidin-4-ylamino)butan-2-ol A mixture of phenylboronic acid (0.063 g, 0.52 mmol), (2R,3S)-3-(2-chloropyrimidine-4-ylamino)-1-((R)-6-ethyl-2,2-spirocyclopentanechroman-4-ylamino)-4-phenylbutan-2-ol (0.13 g, 0.26 mmol), $PdCl_2(dppf)_2$ (0.021 g, 0.026 mmol), and sodium carbonate monohydrate (0.097 g, 0.78 mmol) in dimethylformamide was heated to reflux for 3 h and brought to room temperature. The mixture was filtered through celite, concentrated, and purified by HPLC to afford a white solid as (2R,3S)-1-((R)-6-ethyl-2,2-spirocyclopentanechroman-4-ylamino)-4-phenyl-3-(2-phenylpyrimidin-4-ylamino)butan-2-01 MS m/z: 549.4 (M+1).

The following examples in Table I were prepared by Methods A (Scheme 7), B (Scheme 8) or C (Scheme 9) and/or steps analogous to those described in Examples 6, 9, 11 and 21-23 above.

TABLE 1

| Ex. No. | Compound Name | Mass found $(M + H)^+$ | Enzyme Data $IC_{50}$ (uM) | Cell Data $IC_{50}$ (uM) | Method of making |
|---|---|---|---|---|---|
| 24 | (2R,3S)-3-((2-chloro-4-pyrimidinyl)amino)-4-(3,5-difluorophenyl)-1-(((4'S)-6'-(2,2-dimethylpropyl)-3',4'-dihydrospiro[cyclobutane-1,2'-pyrano[2,3-b]pyridin]-4'-yl)amino)-2-butanol | 572.1 | +++++ | ++++ | B |
| 21 | (2R,3S)-4-(3,5-difluorophenyl)-1-(((4'S)-6'-(2,2-dimethylpropyl)-3',4'-dihydrospiro[cyclobutane-1,2'-pyrano[2,3-b]pyridin]-4'-yl)amino)-3-([1,2,4]triazolo[4,3-a]pyrazin-8-ylamino)-2-butanol | 577.8 | ++++ | +++++ | A |
| 25 | (2R,3S)-4-(3,5-difluorophenyl)-1-(((4'S)-6'-(2,2-dimethylpropyl)-3',4'-dihydrospiro[cyclobutane-1,2'-pyrano[2,3-b]pyridin]-4'-yl)amino)-3-(2-pyrimidinylamino)-2-butanol | 538.2 | ++++ | +++ | B |
| 26 | (2R,3S)-4-(3,5-difluorophenyl)-1-(((4'S)-6'-(2,2-dimethylpropyl)-3',4'-dihydrospiro[cyclobutane-1,2'-pyrano[2,3-b]pyridin]-4'-yl)amino)-3-((2-fluorophenyl)amino)-2-butanol | 554.2 | +++ | + | B |
| 27 | 3-((2S,3R)-4-(((4S)-6-ethyl-3,4-dihydrospiro[chromene-2,1'-cyclobutan]-4-yl)amino)-2-((2-fluorophenyl)amino)-3-hydroxybutyl)benzonitrile | 500.1 | +++ | ++++ | B |
| 28 | (2R,3S)-3-((6-chloro-4-pyrimidinyl)amino)-1-(((4'S)-6'-(2,2-dimethylpropyl)-3',4'-dihydrospiro[cyclobutane-1,2'-pyrano[2,3-b]pyridin]-4'-yl)amino)-4-(4-fluorophenyl)-2-butanol | 554.2 | +++ | + | A |
| 29 | (2R,3S)-3-((2-chloro-4-pyrimidinyl)amino)-1-(((4'S)-6'-(2,2-dimethylpropyl)-3',4'-dihydrospiro[cyclobutane-1,2'-pyrano[2,3-b]pyridin]-4'-yl)amino)-4-(4-fluorophenyl)-2-butanol | 554.2 | +++ | + | A |

TABLE 1-continued

| Ex. No. | Compound Name | Mass found $(M + H)^+$ | Enzyme Data $IC_{50}$ (uM) | Cell Data $IC_{50}$ (uM) | Method of making |
|---|---|---|---|---|---|
| 30 | (2R,3S)-1-(((4'S)-6'-(2,2-dimethylpropyl)-3',4'-dihydrospiro[cyclobutane-1,2'-pyrano[2,3-b]pyridin]-4'-yl)amino)-4-(4-fluorophenyl)-3-(thieno[3,2-d]pyrimidin-4-ylamino)-2-butanol | 576.2 | ++ | + | A |
| 31 | (2R,3S)-1-(((4S)-6-ethyl-3,4-dihydrospiro[chromene-2,1'-cyclobutan]-4-yl)amino)-3-((2-fluorophenyl)amino)-4-phenyl-2-butanol | 475.3 | ++ | + | B |
| 32 | (2R,3S)-1-(((4S)-6-ethyl-3,4-dihydrospiro[chromene-2,1'-cyclopentan]-4-yl)amino)-3-((2-fluorophenyl)amino)-4-phenyl-2-butanol | 489.2 | ++ | + | B |
| 33 | (2R,3S)-1-((S)-6-ethyl-2,2-spirocyclobutyl-chroman-4-ylamino)-4-phenyl-3-(4-(trifluoromethyl)pyrimidin-2-ylamino)butan-2-ol | 527.2 | + | + | A |
| 34 | (2R,3S)-3-((6-chloro-2-(methylthio)-4-pyrimidinyl)amino)-1-(((4'S)-6'-(2,2-dimethylpropyl)-3',4'-dihydrospiro[cyclobutane-1,2'-pyrano[2,3-b]pyridin]-4'-yl)amino)-4-(4-fluorophenyl)-2-butanol | 600.1 | ++ | + | A |
| 35 | (2R,3S)-1-(((4'S)-6'-(2,2-dimethylpropyl)-3',4'-dihydrospiro[cyclobutane-1,2'-pyrano[2,3-b]pyridin]-4'-yl)amino)-4-(4-fluorophenyl)-3-(thieno[2,3-d]pyrimidin-4-ylamino)-2-butanol | 576.2 | + | ++++ | A |
| 22 | (2R,3S)-1-(((4S)-6-bromo-3,4-dihydrospiro[chromene-2,1'-cyclobutan]-4-yl)amino)-4-phenyl-3-([1,2,4]triazolo[4,3-a]pyrazin-8-ylamino)-2-butanol | 551.1 | + | ++ | B |
| 36 | (2R,3S)-3-(1,3-benzoxazol-2-ylamino)-1-(((4S)-6-ethyl-3,4-dihydrospiro[chromene-2,1'-cyclobutan]-4-yl)amino)-4-phenyl-2-butanol | 498.2 | + | +++ | A |
| 37 | (2R,3S)-1-((S)-6-ethyl-2,2-spirocyclobutyl-chroman-4-ylamino)-4-phenyl-3-(4-ethyl pyrimidin-2-ylamino)butan-2-ol | 487.5 | + | ++ | A |
| 38 | (2R,3S)-1-((S)-6-ethyl-2,2-spirocyclobutyl-chroman-4-ylamino)-4-phenyl-3-(pyrimidin-2-ylamino)butan-2-ol | 459.2 | + | + | A |
| 39 | (2R,3S)-3-((6-chloro-3-pyridazinyl)amino)-1-(((4S)-6-ethyl-3,4-dihydrospiro[chromene-2,1'-cyclobutan]-4-yl)amino)-4-phenyl-2-butanol | 493.3 | + | + | A |
| 40 | (2R,3S)-1-(((4S)-6-ethyl-3,4-dihydrospiro[chromene-2,1'-cyclopentan]-4-yl)amino)-4-phenyl-3-(2-pyrazinylamino)-2-butanol | 473.4 | | + | C |
| 41 | (2S,3S)-1-(((4'S)-6'-(2,2-dimethylpropyl)-3',4'-dihydrospiro[cyclobutane-1,2'-pyrano[2,3-b]pyridin]-4'-yl)amino)-3-((2-fluorophenyl)amino)-4-phenyl-2-butanol | 518.3 | + | + | B |
| 42 | (2R,3S)-3-(1,3-benzothiazol-2-ylamino)-1-(((4S)-6-ethyl-3,4-dihydrospiro[chromene-2,1'-cyclobutan]-4-yl)amino)-4-phenyl-2-butanol | 514.3 | + | | A |
| 43 | (2R,3S)-1-(((4S)-6-ethyl-3,4-dihydrospiro[chromene-2,1'-cyclobutan]-4-yl)amino)-4-phenyl-3-(3-pyridinylamino)-2-butanol | 458.4 | + | + | B |

TABLE 1-continued

| Ex. No. | Compound Name | Mass found $(M + H)^+$ | Enzyme Data $IC_{50}$ (uM) | Cell Data $IC_{50}$ (uM) | Method of making |
|---|---|---|---|---|---|
| 44 | (2R,3S)-1-(((4S)-6-ethyl-3,4-dihydrospiro[chromene-2,1'-cyclobutan]-4-yl)amino)-4-phenyl-3-(4-pyridinylamino)-2-butanol | 458.4 | | +++ | B |
| 45 | 3-(((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((3-fluorophenyl)methyl)-2-hydroxypropyl)amino)-4-(ethyloxy)-3-cyclobutene-1,2-dione | 566.0 | +++++ | ++++ | |

The following key will help to appreciate the data provided in Table I:

+designates an $IC_{so}$ value in the range from 10 uM-25 uM;

++designates an $IC_{so}$ value in the range from 5 uM-10 uM;

+++designates an $IC_{so}$ value in the range from 1.0 uM-5 uM;

++++designates an $IC_{so}$ value in the range from 100 nM-1.0 uM; and

+++++designates an $IC_{so}$ value of below 100 nM

The following examples provide a further understanding and appreciation of compounds of the present invention.

The present invention also provides methods for making compounds of Formulas I-II. In another embodiment of the invention, there is provided a method of making a compound of Formula I or II, the method comprising the step of reacting a compound 30

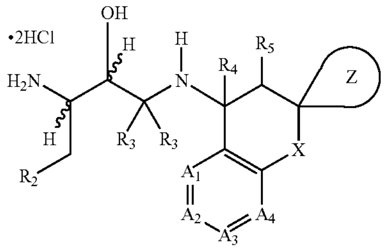

30 wherein $A^1$, $A^2$, $A^3$, $A^4$, $R^2$, $R^3$, $R^4$, $R^5$, X and ring Z are as defined herein, with a compound having the structure $R^1$-halo, wherein $R^1$ is as defined herein and "halo" is a halogen group, generally a chlorine, bromine or iodine, to make a compound of Formulas I or II.

As can be appreciated by the skilled artisan, the above synthetic schemes and representative examples are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds.

For example, in these procedures, the steps may be preceded, or followed, by additional protection/deprotection steps as necessary. Particularly, if one or more functional groups, for example carboxy, hydroxy, amino, or mercapto groups, are or need to be protected in preparing the compounds of the invention, because they are not intended to take part in a specific reaction or chemical transformation, various known conventional protecting groups may be used. For example, protecting groups typically utilized in the synthesis of natural and synthetic compounds, including peptides, nucleic acids, derivatives thereof and sugars, having multiple reactive centers, chiral centers and other sites potentially susceptible to the reaction reagents and/or conditions, may be used.

The protecting groups may already be present in precursors and should protect the functional groups concerned against unwanted secondary reactions, such as acylations, etherifications, esterifications, oxidations, solvolysis, and similar reactions. It is a characteristic of protecting groups that they readily lend themselves, i.e. without undesired secondary reactions, to removal, typically accomplished by solvolysis, reduction, photolysis or other methods of removal such as by enzyme activity, under conditions analogous to physiological conditions. It should also be appreciated that the protecting groups should not be present in the end-products. The specialist knows, or can easily establish, which protecting groups are suitable with the reactions described herein. Synthetic chemistry transformations and protecting group methodologies (protection and deprotection) useful in synthesizing the inhibitor compounds described herein are known in the art and include, for example, those such as described in R. Larock, Comprehensive Organic Transformations, VCH Publishers (1989); T. W. Greene and P. G. M. Wuts, *Protective Groups in Organic Synthesis,* $3^{rd}$ edition, John Wiley and Sons (1999); L. Fieser and M. Fieser, Fieser and Fieser's Reagents for Organic Synthesis, John Wiley and Sons (1994); A. Katritzky and A. Pozharski, Handbook of Heterocyclic Chemistry, $2^{nd}$ edition (2001); M. Bodanszky, A. Bodanszky, The Practice of Peptide Synthesis, Springer-Verlag, Berlin Heidelberg (1984); J. Seyden-Penne, Reductions by the Alumino- and Borohydrides in Organic Synthesis, $2^{nd}$ edition, Wiley-VCH, (1997); and L. Paquette, editor, Encyclopedia of Reagents for Organic Synthesis, John Wiley and Sons (1995).

Salts, including pharmaceutically acceptable salts, of a compound of the invention having a salt-forming group may be prepared in a conventional manner or manner known to persons skilled in the art. For example, acid addition salts of compounds of the invention may be obtained by treatment with an acid or with a suitable anion exchange reagent. A salt with two acid molecules (for example a dihalogenide) may also be converted into a salt with one acid molecule per compound (for example a monohalogenide); this may be done by heating to a melt, or for example by heating as a solid under a high vacuum at elevated temperature, for example from 50° C. to 170° C., one molecule of the acid being expelled per molecule of the compound.

Acid salts can usually be converted to free-base compounds, e.g. by treating the salt with suitable basic agents, for example with alkali metal carbonates, alkali metal hydrogen carbonates, or alkali metal hydroxides, typically potassium carbonate or sodium hydroxide. Exemplary salt forms and their preparation are described herein in the Definition section of the application.

All synthetic procedures described herein can be carried out under known reaction conditions, advantageously under those described herein, either in the absence or in the presence (usually) of solvents or diluents. As appreciated by those of ordinary skill in the art, the solvents should be inert with respect to, and should be able to dissolve, the starting materials and other reagents used. Solvents should be able to partially or wholly solubilize the reactants in the absence or presence of catalysts, condensing agents or neutralizing agents, for example ion exchangers, typically cation exchangers for example in the $H^+$ form. The ability of the solvent to allow and/or influence the progress or rate of the reaction is generally dependant on the type and properties of the solvent(s), the reaction conditions including temperature, pressure, atmospheric conditions such as in an inert atmosphere under argon or nitrogen, and concentration, and of the reactants themselves.

Suitable solvents for conducting reactions to synthesize compounds of the invention include, without limitation, water; esters, including lower alkyl-lower alkanoates, e.g., EtOAc; ethers including aliphatic ethers, e.g., $Et_2O$ and ethylene glycol dimethylether or cyclic ethers, e.g., THF; liquid aromatic hydrocarbons, including benzene, toluene and xylene; alcohols, including MeOH, EtOH, 1-propanol, IPOH, n- and t-butanol; nitriles including $CH_3CN$; halogenated hydrocarbons, including $CH_2Cl_2$, $CHCl_3$ and $CCl_4$; acid amides including DMF; sulfoxides, including DMSO; bases, including heterocyclic nitrogen bases, e.g. pyridine; carboxylic acids, including lower alkanecarboxylic acids, e.g., AcOH; inorganic acids including HCl, HBr, HF, $H_2SO_4$ and the like; carboxylic acid anhydrides, including lower alkane acid anhydrides, e.g., acetic anhydride; cyclic, linear, or branched hydrocarbons, including cyclohexane, hexane, pentane, isopentane and the like, and mixtures of these solvents, such as purely organic solvent combinations, or water-containing solvent combinations e.g., aqueous solutions. These solvents and solvent mixtures may also be used in "working-up" the reaction as well as in processing the reaction and/or isolating the reaction product(s), such as in chromatography.

Purification methods are known in the art and include, for example, crystallization, chromatography (liquid and gas phase, and the like), extraction, distillation, trituration, reverse phase HPLC and the like. Reactions conditions such as temperature, duration, pressure, and atmosphere (inert gas, ambient) are known in the art and may be adjusted as appropriate for the reaction.

The invention further encompasses "intermediate" compounds, including structures produced from the synthetic procedures described, whether isolated or generated in-situ and not isolated, prior to obtaining the finally desired compound. Structures resulting from carrying out steps from a transient starting material, structures resulting from divergence from the described method(s) at any stage, and structures forming starting materials under the reaction conditions are all "intermediates" included in the invention. Further, structures produced by using starting materials in the form of a reactive derivative or salt, or produced by a compound obtainable by means of the process according to the invention and structures resulting from processing the compounds of the invention in situ are also within the scope of the invention.

New starting materials and/or intermediates, as well as processes for the preparation thereof, are likewise the subject of this invention. In select embodiments, such starting materials are used and reaction conditions so selected as to obtain the desired compound(s).

Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups may be protected with suitable protecting groups when necessary. Protecting groups, their introduction and removal are described above.

Compounds of the present invention can possess, in general, one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt. All such isomeric forms of such compounds are expressly included in the present invention.

The compounds of this invention may also be represented in multiple tautomeric forms. The compounds may also occur in cis- or trans- or E- or Z-double bond isomeric forms. The invention expressly includes all tautomeric forms of the compounds described herein.

All crystal forms of the compounds described herein are expressly included in the present invention.

Substituents on ring moieties (e.g., phenyl, thienyl, etc.) may be attached to specific atoms, whereby they are intended to be fixed to that atom, or they may be drawn unattached to a specific atom, whereby they are intended to be attached at any available atom that is not already substituted by an atom other than H (hydrogen). For example, the $R^{12}$ substituent is drawn unattached to any specific atom of ring $Z^2$, and therefore each of the n number of $R^{12}$ substituents may be attached to any atom of $Z^2$.

The present invention also includes isotopically-labelled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{16}O$, $^{17}O$, $^{31}P$, $^{32}P$, $^{35}S$, $^{18}F$, and $^{36}Cl$.

Compounds of the present invention that contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detection. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of this invention can generally be prepared by substituting a readily available isotopically labelled reagent for a non-isotopically labelled reagent.

Biological Evaluation

The compounds of the invention may be modified by appending appropriate functionalities to enhance selective biological properties. Such modifications may increase biological penetration into a given biological compartment (e.g., blood, lymphatic system, central nervous system), increase oral availability, increase solubility to allow administration by injection, alter metabolism and alter rate of excretion. By way of example, a compound of the invention may be modified to incorporate a hydrophobic group or "greasy" moiety in an attempt to enhance the passage of the compound through a hydrophobic membrane, such as a cell wall.

Although the pharmacological properties of the compounds of the invention (Formulas I and II) vary with structural change, in general, activity possessed by compounds of Formulas I and II may be demonstrated both in vitro as well as in vivo. Particularly, the pharmacological properties of the compounds of this invention may be confirmed by a number of pharmacological in vitro assays.

The following biological assays were used to characterize the ability of compounds of the invention to regulate the cleavage of amyloid beta precursor protein, thereby reducing or inhibiting the production of amyloid beta. Compounds of the invention were found to modulate BACE activity.

In Vitro Enzymatic BACE FRET (Fluorescence Resonance Energy Transfer) Assay (Enzyme Assay)

Assay buffer is 0.05 M acetate, pH 4.2, 10% DMSO final, 100 uM genapol (which is a nonionic detergent, below it's Critical Micelle Concentration). Enzyme (0.2 nM) is pre-incubated for one hour with inhibitors added in 1 uL of DMSO. Then the assay is started by the addition of FRET substrate (50 nM) and incubated for one hour. The FRET assay is terminated with by addition of Tris buffer, which raises the pH to neutrality, and the fluorescence is determined The FRET substrate is a peptide with commercially available fluorophore and quencher, on opposite sides of the BACE cleavage site. Proteolytic cleavage of the FRET substrate releases quenching of fluorescence (excitation 488 nm and emission 425 nm). Data in the in-vitro BACE FRET enzyme assay for those Examples tested is provided in Table 1.

BACE Cell-Based Assay (Cell Assay)

The cell-based assay measures inhibition or reduction of Aβ40 in conditioned medium of test compound treated cells expressing amyloid precursor protein.

Cells stably expressing Amyloid Precursor Protein (APP) were plated at a density of 40K cells/well in 96 well plates (Costar). The cells were cultivated for 24 hours at 37° C. and 5% $CO_2$ in DMEM supplemented with 10% FBS. The test compounds were then added to cells in 10-point dose response concentrations with the starting concentration being either 100 μM or 10 μM. The compounds were diluted from stock solutions in DMSO and the final DMSO concentration of the test compounds on cells was 0.1%. After 24 h of incubation with the test compounds the supernatant conditioned media was collected and the Aβ40 levels were determined using a sandwich ELISA. The $IC_{50}$ of the compound was calculated from the percent of control or percent inhibition of Aβ40 as a function of the concentration of the test compound.

The sandwich ELISA to detect Aβ40 was performed in 96 well microtiter plates, which were pre-treated with goat anti-rabbit IgG (Pierce). The capture and detecting antibody pair that were used to detect Aβ40 from cell supernatants were affinity purified pAb40 (Biosource) and biotinylated 6E10 (Signet Labs Inc.), respectively. The optimal concentration for the pAb40 antibody was 3 μg/ml in Superblock/TBS (Pierce) that was supplemented with 0.05% Tween 20 (Sigma). Optimal concentration for the detection antibody 6E10-biotinylated was 0.5 μg/ml in Superblock/TBS (Pierce) that had been supplemented with 2% normal goat serum and 2% normal mouse serum.

Cellular supernatants were incubated with the capture antibody for 3 h at 4° C., followed by 3 wash steps in TBS-tween (0.05%). The detecting antibody incubation was for 2 h at 4° C., again followed by the wash steps as described previously. The final readout of the ELISA is Time-Resolved Fluorescence (counts per minute) using Delfia reagents Streptavidin-Europium and Enhancement solutions (Perkin Elmer) and the Victor 2 multilabel counter (Perkin Elmer).

Data in the in-vitro BACE cell enzyme assay for those Examples tested is provided in Table 1.

Indications

Accordingly, compounds of the invention are useful for, but not limited to, the prevention or treatment of beta-secretase related diseases, including Alzheimer's disease. The compounds of the invention have the ability to modulate the formation of amyloid beta, and reduce the formation and deposition of plaque on the brain. In one embodiment of the invention, there is provided a method of treating a disorder related to a beta-secretase enzyme in a subject, the method comprising administering to the subject an effective dosage amount of a compound of Formulas I or II. In another embodiment, there is provided a method of reducing production of amyloid beta, and of reducing plaque formation. In yet another embodiment, the invention provides a method of treating Alzheimer's disease.

Accordingly, the compounds of the invention would be useful in therapy as CNS agents in treating neurological disorders and related conditions.

Besides being useful for human treatment, these compounds are useful for veterinary treatment of companion animals, exotic animals and farm animals, including mammals, rodents, and the like. For example, animals including horses, dogs, and cats may be treated with compounds provided by the invention.

Formulations and Method of Use

Treatment of diseases and disorders herein is intended to also include therapeutic administration of a compound of the invention, or a pharmaceutical salt thereof, or a pharmaceutical composition of either to a subject (i.e., an animal, preferably a mammal, most preferably a human) which may be in need of preventative treatment, such as, for example, for pain, inflammation and the like. Treatment also encompasses prophylactic administration of a compound of the invention, or a pharmaceutical salt thereof, or a pharmaceutical composition of either to a subject (i.e., an animal, preferably a mammal, most preferably a human). Generally, the subject is initially diagnosed by a licensed physician and/or authorized medical practitioner, and a regimen for prophylactic and/or therapeutic treatment via administration of the compound(s) or compositions of the invention is suggested, recommended or prescribed.

The amount of compound(s) which is/are administered and the dosage regimen for treating neurological disorders and beta-secretase mediated diseases with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, advantageously between about 0.01 and about 50 mg/kg, more advantageously about 0.01 and about 30 mg/kg, and even more advantageously between about 0.1 and about 10 mg/kg body weight may be appropriate, and should be useful for all methods of use disclosed herein. The daily dose can be administered in one to four doses per day.

While it may be possible to administer a compound of the invention alone, in the methods described, the compound administered normally will be present as an active ingredient in a pharmaceutical composition. Thus, in another embodiment of the invention, there is provided a pharmaceutical composition comprising a compound of this invention in combination with a pharmaceutically acceptable carrier, which includes diluents, excipients, adjuvants and the like (collectively referred to herein as "carrier" materials) as described herein, and, if desired, other active ingredients. A pharmaceutical composition of the invention may comprise an effective amount of a compound of the invention or an effective dosage amount of a compound of the invention. An effective dosage amount of a compound of the invention includes an amount less than, equal to or greater than an effective amount of the compound. For example, a pharmaceutical composition in which two or more unit dosages, such as in tablets, capsules and the like, are required to administer an effective amount of the compound, or alternatively, a multi-dose pharmaceutical composition, such as powders, liquids and the like, in which an effective amount of the compound is administered by administering a portion of the composition. Alternatively, a pharmaceutical composition in which two or more unit dosages, such as in tablets, capsules and the like, are required to administer an effective amount of the compound may be administered in less than an effective amount for one or more periods of time, for example to ascertain the effective dose for an individual subject, to desensitize an individual subject to potential side effects, to permit effective dosing readjustment or depletion of one or more other therapeutics administered to an individual subject, and/or the like.

The compound(s) of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, advantageously from about 1 to 500 mg, and typically from about 5 to 150 mg. A suitable daily dose for a human or other mammal may vary widely depending on the condition of the patient and other factors, but, once again, can be determined using routine methods and practices.

For therapeutic purposes, the active compounds of this invention are ordinarily combined with one or more adjuvants or "excipients" appropriate to the indicated route of administration. If orally administered on a per dose basis, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, to form the final formulation. For example, the active compound(s) and excipient(s) may be tableted or encapsulated by known and accepted methods for convenient administration. Examples of suitable formulations include, without limitation, pills, tablets, soft and hard-shell gel capsules, troches, orally-dissolvable forms and delayed or controlled-release formulations thereof. Particularly, capsule or tablet formulations may contain one or more controlled-release agents, such as hydroxypropylmethyl cellulose, as a dispersion with the active compound(s).

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

The active ingredient may also be administered by injection as a composition with suitable carriers including saline, dextrose, or water. The daily parenteral dosage regimen will be from about 0.1 to about 30 mg/kg of total body weight, and preferably from about 0.1 to about 10 mg/kg.

For pulmonary administration, the pharmaceutical composition may be administered in the form of an aerosol or with an inhaler including dry powder aerosol.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

Accordingly, in yet another embodiment of the present invention, there is provided a method of manufacturing a medicament, the method comprising combining an amount of a compound according to Formulas I or II with a pharmaceutically acceptable carrier to manufacture the medicament.

In yet another embodiment, the invention provides a method of manufacturing a medicament for the treatment of Alzheimer's disease, the method comprising combining an amount of a compound according to Formulas I or II with a pharmaceutically acceptable carrier to manufacture the medicament.

Combinations

While the compounds of the invention can be dosed or administered as the sole active pharmaceutical agent, they can also be used in combination with one or more compounds of the invention or in conjunction with other agents. When administered as a combination, the therapeutic agents can be formulated as separate compositions that are administered simultaneously or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of beta-secretase, gamma-secretase and/or other reagents known in influence the formation and/or deposition of amyloid beta, otherwise responsible for the formation of plaque on the brain.

If formulated as a fixed dose, such combination products employ the compounds of this invention within the accepted dosage ranges. Compounds of Formulas I and II may also be administered sequentially with known anti-inflammatory agents when a combination formulation is inappropriate. The invention is not limited in the sequence of administration; compounds of the invention may be administered either prior to, simultaneous with or after administration of the known anti-inflammatory agent.

The foregoing description is merely illustrative of the invention and is not intended to limit the invention to the disclosed compounds, compositions and methods. Variations and changes, which are obvious to one skilled in the art, are intended to be within the scope and nature of the invention, as defined in the appended claims. From the foregoing description, one skilled in the art can easily ascertain the essential characteristics of this invention, and without departing from the spirit and scope thereof, can make various changes and modifications of the invention to adapt it to various usages and conditions. All patents and other publications recited herein are hereby incorporated by reference in their entireties.

What is claimed is:

1. A compound of Formula I:

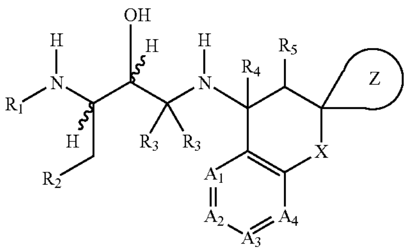

I or a stereoisomer or pharmaceutically acceptable salt thereof, wherein $R^1$ is a partially or fully unsaturated 4-8 membered monocyclic or 6-12 membered bicyclic ring, said ring formed of carbon atoms optionally including 1-3 heteroatoms if monocyclic or 1-6 heteroatoms if bicyclic, said heteroatoms selected from O, N, or S, and wherein said ring is optionally substituted independently with one or more substituents of oxo, $R^7$, $NR^7R^7$, $OR^7$, $SR^7$, $C(O)R^7$, $OC(O)R^7$, $COOR^7$, $C(O)NR^7R^7$, $NR^7C(O)R^7$, $NR^7C(O)NR^7R^7$, $NR^7(COOR^7)$, $OC(O)NR^7R^7$, $S(O)_2NR^7R^7$, $NR^7S(O)_2NR^7R^7$ or $NR^7S(O)_2R^7$;

$R^2$ is a partially or fully saturated or fully unsaturated 3-8 membered monocyclic or 6-12 membered bicyclic ring, said ring formed of carbon atoms optionally including 1-3 heteroatoms if monocyclic or 1-6 heteroatoms if bicyclic, said heteroatoms selected from O, N, or S, and wherein said ring is optionally substituted independently with one or more substituents of oxo, $R^7$, $NR^7R^7$, $OR^7$, $SR^7$, $C(O)R^7$, $OC(O)R^7$, $COOR^7$, $C(O)NR^7R^7$, $NR^7C(O)R^7$, $NR^7C(O)NR^7R^7$, $NR^7(COOR^7)$, $OC(O)NR^7R^7$, $S(O)_2NR^7R^7$, $NR^7S(O)_2NR^7R^7$ or $NR^7S(O)_2R^7$;

each $R^3$, independently, is H, haloalkyl, CN, $C_{1-6}$-alkyl, $C_{2-8}$-alkenyl, $C_{2-8}$-alkynyl, $C_{3-8}$-cycloalkyl or $C_{4-8}$-cycloalkenyl, each of the $C_{1-6}$-alkyl, $C_{2-8}$-alkenyl, $C_{2-8}$-alkynyl, $C_{3-8}$-cycloalkyl and $C_{4-8}$-cycloalkenyl optionally comprising 1-2 heteroatoms selected from N, O and S and optionally substituted with 1-5 substituents of $R^7$;

$R^4$ is H, halo or $C_{1-6}$-alkyl;

$R^5$ is H, halo, haloalkyl, oxo, $C_{1-6}$-alkyl, —O—$C_{1-6}$-alkyl, —S—$C_{1-6}$-alkyl, —NH—$C_{1-6}$alkyl, —N-di-$C_{1-6}$-alkyl, CN, OH or $NH_2$, wherein the $C_{1-6}$-alkyl and the $C_{1-6}$-alkyl portion of —O—$C_{1-6}$-alkyl, —S—$C_{1-6}$-alkyl, —NH—$C_{1-6}$-alkyl and —N-di-$C_{1-6}$-alkyl are optionally substituted independently with 1-5 substituents of $R^7$;

each of $A^1$, $A^2$, $A^3$ and $A^4$, independently, is $CR^6$;

X is O;

Z is a 3-6 membered spirocyclic ring formed of carbon atoms optionally including 1-3 heteroatoms selected from O, N and S and optionally substituted independently with 1-3 substituents of $R^7$;

each $R^6$, independently, is halo, haloalkyl, $C_{1-6}$-alkyl, —O—$C_{1-6}$-alkyl, —S—$C_{1-6}$-alkyl, —NH—$C_{1-6}$-alkyl, —N-di-$C_{1-6}$-alkyl, CN, OH, $NH_2$, $C_{2-6}$-alkenyl, $C_{2-6}$-alkynyl, $C_{3-8}$-cycloalkyl or $C_{4-8}$-cycloalkenyl, wherein the $C_{1-6}$-alkyl, $C_{2-6}$-alkenyl, $C_{2-6}$-alkynyl, $C_{3-8}$-cycloalkyl, $C_{4-8}$-cycloalkenyl and the $C_{1-6}$-alkyl portion of —O—$C_{1-6}$-alkyl, —S—$C_{1-6}$-alkyl, —NH—$C_{1-6}$-alkyl and —N-di-$C_{1-6}$-alkyl are optionally substituted with 1-5 substituents of $R^7$;

or $R^6$ is a fully unsaturated or partially or fully unsaturated 5- or 6-membered monocyclic or bicyclic ring formed of carbon atoms, said ring optionally including 1-5 heteroatoms selected from O, N, or S and optionally substituted with one or more substituents of $R^7$; and each $R^7$, independently, is H, halo, haloalkyl, CN, OH, $NO_2$, $NH_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxy, $C_{1-10}$-thioalkoxy or a fully saturated or partially or fully unsaturated 3-8 membered monocyclic or a 6-12 membered bicyclic ring, said ring formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxy, $C_{1-10}$-thioalkoxy and ring is optionally substituted independently with 1-5 substituents of halo, haloalkyl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxy, isobutoxy, tert-butoxy, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxy, benzyl or phenyl.

2. The compound of claim 1 wherein $R^1$ is an optionally substituted ring selected from phenyl, naphthyl, pyridyl, pyrimidyl, pyridazinyl, pyrazinyl, triazinyl, quinolinyl, isoquinolinyl, quinazolinyl, isoquinazolinyl, phthalazinyl, thiophenyl, thienopyrimidinyl, thienopyridinyl, furyl, pyrrolyl, pyrazolyl, pyrazolopyridinyl, pyrazoliopyrimidinyl, imidazolyl, triazolyl, triazolopyrazinyl, triazolopyridinyl, tetrazolyl, thiazolyl, oxazolyl, isoxazolyl, isothiazolyl, thiadiazolyl, oxadiazolyl, indolyl, isoindolyl, benzofuranyl, benzothiophenyl, benzimidazolyl, benzoxazolyl, benzisoxazolyl, benzothiazolyl, benzoisothiazolyl, benzotriazolyl, tetrahydrofuranyl, pyrrolidinyl, oxazolinyl, isoxazolinyl, thiazolinyl, pyrazolinyl and benzodioxolyl.

3. The compound of claim 2 wherein $R^2$ is an optionally substituted ring selected from phenyl, naphthyl, pyridyl, pyrimidyl, pyridazinyl, pyrazinyl, triazinyl, quinolinyl, isoquinolinyl, quinazolinyl, isoquinazolinyl, phthalazinyl, thiophenyl, furyl, pyrrolyl, pyrazolyl, imidazolyl, triazolyl, tetrazolyl, thiazolyl, oxazolyl, isoxazolyl, isothiazolyl, thiadiazolyl, oxadiazolyl, indolyl, isoindolyl, benzofuranyl, benzothiophenyl, benzimidazolyl, benzoxazolyl, benzisoxazolyl, benzothiazolyl, benzoisothiazolyl, benzotriazolyl, tetrahydrofuranyl, pyrrolidinyl, oxazolinyl, isoxazolinyl, thiazolinyl, pyrazolinyl, morpholinyl, piperidinyl, piperazinyl, pyranyl, benzodioxolyl, cyclopropyl, cyclobutyl, cyclopentyl, cyclohexyl and cycloheptyl.

4. The compound of claim 3 wherein $R^2$ is phenyl optionally substituted with 1-5 substituents of halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{1-10}$-alkylamino-, $C_{1-10}$-dialkylamino-, $C_{1-10}$-alkoxy or a ring selected from phenyl, pyridyl, pyrimidyl, pyridazinyl, pyrazinyl, triazinyl, thiophenyl, furyl, pyrrolyl, pyrazolyl, imidazolyl, triazolyl, tetrazolyl, thiazolyl, oxazolyl, isoxazolyl, isothiazolyl, thiadiazolyl, oxadiazolyl, pyrrolidinyl, oxazolinyl, isoxazolinyl, thiazolinyl, pyrazolinyl, morpholinyl, piperidinyl, piperazinyl and pyranyl, said ring optionally substituted with 1-5 substituents of $R^7$.

5. The compound of claim 1 wherein each of $A^1$ and $A^2$, independently, is CH;

each of $A^3$ and $A^4$, independently, is $CR^6$;

$R^1$ is a ring selected from phenyl, naphthyl, pyridyl, pyrimidyl, pyridazinyl, pyrazinyl, triazinyl, quinolinyl, isoquinolinyl, quinazolinyl, isoquinazolinyl, phthalazinyl, thiophenyl, thienopyrimidinyl, thienopyridinyl, furyl, pyrrolyl, pyrazolyl, pyrazolopyridinyl, pyrazoliopyrimidinyl, imidazolyl, triazolyl, triazolopyrazinyl, triazolopyridinyl, tetrazolyl, thiazolyl, oxazolyl, isoxazolyl, isothiazolyl, thiadiazolyl, oxadiazolyl, indolyl, isoindolyl, benzofuranyl, benzothiophenyl, benzimidazolyl, benzoxazolyl, benzisoxazolyl, benzothiazolyl, benzoisothiazolyl, benzotriazolyl, tetrahydrofuranyl, pyrrolidinyl, oxazolinyl, isoxazolinyl, thiazolinyl, pyrazolinyl and benzodioxolyl, said ring optionally susbstituted with 1-5 substituents of $R^7$;

$R^2$ is a ring selected from phenyl, pyridyl, pyrimidyl, pyridazinyl, pyrazinyl, triazinyl, thiophenyl, furyl, pyrrolyl, pyrazolyl, imidazolyl, triazolyl, tetrazolyl, thiazolyl, oxazolyl, isoxazolyl, isothiazolyl, thiadiazolyl, oxadiazolyl, pyrrolidinyl, oxazolinyl, isoxazolinyl, thiazolinyl, pyrazolinyl, morpholinyl, piperidinyl, piperazinyl and pyranyl, said ring optionally substituted with 1-5 substituents of $R^7$;

each $R^3$, independently, is H;

$R^4$ is H or $C_{1-4}$-alkyl;

$R^5$ is H, halo, haloalkyl, $C_{1-6}$-alkyl, —O—$C_{1-6}$-alkyl, —S—$C_{1-6}$-alkyl, —NH—$C_{1-6}$-alkyl, —N-di-$C_{1-6}$-alkyl, CN, OH or $NH_2$;

X is O;

Z is a cyclopropyl, cyclobutyl or cyclopentyl ring wherein 0, 1 or 2 carbon atoms of the ring are, independently, replaced with an oxygen atom and the ring optionally substituted independently with 1-5 substituents of $R^7$; and each $R^6$, independently, is halo, haloalkyl, $C_{1-6}$-alkyl, —O—$C_{1-6}$-alkyl, —S—$C_{1-6}$-alkyl, —NH—$C_{1-6}$-alkyl, —N-di-$C_{1-6}$-alkyl, CN, OH, $NH_2$, $C_{2-6}$-alkenyl, $C_{2-6}$-alkynyl, $C_{3-8}$-cycloalkyl, $C_{4-8}$-cycloalkenyl or $R^6$ is a fully unsaturated or partially or fully unsaturated 5- or 6-membered monocyclic or bicyclic ring formed of carbon atoms, said ring optionally including 1-5 heteroatoms selected from O, N, or S wherein said $C_{1-6}$-alkyl, $C_{2-6}$-alkenyl, $C_{2-6}$-alkynyl, $C_{3-8}$-cycloalkyl, $C_{4-8}$-cycloalkenyl, the $C_{1-6}$-alkyl portion of —O—$C_{1-6}$-alkyl, —S—$C_{1-6}$-alkyl, —NH—$C_{1-6}$-alkyl and —N-di-$C_{1-6}$-alkyl and ring are optionally substituted with 1-5 substituents of $R^7$.

6. The compound of claim 5 wherein ring Z is

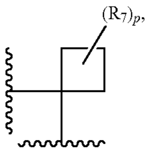
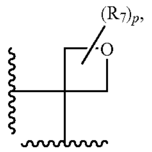
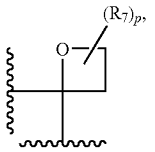
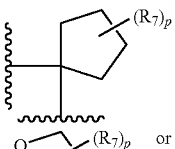
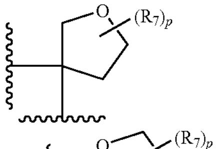
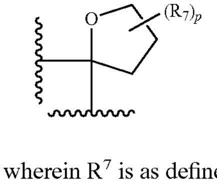
or
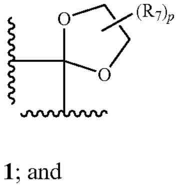

wherein $R^7$ is as defined in claim 1; and p is 0, 1, 2, 3 or 4.

7. The compound of claim 1 having a Formula II:

II

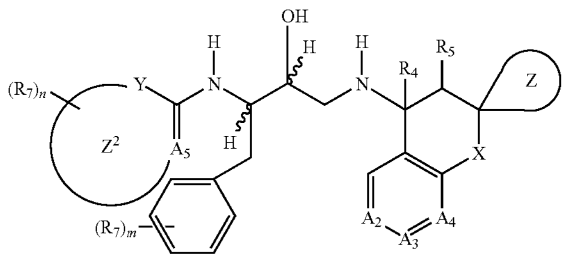

or a stereoisomer or pharmaceutically acceptable salt thereof, wherein each of $A^2$, $A^3$ and $A^4$, independently, is $CR^6$;

$A^5$ is CH or N;

$R^4$ is H, halo or $C_{1-6}$-alkyl;

$R^5$ is H, halo, haloalkyl, $C_{1-6}$-alkyl, —O—$C_{1-6}$-alkyl, —S—$C_{1-6}$-alkyl, —NH—$C_{1-6}$-alkyl, —N-di-$C_{1-6}$-alkyl, CN, OH or $NH_2$, wherein the $C_{1-6}$-alkyl and the $C_{1-6}$-alkyl portion of —O—$C_{1-6}$-alkyl, —S—$C_{1-6}$-alkyl, —NH—$C_{1-6}$-alkyl and —N-di-$C_{1-6}$-alkyl are optionally substituted independently with 1-5 substituents of $R^7$;

X is O;

Y is $CR^7R^7$, $NR^7$, S or O;

Z is a cyclopropyl, cyclobutyl or cyclopentyl ring wherein 0, 1 or 2 carbon atoms of the ring are, independently, replaced with an oxygen atom and the ring optionally substituted independently with 1-5 substituents of $R^7$;

$Z^2$ taken together with the carbon atom to which $A^5$ and Y are attached is a 4-, 5- or 6-membered monocylic ring or a 8-, 9- or 10-membered bicyclic ring, said ring formed of carbon atoms optionally including 1-3 heteroatoms if monocylic or 1-5 heteroatoms if bicyclic, said heteroatoms selected from N, O and S, and said ring optionally susbstituted with 1-5 substituents of $R^7$;

each $R^6$, independently, is halo, haloalkyl, $C_{1-6}$-alkyl, —O—$C_{1-6}$-alkyl, —S—$C_{1-6}$-alkyl, —NH—$C_{1-6}$-alkyl, —N-di-$C_{1-6}$-alkyl, CN, OH, $NH_2$, $C_{2-6}$-alkenyl, $C_{2-6}$-alkynyl, $C_{3-8}$-cycloalkyl, $C_{4-8}$-cycloalkenyl or $R^6$ is a fully unsaturated or partially or fully unsaturated 5- or 6-membered monocyclic or bicyclic ring formed of carbon atoms, said ring optionally including 1-5 heteroatoms selected from O, N, or S wherein said $C_{1-6}$-alkyl, $C_{2-6}$-alkenyl, $C_{2-6}$-alkynyl, $C_{3-8}$-cycloalkyl, $C_{4-8}$-cycloalkenyl, the $C_{1-6}$-alkyl portion of —O—$C_{1-6}$-alkyl, —S—$C_{1-6}$-alkyl, —NH—$C_{1-6}$-alkyl and —N-di-$C_{1-6}$-alkyl and ring are optionally substituted with 1-5 substituents of $R^7$;

each $R^7$, independently, is H, halo, haloalkyl, CN, OH, $NO_2$, $NH_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxy, $C_{1-10}$-thioalkoxy or a fully saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxy, $C_{1-10}$-thioalkoxy and ring of said ring system is optionally substituted independently with 1-5 substituents of halo, haloalkyl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxy, isobutoxy, tert-butoxy, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxy, benzyl or phenyl;

m is 0, 1, 2, 3 or 4; and n is 0, 1, 2, 3, 4 or 5.

8. The compound of claim 1, or a pharmaceutically acceptable salt thereof, selected from 3-((2S,3R)-4-(((4S)-6-ethyl-3,4-dihydrospiro[chromene-2,1'-cyclobutan]-4-yl)amino)-2-((2-fluorophenyl)amino)-3-hydroxybutyl)benzonitrile;

(2R,3S)-1-(((4S)-6-ethyl-3,4-dihydrospiro[chromene-2,1'-cyclobutan]-4-yl)amino)-3-((2-fluorophenyl)amino)-4-phenyl-2-butanol;

(2R,3S)-1-(((4S)-6-ethyl-3,4-dihydrospiro[chromene-2,1'-cyclopentan]-4-yl)amino)-3-((2-fluorophenyl)amino)-4-phenyl-2-butanol;

(2R,3S)-1-((S)-6-ethyl-2,2-spirocyclobutyl-chroman-4-ylamino)-4-phenyl-3-(4-(trifluoromethyl)pyrimidin-2-ylamino)butan-2-ol;

(2R,3S)-1-(((4S)-6-bromo-3,4-dihydrospiro[chromene-2,1'-cyclobutan]-4-yl)amino)-4-phenyl-3-([1,2,4]triazolo[4,3-a]pyrazin-8-ylamino)-2-butanol;

(2R,3S)-3-(1,3-benzoxazol-2-ylamino)- 1-(((4S)-6-ethyl-3,4-dihydrospiro[chromene-2,1'-cyclobutan]-4-yl)amino)-4-phenyl-2-butanol;

(2R,3S)-1-((S)-6-ethyl-2,2-spirocyclobutyl-chroman-4-ylamino)-4-phenyl-3-(4-ethyl-pyrimidin-2-ylamino)butan-2-ol;

(2R,3S)-1-((S)-6-ethyl-2,2-spirocyclobutyl-chroman-4-ylamino)-4-phenyl-3-(pyrimidin-2-ylamino)butan-2-ol;

(2R,3S)-3-((6-chloro-3-pyridazinyl)amino)-1-(((4S)-6-ethyl-3,4-dihydrospiro[chromene-2,1'-cyclobutan]-4-yl)amino)-4-phenyl-2-butanol;

(2R,3S)-1-(((4S)-6-ethyl-3,4-dihydrospiro[chromene-2,1'-cyclopentan]-4-yl)amino)-4-phenyl-3-(2-pyrazinylamino)-2-butanol;

(2R,3S)-3-(1,3-benzothiazol-2-ylamino)-1-(((4S)-6-ethyl-3,4-dihydrospiro[chromene-2,1'-cyclobutan]-4-yl)amino)-4-phenyl-2-butanol;

(2R,3S)-1-(((4S)-6-ethyl-3,4-dihydrospiro[chromene-2,1'-cyclobutan]-4-yl)amino)-4-phenyl-3-(3-pyridinylamino)-2-butanol;

(2R,3S)-1-((S)-6-ethyl-2,2-spirocyclobutyl-chroman-4-ylamino)-4-phenyl-3-(2-phenylpyrimidin-4-ylamino)butan-2-ol; and (2R,3S)-1-(((4S)-6-ethyl-3,4-dihydrospiro[chromene-2,1'-cyclobutan]-4-yl)amino)-4-phenyl-3-(4-pyridinylamino)-2-butanol.

9. A pharmaceutical composition comprising a pharmaceutically acceptable excipient and a compound according to claim 1.

10. A pharmaceutical composition comprising a pharmaceutically acceptable excipient and a compound according to claim 8.

* * * * *